US009250249B2

(12) United States Patent
Patton et al.

(10) Patent No.: US 9,250,249 B2
(45) Date of Patent: *Feb. 2, 2016

(54) AUTOPHAGY AND PHOSPHOLIPIDOSIS PATHWAY ASSAYS

(75) Inventors: Wayne Forrest Patton, Dix Hills, NY (US); Jack Coleman, East Northport, NY (US); Yuejun Xiang, Bayside, NY (US); Praveen Pande, Holbrook, NY (US); Zaiguo Li, Fresh Meadows, NY (US)

(73) Assignee: Enzo Biochem, Inc., Farmingdale, NY (US)

( * ) Notice: Subject to any disclaimer, the term of this patent is extended or adjusted under 35 U.S.C. 154(b) by 1054 days.

This patent is subject to a terminal disclaimer.

(21) Appl. No.: 12/584,958

(22) Filed: Sep. 14, 2009

(65) Prior Publication Data

US 2010/0093004 A1    Apr. 15, 2010

Related U.S. Application Data

(63) Continuation-in-part of application No. 12/287,882, filed on Oct. 13, 2008, which is a continuation-in-part of application No. 12/231,988, filed on Sep. 8, 2008.

(51) Int. Cl.
| | |
|---|---|
| *G01N 33/68* | (2006.01) |
| *G01N 33/50* | (2006.01) |
| *G01N 33/58* | (2006.01) |
| *G01N 33/94* | (2006.01) |

(52) U.S. Cl.
CPC ........ *G01N 33/6893* (2013.01); *G01N 33/5076* (2013.01); *G01N 33/582* (2013.01); *G01N 33/94* (2013.01); *G01N 2500/10* (2013.01); *G01N 2800/02* (2013.01); *G01N 2800/04* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2,195,462 | A | 4/1940 | Krause |
| 3,792,968 | A | 2/1974 | Rickenbacher et al. |
| 3,823,169 | A | 7/1974 | Staub |
| 4,868,103 | A | 9/1989 | Stavrianopoulos et al. |
| 5,118,801 | A | 6/1992 | Lizardi et al. |
| 5,210,015 | A | 5/1993 | Gelfand et al. |
| 5,338,854 | A | 8/1994 | Kang et al. |
| 5,401,847 | A | 3/1995 | Glazer et al. |
| 5,459,268 | A | 10/1995 | Haugland et al. |

(Continued)

FOREIGN PATENT DOCUMENTS

WO    WO2008/037394    4/2008

OTHER PUBLICATIONS

Yuang, Yu et al. "Current Status of Diagnosis and Treatment of Lysosomal Storage Diseases in China", 2006, 245-251.*

(Continued)

*Primary Examiner* — Clinton Brooks
(74) *Attorney, Agent, or Firm* — Louis M. Heidelberger

(57) ABSTRACT

Provided are assays useful for detecting and monitoring autophagy and phospholipidosis, including the progression of lysosomal storage diseases. Drugs and treatments for lysosomal storage diseases can be monitored for effectiveness in lysosomal storage disease conditions. Drug candidates and suspected toxic agents can also be screened for toxicity to cells, tissues and organs. Also provided are methods for distinguishing between phospholipidosis activators and autophagy pathway perturbation agents.

17 Claims, 8 Drawing Sheets

(56) References Cited

U.S. PATENT DOCUMENTS

| | | | |
|---|---|---|---|
| 5,491,084 | A | 2/1996 | Chalfie et al. |
| 5,538,848 | A | 7/1996 | Livak et al. |
| 5,580,990 | A | 12/1996 | Van Den Berg et al. |
| 5,625,048 | A | 4/1997 | Tsien et al. |
| 5,646,264 | A | 7/1997 | Glazer et al. |
| 5,686,261 | A | 11/1997 | Zhang et al. |
| 5,777,079 | A | 7/1998 | Tsien et al. |
| 5,800,996 | A | 9/1998 | Lee et al. |
| 5,804,387 | A | 9/1998 | Cormack et al. |
| 5,852,191 | A | 12/1998 | Karandikar et al. |
| 5,869,689 | A | 2/1999 | Zhang et al. |
| 5,925,517 | A | 7/1999 | Tyagi et al. |
| 5,968,738 | A | 10/1999 | Anderson et al. |
| 5,981,747 | A | 11/1999 | Mujumdar et al. |
| 5,994,056 | A | 11/1999 | Higuchi et al. |
| 5,994,077 | A | 11/1999 | Valdivia et al. |
| 6,004,536 | A | 12/1999 | Leung et al. |
| 6,008,373 | A | 12/1999 | Waggoner et al. |
| 6,022,944 | A | 2/2000 | Weaver et al. |
| 6,027,881 | A | 2/2000 | Pavlakis et al. |
| 6,054,321 | A | 4/2000 | Tsien et al. |
| 6,066,476 | A | 5/2000 | Tsien et al. |
| 6,077,707 | A | 6/2000 | Tsien et al. |
| 6,090,919 | A | 7/2000 | Cormack et al. |
| 6,124,128 | A | 9/2000 | Tsien et al. |
| 6,133,445 | A | 10/2000 | Waggoner et al. |
| 6,140,500 | A | 10/2000 | Yan et al. |
| 6,146,826 | A | 11/2000 | Chalfie et al. |
| 6,172,188 | B1 | 1/2001 | Thastrup et al. |
| 6,174,670 | B1 | 1/2001 | Wittwer et al. |
| 6,291,203 | B1 | 9/2001 | Poot et al. |
| 6,468,753 | B1 | 10/2002 | Smith et al. |
| 6,593,465 | B1 | 7/2003 | Wolff et al. |
| 6,664,047 | B1 | 12/2003 | Haugland et al. |
| 6,686,145 | B1 | 2/2004 | Waggoner et al. |
| 6,969,597 | B2 | 11/2005 | Lukyanov et al. |
| 7,060,427 | B2 | 6/2006 | Smith et al. |
| 7,150,979 | B2 | 12/2006 | Lukyanov et al. |
| 7,157,565 | B2 | 1/2007 | Lukyanov et al. |
| 7,166,444 | B2 | 1/2007 | Lukyanov et al. |
| 7,183,399 | B2 | 2/2007 | Lukyanov et al. |
| 7,297,782 | B2 | 11/2007 | Labas et al. |
| 2002/0077366 | A1 | 6/2002 | Banerjee et al. |
| 2003/0225247 | A1 | 12/2003 | Stavrianopoulos et al. |
| 2005/0054006 | A1 | 3/2005 | Chang et al. |
| 2007/0111251 | A1 | 5/2007 | Rosania et al. |
| 2008/0166749 | A1 | 7/2008 | Cubitt |
| 2010/0062429 | A1* | 3/2010 | Patton et al. ............... 435/6 |
| 2010/0062460 | A1* | 3/2010 | Pande et al. ............... 435/7.2 |

OTHER PUBLICATIONS

Matsuzawa, Y. et al. The Journal of Biological Chemistry, 1980, 5190-5194.*
Albay et al., Chloroquine-induced lipidosis mimicking Fabry disease, Modern Pathology 2005, 733-738, 18.
Anderson and Borlak, Drug-induced phospholipidosis, FEBS Letters 2006, 5533-5540, 580.
Ballabio and Gieselmann., Lysosomal disorders: From storage to cellular damage, Biochimica et Biophysica Acta 2009, 684-696, 1793.
Bassoe et al., Investigations of Phagosomes, Mitochondria, and Acidic Granules in Human Neutrophils Using Fluorescent Probes, Cytometry Part B (Clinical Cytometry) 2003, 21-29, 51B.
Bhandari et al., Phospholipidosis Assay in HepG2 Cells and Rat or Rhesus Hepatocytes Using Phospholipid Probe NBD-PE, ASSAY and Drug Development Technologies 2008, 407-419, 6(3).
Boldyrev et al., New BODIPY lipid probes for fluorescence studies of membranes, J Lipid Res. 2007,1518-1532, 48(7).
Bondok et al., Fluorescence histochemical study of the localisation and distribution of beta-adrenergic receptor sites in the spinal cord and cerebellum of the chicken, J. Anat. 1988, 167-174, 160.
Bracamonte et al., Iatrogenic phospholipidosis mimicking Fabry disease, Am. J. Kidney Diseases 2006, 844-850, 48(5).
Casartelli et al., A cell-based approach for the early assessment of the phospholipidogenic potential in pharmaceutical research and drug development, Cell Biology and Toxicology 2003, 161-176,19.
Cornett and Meizel, 9-APP, a Flourescent Beta-Adrenergic Antagonist, Enters the Hamster Sperm Acrosome in a Manner Inconsistent With Binding to Beta-Adrenergic Receptors, The Journal of Histochemistry and Cytochemistry 1980, 462-464, 28(5).
Cramb, Gordon, Selective lysosomal uptake and accumulation of the beta-adrenergic antagonist propranolol in cultured and isolated cell systems, Biochemical Pharmacology 1986, 1365-1372, 35(8).
Cramer and Ulrich, Cytotoxicity and lamellar body induction potential of a racemic benzamide antiarrhythmic compound and enantiomers in cultured rat hepatocytes, Toxic. in Vitro 1994,1083-1090, 8(5).
Deng et al., Fluorescent Conjugates of Brefeldin A Selectively Stain the Endoplasmic Reticulum and Golgi Complex of Living Cells, J Histochem Cytochem 1995, 907-915, 43(9).
Dickens et al., Antioxidant and Lysosomotropic Properties of Acridine-propranolol: Protection against Oxidative Endothelial Cell Injury, J Mol Cell Cardiol 2002, 129-137, 34.
Diez-Blanco et al., Isolation, characterization and phospholipid composition of lamellar bodies and subcellular fractions from dog lung, Int. J. Biochem. 1987, 693-698, 19(8).
Diwu et al., A novel acidotropic pH indicator and its potential application in labeling acidic organelles of live cells, Chemistry & Biology, 1999, 411-418, 6.
Freundt et al., Photoconversion of Lysotracker Red to a green fluorescent molecule, Cell Research 2007, 956-958, 17.
Fujimura et al., Cell-based fluorescence assay for evaluation of new-drugs potential for phospholipidosis in an early stage of drug development, Experimental and Toxicologic Pathology 2007, 375-382, 58.
Gum et al., Analysis of two matrix metalloproteinase inhibitors and their metabolites for induction of phospholipidosis in rat and human hepatocytes, Biochemical Pharmacology 2001,1661-1673, 62.
Hjelmeland et al., SB-431542, a small molecule transforming growth factor-beta-receptor antagonist, inhibits human glioma cell line proliferation and motility, Mol Cancer Ther 2004, 737-745, 3(6).
Ikeda et al., Drug-induced phospholipidosis is caused by blockade of mannose 6-phosphate receptor-mediated targeting of lysosomal enzymes, Biochemical and Biophysical Research Communications 2008, 268-274, 377.
Kasahara et al., Establishment of an In Vitro High-Throughput Screening Assay for Detecting Phospholipidosis-Inducing Potential, Toxicological Sciences 2006, 133-141, 90(1).
Lee et al., Development of novel cell-permeable DNA sensitive dyes using combinatorial synthesis and cell-based screening, Chem. Commun. , 2003, 1852-1853.
Lee et al., DEVDase detection in intact apoptotic cells using the cell permeant fluorogenic substrate, (z-DEVD)2-cresyl violet, Biotechniques 2003, 1080-1085, 35(5).
Lemieux et al., Quantitation of the lysosomotropic character of cationic amphiphilic drugs using the fluorescent basic amine Red DND-99, Analytical Biochemistry 2004, 247-251, 327.
Li and Bittman, Synthesis and Spectral Properties of Cholesterol- and FTY720-Containing Boron Dipyrromethene Dyes, J Org Chem. 2007, 8376-8382, 72(22).
Morelli et al., Validation of an in vitro screen for phospholipidosis using a high-content biology platform, Cell Biology and Toxicology 2006; 15-27, 22.
Muller-Hocker et al., Chloroquine-Induced Phospholipidosis of the Kidney Mimicking Fabry's Disease: Case Report and Review of the Literature, Hum Pathol 2003, 285-289, 34.
Nadrigny et al., Systematic Colocalization Errors between Acridine Orange and EGFP in Astrocyte Vesicular Organelles, Biophysical Journal, 2007 969-980, 93.
Mesens et al., A 96-well flow cytometric screening assay for detecting in vitro phospholipidosis-induction in the drug discovery phase, Toxicology in Vitro 2009, 217-226, 23.
Nioi et al., In Vitro Detection of Drug-Induced Phospholipidosis Using Gene Expression and Fluorescent Phospholipid—Based Methodologies, Toxicological Sciences 2007, 162-173, 99(1).

(56) References Cited

OTHER PUBLICATIONS

Nioi et al., Monitoring the Accumulation of Fluorescently Labeled Phospholipids in Cell Cultures Provides an Accurate Screen for Drugs that Induce Phospholipidosis, Drug and Chemical Toxicology 2008, 515-528, 31.
Pagano et al., Molecular Trapping of a Fluorescent Ceramide Analogue at the Golgi Apparatus of Fixed Cells: Interaction with Endogenous Lipids Provides a trans-Golgi Marker for Both Light and Electron Microscopy, The Journal of Cell Biology 1989, 2067-2079, 109
Pagano et al., A Novel Fluorescent Ceramide Analogue for Studying Membrane Traffic in Animal Cells: Accumulation at the Golgi Apparatus Results in Altered Spectral Properties of the Sphingolipid Precursor, The Journal of Cell Biology 1991, 1267-1279, 113(6).
Poot et al., Analysis of Mitochondrial Morphology and Function with Novel Fixable Fluorescent Stains, The Joournal of Histochemistry and Cytochemistry, 1996,1363-1372, 44(12).
Rashid et al., Predicting the behaviour and selectivity of fluorescent probes for lysosomes and related structures by means of structure-activity models, Histochemical Journal 1991, 450-459, 23.
Rosania et al., Combinatorial Approach to Organelle-Targeted Fluorescent Library Based on the Styryl Scaffold, J Am Chem. Soc, 2003, 1130-1131, 125.
Rutledge et al., Direct Visualization of Lipid Deposition and Reverse Lipid Transport in a Perfused Artery Roles of VLDL and HDL, Circ Res. 2000, 768-773, 86.
Sanchez et al., Amiodarone and Bepridil Inhibit Anthrax Toxin Entry into Host Cells, Antimicrobial Agents and Chemotherapy, 2007, 2403-2411, 51(7).
Tomizawa et al., Physicochemical and cell-based approach for early screening of phospholipidosis-inducing potential, Journal of Toxicological Sciences, 2006, 315-324, 31(4).
Ulrich et al., An In Vitro Fluorescence Assay for the Detection of Drug-Induced Cytoplasmic Lamellar Bodies, Toxicology Methods 1991, 89-105, 1(2).
Ulrich and Cramer, Potential to induce lamellar bodies and acute cytotoxicity of 6'-alkyl analogues of spectinomycin in primary cultures of rat hepatocyes, Toxic. In Vitro, 1991, 239-245, 5(3).
Vibet et al- Differential Subcellular Distribution of Mitoxantrone in Relation to Chemosensitization in Two Human Breast Cancer Cell Lines, Drug Metabolism and Disposition 2007, 822-828, 35(5).
Xu et al., Berbamine: A novel inhibitor of bcr/abl fusion gene with potent anti-leukemia activity, Leukemia Research 2006, 17-23, 30.
Yamamoto et al., Bafilomycin Al Prevents Maturation of Autophagic Vacuoles by Inhibiting Fusion between Autophagosomes and Lysosomes in Rat Hepatoma Cell Line, H-4-II-E Cells, Cell Structure and Function 1998, 33-42, 23.
Zhang et al., A simple statistical parameter for use in evaluation and validation of high throughput screening assays, J Biomol. Screen. 1999, 67-73, 4(2).
Zhang et al., Structure of the yeast vaculolar ATPase, J. Biol. Chem. 2008, 35983-35995, 283(51).
Zhang et al., Small molecule regulators of autophagy identified by an image-based high throughput screen, Proc. Nat'l. Acad. Sci. 2007, 19023-19028, 104(48).
Winkelmann et al., "Chemotherapeutically Active Antraquinones," *Drug Res.*, vol. 36(1), No. 2, pp. 234-247 (1986).
Almeda et al., Characterization of the phospholidogenic potential of 4(1H)-pyridone antimalarial derivatives, *Toxicology in Vitro*, vol. 23, pp. 1528-1534 (2009).
Baciu et al., Degradative transport of cationic amphiphilic drugs across phospholipid bilayers, *Phil Trans. R. soc. A*, 364, pp. 2597-2614 (2006).
Cox, T. M., "Biomarkers in lysosomal storage diseases: a review,"*Acta Paediatric*, vol. 94 (Suppl. 447), pp. 39-42 (2005).
Gatt et al., A Fluorometric Determination of Sphingomyelinase by Use of Fluorescent Derivatives of Phingomyeli, and its Application to Diagnosis of Niemann-Pick Disease, *Clinical Chemistry*, vol. 26, No. 1, pp. 93-96 (1980).
Huange et al., *Bioorg. Med. Chem.*, vol. 13, pp. 1435-1444 (2005).
Invitrogen, HCS LipidTox™ Phospholiposis Detection Reagents. Sep. 2006, MP 34350.
Ishiguro et al., "Novel application of 4-nitro-7-(1-piperazinyl)-2,1,3-benzoxadiazole to visualize lysosomes in live cells," *BioTechniques*, vol. 45, pp. 465-468 (2008).
Maloteaux et al., Trapping of Labelled Ligands in Intact Cells: a Pitfall in Binding Studies, *Biochemical Pharmacology*, vol. 32, pp. 2543-2548 (1983).
Natalie et al., "a 96-well flow cytometric screening assay for detecting in vitro phospholipidosis-induction in the drug discovery phase," *Toxicology in Vitro*, vol. 23, pp. 217-226 (2009).
Raben et al., "Monitoring autophagy in lysomal storage disorders," *Methods Enzymol.*, vol. 453, pp. 417-449 (2009).
Seglen et al., "3-Methyladenine: Specific inhibitor of autophagic/lysomal protein degradation in isolated rat hepatocytes, "*Proc. Natl. Acad. Sci.* vol. 79, pp. 1889-1892 (1982).
Smith et al., "Characteristics of a Novel Deep Red/Infrared Fluorescent Cell-Permeant DNA Probe, DRAQ5, in Intact Human Cells Analyzed by Flow Cytometry, Confocal and Multiphoton Microscopy," *Cytometry*, vol. 40, pp. 280-291 (2000).
Smith et al., "A novel cell permeant and far red-fluorescing DNA probe, DRAQ5, for blood cell discrimination by flow cytometry," *Journal of Immunologaical Methods*, vol. 229, pp. 131-139 (1999).
Snyder et al., Deceased uptake of bodipy-labelled compounds in the presence of the nuclear stain, DRAQ5, *Journal of Microscopy*, vol. 211, pp. 208-211 (2003).
Zal et al., Spectral Shift of Fluorescent Dye FM4-64 Reveals Distinct Microenvironment of Nuclear Envelope in Living Cells, *Traffice*, vol. 7, pp. 16;07-1613 (2006).
Zeigler et al., Prenatal diagnosis of Krabbe disease using a fluorescent derivative of galactosylceramide, *Clinica Chimica Acta*, vol. 142, pp. 313-318 (1984).

\* cited by examiner

Schematic Illustration for Multiplexed Detection of Phospholipidosis Inducers and Autophagy Pathway Inhibitors Figure 6
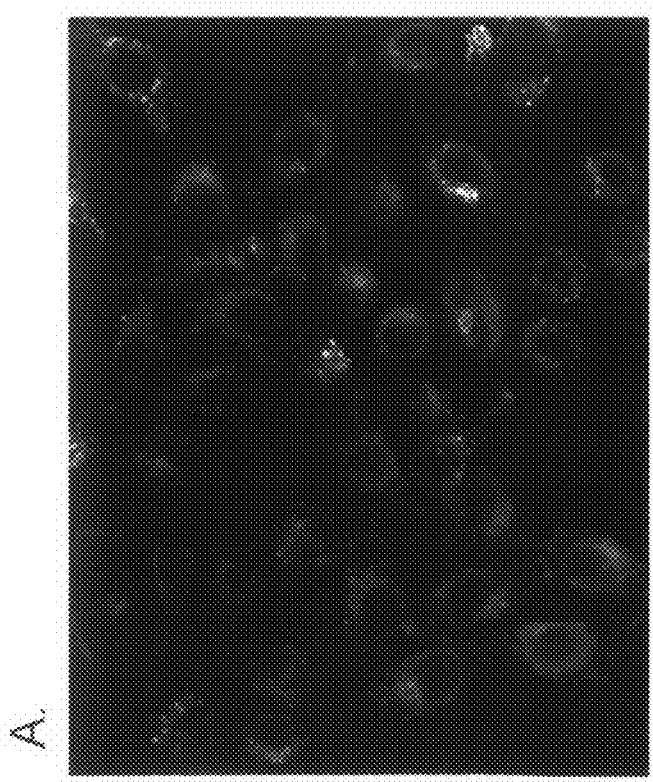

Figure 8
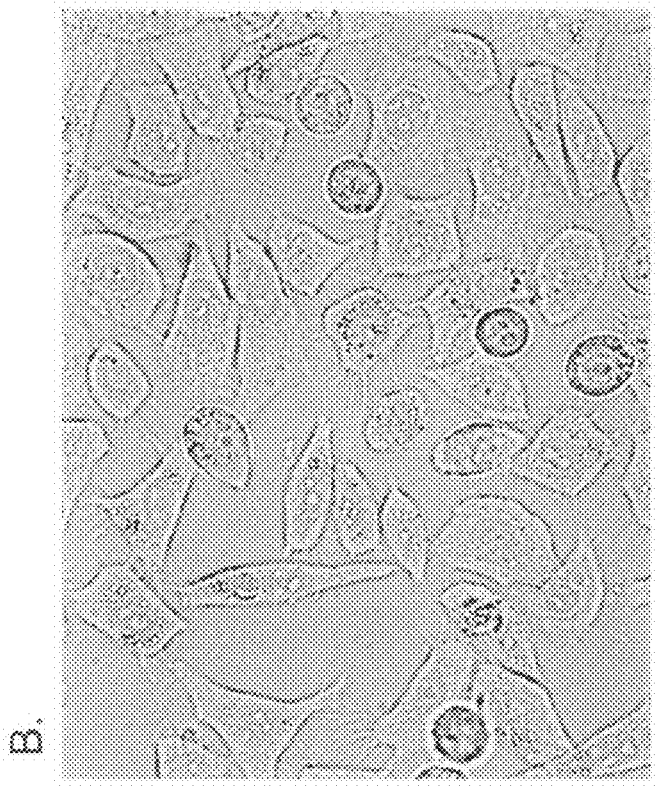
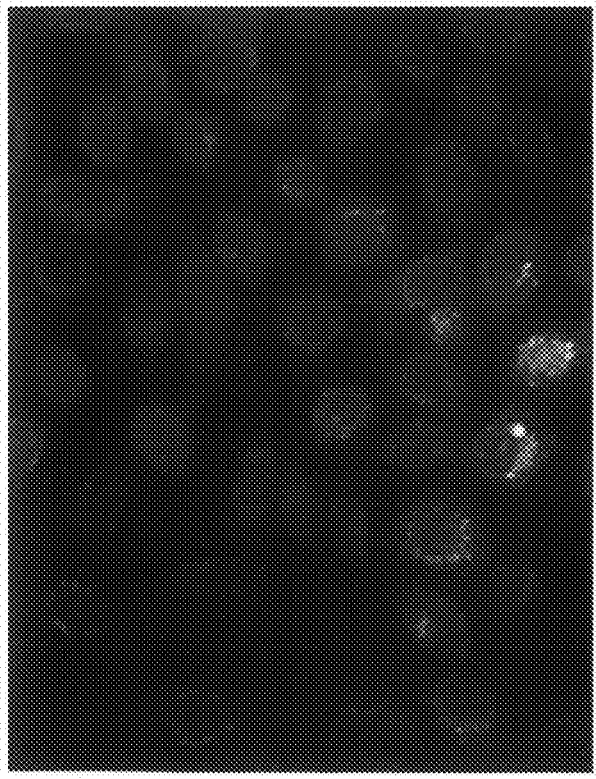

AUTOPHAGY AND PHOSPHOLIPIDOSIS PATHWAY ASSAYS

RELATED APPLICATIONS

This application is a continuation-in-part of U.S. patent application Ser. No. 12/287,882, filed on Oct. 13, 2008, which is a continuation-in-part of U.S. patent application Ser. No. 12/231,988, filed on Sep. 8, 2008, the contents of both such applications being incorporated by reference in their entirety.

FIELD OF THE INVENTION

This invention relates to lysosomal storage diseases, and more particularly to methods for detecting and monitoring the progression of lysosomal storage diseases as well as methods for monitoring the effectiveness of drugs or remedies used to manage, treat or cure such diseases. This invention also relates to toxicity screening methods, and more particularly, methods and assays for screening drug candidates and suspected toxic agents to determine their toxicity to cells, tissues or organs. This invention also relates to phospholipidosis and autophagy, and more particularly, to methods for distinguishing phospholipidosis activators and autophagy pathway perturbation agents.

All patents, patent applications, patent publications, scientific articles and the like, cited or identified in this application, are hereby incorporated by reference in their entirety in order to describe more fully the state of the art to which the present invention pertains.

BACKGROUND OF THE INVENTION

Cell-based assays are increasingly gaining in popularity in the pharmaceutical industry due to their high physiological relevance. Additional advantages include their ability to predict compound usefulness, evaluate molecular interactions, identify toxicity, distinguish cell type-specific drug effects, and determine drug penetration. Cell-based assays are relevant throughout the drug discovery pipeline, because they are capable of providing data from target characterization and validation to lead identification (primary and secondary screening) to terminal stages of toxicology. Current industry trends of performing drug screening with cell context demand easily monitored, non-invasive reporters. This fundamental approach increases efficiency, reduces costs, and results in shorter time to market for new drugs. In order to fail compounds early, information-rich data for accurate early-stage decision making is required. Such data may be derived by screening compounds in context, that is, by screening in relevant living systems, rather than with classical biochemical assays. These screening systems often incorporate sophisticated imaging platforms, such as high-content screening (HCS) workstations. The industrialization of fluorescent microscopy has led to the development of these high-throughput imaging platforms capable of HCS. When coupled with fluorescent reporter technology, HCS has provided information-rich drug screens, as well as access to novel types of drug targets.

While suitable for analysis of cell surfaces and permeabilized cells, fluorescently-labeled antibodies have few practical applications for intracellular imaging in living cells, due to their inherent inability to penetrate to their targets, which has given rise to development of cell-permeable small molecule organic fluorochromes. Certain ones of these fluorochromes naturally sequester inside-specific organelles, based upon biophysical or biochemical properties favoring that distribution. Acceptable small molecule organic probes for cell imaging and analysis need to be minimally perturbing, versatile, stable, easy-to-use, and easy to detect using non-invasive imaging equipment. A problem with the classical organic probes from a histological standpoint is that many of them require cofactors or, by requiring fixation or staining, report only on the static condition of a dead cell. The required additional steps may be time consuming and expensive and, in the case of fixing and staining, may lack biological relevance. In the context of the analyses described above, an organic probe must be able to report upon events in living cells and in real time. Simplicity is of key importance, especially in the context of drug screening.

While various organic fluorochromes have been developed in the past for live cell analysis, typically they were devised using unperturbed cells. Thus, such organic fluorochromes statically report upon organelle spatial position within cells without the ability to monitor dynamic changes. For instance, several U.S. patent documents (U.S. Pat. Nos. 5,338,854, 5,459,268, 5,686,261, 5,869,689, 6,004,536, 6,140,500 and 6,291,203 B1, as well as US Patent Applications 2005/0054006 and 2007/0111251 A1, (foregoing patents and patent applications incorporated herein by reference) disclose organic fluorochromes which are described as useful for visualizing membranes, mitochondria, nuclei and/or acidic organelles. Additional examples of various fluorochromes and their application in biological imaging may be found in the published literature (see, for example, Pagano et al, 1989; Pagano et al, 1991; Deng et al, 1995; Poot et al, 1996; Diwu et al 1999; Rutledge et al, 2000; Lee et al, 2003; Bassøe et al, 2003; Rosania et al, 2003, Li et al 2007; Boldyrev et al, 2007; Nadrigny et al, 2007). These dyes have been created using a number of fluorophores, most commonly dipyrrometheneboron difluoride (BODIPY), cyanine, carbocyanine, styryl and diaminoxanthene core structures. Typical emission maxima for these organic fluorophores span from 430 to 620 nm. Many of these dyes display certain suboptimal properties, such as a propensity to photo-bleach, metachromasy and even a tendency to photo-convert to different emission maxima upon brief exposure to broad-band illumination.

JC-1 dye is notable in its ability to monitor the dynamics of mitochondrial membrane potential changes and consequently the energetic state of cells (Smiley et al, 1991). Unfortunately, with respect to lysosomes and lysosome-like vesticles (autophagosomes, autophagolysosomes), there has been a notable lack of probes that have the ability to track organelle dynamics arising from drug treatment or intracellular membrane trafficking anomalies.

Spectral Problems Associated With Previously Devised Organic Fluorochromes for Analysis of Lysosomes Fluorescence co-localization imaging is a powerful method for exploring the targeting of molecules to intracellular compartments and for screening of their associations and interactions. In these kinds of experiments, distinct fluorochromes and/or fluorescent proteins of interest are imaged as spectrally separated detection channels. The fluorescence intensity in each channel is ideally dominated by spatial and concentration information derived from one fluorophore only. Many commercially available organic fluorophores for subcellular analysis are disadvantaged in displaying suboptimal properties relating to these types of applications.

Lysotracker Red DND-99 (Invitrogen, Carlsbad, Calif.) contains a BODIPY fluorophore in the form of a conjugated multi-pyrrole ring structure and also contains a weakly basic amine that causes the fluorochrome to accumulate selectively in acidic compartments, exhibiting red fluorescence upon appropriate illumination (excitation: 577 nm, emission: 590 nm) (Freundt et al, 2007). Lysotracker Red is structurally related to Lysotracker Green but the former has an additional pyrrole ring in conjugation with the primary structure, which produces a longer wavelength emission. Lysotracker Red has commonly been used in multi-color imaging studies as a lysosomal marker to determine intracellular localization of GFP-tagged proteins by fluorescence or confocal microscopy. Excitation of the red-emitting molecule with broadband illumination induces molecular changes, however, thus rendering its photochemical properties similar to those of Lysotracker Green. The similarities between the spectra of Lysotracker Green and converted Lysotracker Red suggest that the third pyrrole ring is taken out of conjugation during the photo-conversion process, leading to a shorter wavelength dye emission. Thus, Lysotracker Red staining for epifluorescence or confocal microscopy, in conjunction with visualization of GFP or FITC, leads to spurious results due to photo-conversion of the fluorophore (Freundt et al, 2007).

Acridine orange (Sigma-Aldrich, Saint Louis, Mo. and other sources) has also been used extensively as a fluorescent probe of lysosomes and other acidic subcellular compartments. Acridine orange's metachromasy results, however, in the concomitant emission of green and red fluorescence from stained cells and tissue (Nadrigny et al, 2007). Evanescent-field imaging with spectral fluorescence detection, as well as fluorescence lifetime imaging microscopy demonstrate that green fluorescent acridine orange monomers inevitably coexist with red fluorescing acridine orange dimers in labeled cells. The green monomer emission spectrally overlaps with that of GFP and produces a false apparent co-localization on dual-color images. Due to its complicated photochemistry and interaction with cellular constituents, acridine orange is a particularly problematic label for multi-color fluorescence imaging, both for dual-band and spectral detection. Extreme caution is required, therefore, when deriving quantitative co-localization information from images of GFP-tagged proteins in cells co-labeled with acridine orange.

Cationic amphiphilic drug tracers have been disclosed. See, for example, acridine-propranolol disclosed in Dickens et al., *J Mol Cell Cardiol* 34:129-137 (2002); Bondok et al., *J. Anat.* 160:161-174 (1988); and Cornett et al., *J. Histochem. And Cytochem.* 28:462-464 (1980); and mitoxantrone disclosed in Vibet et al., *Drug Metabolism and Disposition* 35:822-828 (2007); each incorporated by reference.

Problems Associated With Previously Described Fluorochromes Targeted to Lysosomes and Lysosome-Like Bodies The accumulation of cationic amphiphilic drugs, toxic agents and other basic compounds inside acidic subcellular organelles is referred to as lysosomotropism. While many drugs require the presence of a cationic moiety for intrinsic bioactivity, their accumulation into subcellular organelles can also lead to undesirable tissue distribution, alkalinization of lysosomes, phospholipidosis and aberrant pharmacokinetic disposition (Ikeda et al, 2008). Over fifty cationic amphiphilic drugs, including antibiotics, antidepressants, antipsychotics, and antimalarial and antiarrhythmic agents are known to trigger phospholipidosis, which is typified by the excessive intracellular accumulation of phospholipids within lysosomes as lamellar bodies (Anderson and Borlak, 2006). Some commonly prescribed drugs known to perturb lysosomes by inducing phospholipidosis include propranolol, triparanol, chlorpromazine, chloroquine, fluoxetine, clindamycin and ketoconazole.

The origins of drug-induced lamellar bodies remain unresolved, though they appear to be generated by autophagic or heterophagic processes (Anderson and Borlak, 2006). Several mechanisms have been proposed to explain drug-induced phospholipidosis including the formation of drug-phospholipid complexes that are resistant to degradation by lysosomal phospholipases, direct inhibition of phospholipases themselves, and inhibition of intracellular pathways regulating phospholipid metabolism.

Only one instance can be found wherein a cationic amphiphilic fluorophore has been employed for monitoring drug-induced phospholipidosis (Lemieux et al, 2004). Lysotracker Red DND-99 (Invitrogen) was used to stain lysosomes and inhibition or displacement of the accumulated dye by test agents was subsequently monitored by fluorescence microscopy. Thus, the drug-induced vacuoles were not explicitly stained using the fluorescent probe, but rather an absence of signal was used as an indirect indication that the vacuoles were formed.

Numerous other in vitro methods for detecting phospholipidosis using different cell types including primary hepatocytes, peripheral blood monocytes and various cells lines, in combination with electron microscopy, flow cytometry, fluorescent microscopy or spectrofluorometry have previously been described (Ulrich et al, 1991; Cramer and Ulrich, 1994; Kasahara et al, 2006; Ikeda et al 2008; Gum et al, 2001; Lemieux et al 2004; Fujimura et al 2007; Tomizawa et al, 2006; Natalie et al, 2009; Nioi et al, 2008; Nioi et al, 2007; Bhandari et al, 2008; Morelli et al, 2006; Casartelli et al, 2003). Due to their inherent low throughput, however, many of these in vitro methods are not ideal for routine compound screening during early stage drug development. For example, electron microscopy, fluorescence microscopy and flow cytometry are generally considered low throughput platforms for routine drug screening purposes, especially when contrasted with fluorescence-based multi-well microplate assays. Additionally, some of the above cited assays depend upon difficult to procure cells. For instance, the preparation of primary hepatocytes or peripheral blood monocytes is too laborious for routine drug screening assay programs.

Many of the previously described cell-based methods require a relatively long period of treatment with the test agent before phospholipidosis can be detected (24-72 h). Additionally, the vast majority of the assays are based upon fluorescently labeled phospholipid analogs, such as NBD-PE, NBD-PC and Lipid-Tox reagent (Invitrogen, Carlsbad, Calif.), which require co-incubation of the analog with the drug during the extended incubation period. Distinct types of phospholipids appear to accumulate differently during phospholipidosis, however, and no explicit comparison of the performance of the different fluorescent lipid analogs has been performed to date (Diez-Blanco et al., 1987). The methods also depend upon permeabilization and fixation of the cells prior to analysis, which adds considerably to the overhead associated with the workfklow. What is needed is a fluorescent probe that faithfully highlights increases in vacuolar number and volume associated with exposure of cells and/or tissues to xenobiotic compounds.

SUMMARY OF THE INVENTION

This invention provides a method of detecting the presence of a lysosomal storage disease in a subject in which the following steps are carried out: (a) obtaining a sample containing cells from the subject; (b) contacting the sample with a cationic amphiphilic tracer compound that localizes to a vacuole in a cell; and (c) detecting the cationic amphiphilic tracer compound, thereby determining whether there exists an excess above normal accumulation of vacuoles within the cells of the sample, such an excess above normal accumulation of vacuoles being indicative of the lysosomal storage disease sought to be detected.

This invention also provides a method of monitoring the progression of a lysosomal storage disease in a subject by comparing vacuole accumulation over a course of ($T_2$-$T_1$) time interval(s). In this monitoring method, the following steps are carried out: (a) obtaining from the subject at time $T_1$ a first sample containing cells; (b) contacting the first sample with a first cationic amphiphilic tracer compound that localizes to a vacuole in a cell; (c) detecting the first cationic amphiphilic tracer compound, thereby determining the accumulation of vacuoles within the cells of the first sample at time $T_1$; (d) obtaining from the subject at a later time $T_2$ a second sample containing cells; (e) contacting the second sample with a second cationic amphiphilic tracer compound that localizes to a vacuole in a cell; (f) detecting the second cationic amphiphilic tracer compound, thereby determining the accumulation of vacuoles within cells of the second sample at time $T_2$; and (g) comparing the accumulation of vacuoles between the first sample at time $T_1$ and the second sample at time $T_2$, thereby monitoring the progression of lysosome storage disease in the subject.

Also provided by this invention is a method of monitoring the effectiveness of a drug or remedy used to manage, treat or cure a lysosomal storage disease in a subject. To monitor the effectiveness of such a drug or remedy, the following steps are carried out: (a) obtaining from the subject at time $T_1$ a first sample containing cells; (b contacting the first sample with a first cationic amphiphilic tracer compound that localizes to a vacuole in a cell; (c) detecting the first cationic amphiphilic tracer compound, thereby determining the accumulation of vacuoles within the cells of the first sample at time $T_1$; (d) obtaining from the subject at a later time $T_2$ a second sample containing cells; (e) contacting the second sample with a second cationic amphiphilic tracer compound that localizes to a vacuole in a cell; (f) detecting the second cationic amphiphilic tracer compound, thereby determining the accumulation of vacuoles within cells of the second sample at time $T_2$; and (g) comparing the accumulation of vacuoles between the first sample at time $T_1$ and the second sample at time $T_2$, thereby monitoring the effectiveness of the drug used to manage, treat or cure lysosome storage.

Further provided by the invention herein is a method of screening drug candidates to determine their toxicity to cells, tissues or organs. To screen drug candidates for toxicity, the following steps are carried out: (a) providing: (i) at least one first sample and one second sample of mammalian cells; (ii) a drug candidate for screening; (iii) a drug diluting vehicle or carrier; and (iv) a cationic amphiphilic tracer compound that localizes to a vacuole in a cell; (b) administering: (i) the drug candidate (ii) to the first sample for a time sufficient to allow the drug candidate to partition into subcellular compartments within the cells to form treated cells; and (ii) the vehicle or carrier (iii) to the second sample to form untreated reference cells; (c) contacting the treated cells and the untreated reference cells with the cationic amphiphilic tracer (iv) for a period of time sufficient to accumulate in vacuoles in the cells, and (d) detecting any increase in vacuole accumulation of the cationic amphiphilic tracer compound in the treated cells relative to said untreated reference cells, thereby determining whether said drug candidate has accumulated in the vacuoles and is toxic to cells, tissues or organs.

The present invention also provides a method of screening suspected toxic agents to determine their toxicity to cells, tissues or organs. In this method for screening suspected toxic agents for their toxicity, the following steps are carried out: (a) providing: (i) at least one first sample and one second sample of mammalian cells; (ii) a suspected toxic agent for screening; (iii) a diluting vehicle or carrier; and (iv) a cationic amphiphilic tracer compound that localizes to a vacuole in a cell; (b) administering (i) the suspected toxic agent (ii) to the first sample for a time sufficient to allow the suspected toxic agent to partition into subcellular compartments within the cells to form treated cells; and (ii) the diluting vehicle or carrier (iii) to the second sample to form untreated reference cells; (c) contacting the treated cells and the untreated reference cells with the cationic amphiphilic tracer (iv) for a period of time sufficient to accumulate in vacuoles in the cells, and (d) detecting any increase in vacuole accumulation of the cationic amphiphilic tracer compound in the treated cells relative to the untreated reference cells, thereby determining whether the suspected toxic agent has accumulated in the vacuoles and is toxic to cells, tissues or organs.

The present invention further provides a method of distinguishing between phospholipidosis activators and autophagy pathway perturbation agents. To distinguish such activators and agents, the following steps are carried out: (a) providing: (i) a fluorescent phospholipid analog compound that can incorporate into multilamellar vesicles; (ii) a cationic amphiphilic fluorophore tracer compound that localizes in a vacuole in a cell; (iii) a test agent; and (iv) a sample of mammalian cells; (b) administering to the cells in the sample (iv) the fluorescent phospholipid analog compound (i) and the test agent (iii) to form a testing mixture; (c) subsequently contacting the testing mixture with the cationic amphiphilic fluorophore tracer (ii); and (d) detecting any signals generated from the fluorescent phospholipid analog compound (i) and the cationic amphiphilic fluorophore tracer compound (ii), thereby differentiating between phospholipidosis activators and autophagy pathway perturbation agents based upon differential accumulation patterns of the fluorescent phospholipid analog and the cationic amphiphilic fluorophore tracer.

BRIEF DESCRIPTION OF THE FIGURES

FIG. 6: Fluorescent microscopy image (A.) and bright field image (B.) of cells stained with 5 µM Dye 2.

FIG. 8: Fluorescent microscopy image (A.) and bright field image (B.) of cells stained with 10 µM Dye 5.

DESCRIPTION OF THE INVENTION

Figure 1:
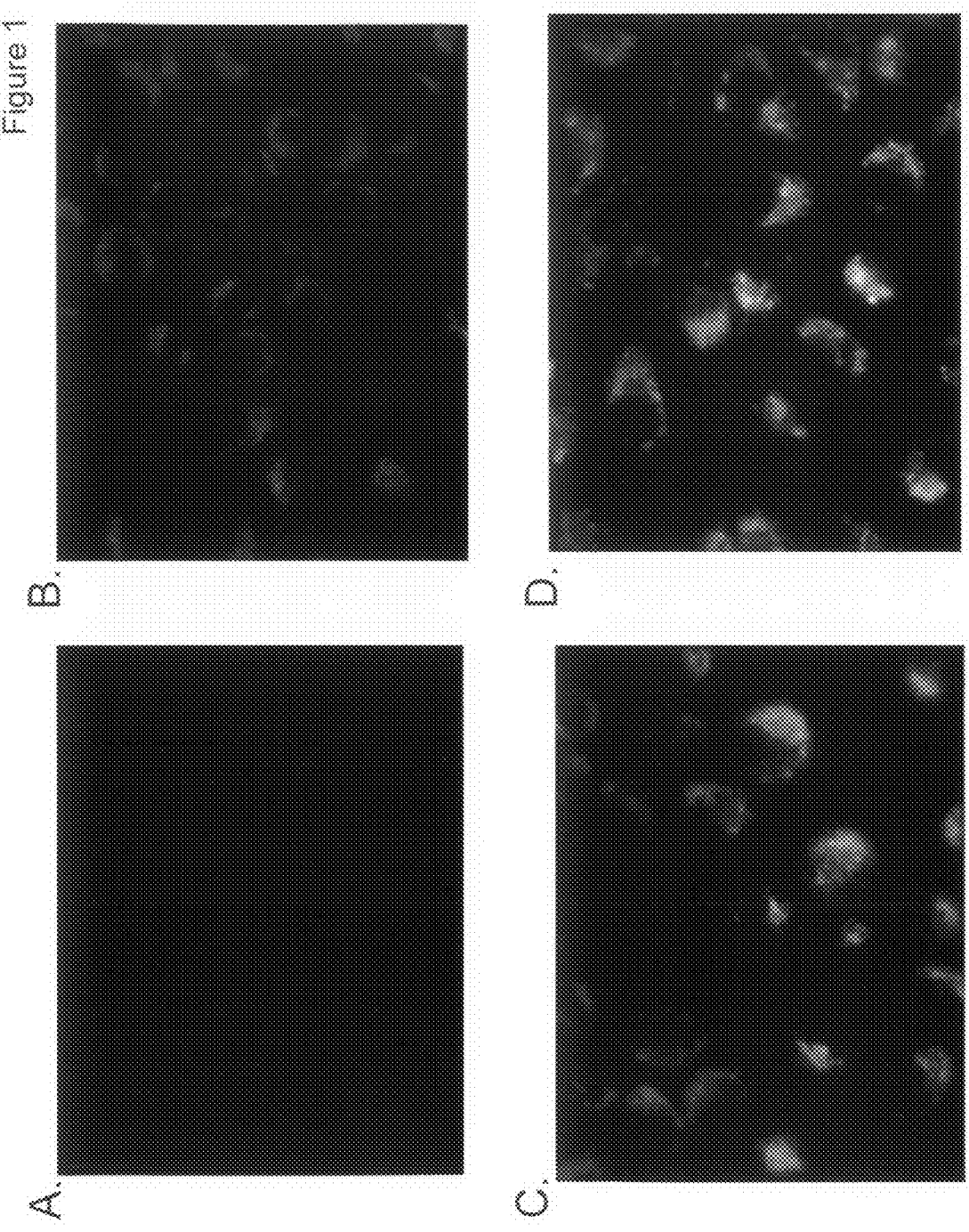
FIG. 1: Fluorescent microscopy images of cells treated with increasing doses of chloroquine.

The invention generally relates to an assay suitable for applications involving wide-field fluorescence microscopy, flow cytometry, confocal microscopy, fluorimetry, microplate-based cytometry, high-content cell analysis, cell microarray analysis, high-content cell screening, laser-scanning cytometry and other imaging and detection modalities. The invention relates to fluorescent probes that are selectively sequestered into vacuoles derived from the lysosome catabolic pathway. Without wishing to be bound by theory, it appears that through careful selection of titratable groups on the probe, labeling can be expanded into lamellar inclusion bodies of cells pre-treated with weakly basic, cell-permeant compounds, such as the anti-malarial drug chloroquine. The probes can be employed for highlighting lysosome-like organelles under conditions, wherein cells produce vacuoles that contain most of the degradative enzymes of the lysosome, but are not as acidic as the parent organelle. The assay measures generalized dysfunction of the lysosomal-dependent catabolic pathway, which leads to the accumulation of vacuoles such as autophagosomes, and thus is relevant to macroautophagy in general (herein referred to as autophagy), as well as to phospholipidosis in particular. One potential application of the new assay is in preclinical drug safety assessment (ADME-Tox) using in vitro cell culture models to aid in the drug development process.

Cationic drugs often exhibit large apparent volumes of distribution, which is consistent with various forms of sequestration within cells and tissues. This form of drug uptake can occur in intact cell types that are not necessarily specialized for the handling of xenobiotics. The drugs are sequestered into cells by a variety of metabolically-driven, but receptor-independent means including mitochondrial membrane potential-driven concentration, nuclear concentration via DNA affinity and vacuolar-ATPase-driven trapping into lysosomes that subsequently swell by an osmotic mechanism. Drug concentration within cells may arise from the innate membrane permeability of the uncharged forms of these drugs, as well as by means of specific transporters (organic cation transporters, choline transporters, etcetera). Such drug sequestration could contribute to overall toxicity, as well as prolong the duration of drug action. Fluorescence-based assays are disclosed that assess the impact of xenobiotics on overall cell function, with particular emphasis on the lysosomal and related compartments. In one embodiment, a semi-automated multi-well cell-based assay workflow is presented that provides a rapid and quantitative high-throughput approach for determining drug- or toxic agent-induced live cell response, offering throughput advantages relative to methods based upon electron microscopy, fluorescence microscopy or flow cytometry. Early secondary screening of candidate drugs for potentially adverse cell activity in the drug discovery phase could predict later risks in drug development arising from drug safety issues. Such a screening approach could aid in selecting the best candidate compounds for further drug development efforts, as well as provide preliminary benchmarking of dosing limits in preclinical toxicity studies.

DEFINITIONS

By fluorescence is meant the emission of light as a result of absorption of light-emission, occurring at a longer wavelength than the incident light.

By fluorophore is meant a component of a molecule which causes a molecule to be fluorescent.

By fluorochrome is meant any of a group of fluorescent dyes used to stain biological specimens.

By anthraquinone is meant the quinone derivative of anthracene, a tricyclic aromatic hydrocarbon containing two opposite carbonyl groups (C=O) at the 9, 10 positions of anthracene. These compounds may also be referred to as anthracenediones or as 9,10-dioxoanthracenes.

By autophagy is meant an evolutionarily conserved subcellular degradation process decomposing folded proteins, protein complexes and entire organelles, such as aggregates of misfolded proteins or damaged mitochondria, involving the inport of cytoplasmic components into the lysosome.

By xenobiotic is meant a compound or material foreign to the body of a living organism, including a chemical compound, such as a drug, toxin or pesticide, or a material, such as a particle, nanoparticle, nanocrystal or fiber.

By cationic amphiphilic tracer compound is meant a member of a class of compounds sharing common physiochemical properties: hydrophobic ring structure on the molecule and a hydrophilic side chain with a charged cationic amine group. The cationic amphiphilic tracer compounds of the present invention generally localize to a vacuole of a cell within about one hour.

By phospholipidosis is meant an excessive accumulation of intracellular phospholipids in cells and tissues triggered by a cationic amphiphilic drug or an inborn error of lipid metabolism (lysosomal storage disease).

By lysosomal storage disease is meant any one of a group of approximately 40 or so rare inherited metabolic disorders that result from defects in lysosomal function. Lysosomal storage diseases are characterized by a congenital or acquired deficiency of an enzyme so that one or more specific metabolic processes are not completed. As a result there is an accumulation of metabolic products in the cellular lysosomes. The following is a list of known lysosomal storage diseases: Activator deficiency/GM2 gangliosidosis, Alpha-mannosidosis, Aspartylglucosaminuria, Cholesteryl ester storage disease, Chronic hexosaminidase A deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders, Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV, Multiple sulfatase deficiency, Niemann-Pick Disease, Neuronal Ceroid Lipofuscinoses, CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff disease/Adult Onset/GM2 Gangliosidosis, Sandhoff disease/GM2 gangliosidosis—Infantile. Sandhoff disease/GM2 gangliosidosis—Juvenile, Schindler disease, Salla disease/Sialic Acid Storage Disease, Tay-Sachs/GM2 gangliosidosis and Wolman disease."

By metachromasy is meant the hypsochromic (shift in absorption to shorter wavelength) and hypochromic (decrease in intensity of emitted fluorescence) change in color exhibited by certain dyes in aqueous-based media under conditions such as: (1), increase in dye concentration; (2), temperature decrease; (3), salting out; and (4), interaction with substrates that favor water intercalation and/or proximity or stacking of dye monomers.

Basic Fluorophore Core Structures:

The present invention pertains to the preparation and use of fluorescent cationic amphiphillic tracers comprising polycyclic fused ring systems, such as anthraquinone, anthrapyrazole, and benzophenoxazine fluorophores in cell imaging and detection. Also included in this patent are styryl cyanine dyes and acridine derivatives that are conjugated to amphiphillic moieties such as propranolol. Generally, these types of dyes are electrically neutral and lipophilic, properties which permit them to be better solubilized in non-polar environments, such as cell membranes thereby rendering them cell permeable. More particularly, the invention relates to modifications of these dyes with functional groups that target the dyes to lysosomes and related vacuolar organelles. In one embodiment of the present invention, the functional groups attached to the dyes do not have a propensity for vacuolar organelles in and of themselves, but their addition to a dye endows the modified dye with such properties. In another embodiment of the present invention, functional groups are added that intrinsically have their own affinity for this particular class of organelles and the addition of such groups to a dye conveys this property to the dye. Such tracer compounds, dyes, derivatives, modifications and functional groups are described in related U.S. patent applications Ser. No. 12/287,882 (filed Oct. 13, 2008) and Ser. No. 12/231,988 (filed Sep. 8, 2008), the contents of both incorporated by reference herein.

This invention provides compositions and methods for identifying catabolic pathway-derived organelles and related cellular structures and elements. Specifically, the present invention provides compounds and methods for measuring generalized dysfunction of the lysosomal-dependent catabolic pathway, which leads to the intracellular accumulation of vacuoles, such as autophagosomes, phagophores or autophagolysosomes. The compounds and methods further allow identification of xenobiotics that interfere with membrane trafficking during autophagy as well as those that induce the phenomenon of phospholipidosis.

The invention discloses compositions comprising cationic amphiphilic fluorophore tracers that are capable of partitioning into vacuoles arising from generalized dysfunction of the lysosomal-dependent catabolic pathway.

The invention further discloses methods for identifying the intracellular accumulation of vacuoles within cells of interest comprising the steps of (A) providing (i) the cells of interest; (ii) any xenobiotic agent (iii) any of the compositions described herein below; (B) incubating the cells of interest (i) with a xenobiotic agent (ii); subsequently incubating cells of interest (i) with any composition (iii) and (C) monitoring the accumulation of the composition (iii) within the cells.

Other aspects and embodiments are described in further detail below.

The present invention provides a dye having the formula:

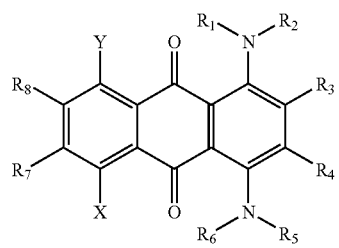

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$, $R_2$, $R_5$ and $R_6$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), it thioanalogue ($PSNR_{11}R_{12}NR_{13}NR_{14}R_{15}$), a phosphoramidite ($PO_2R_{14}NR_{11}R_{12}$) thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

In another aspect of the present invention, novel dyes that are based upon styryl dyes are disclosed. In one embodiment the dyes have the general structure:

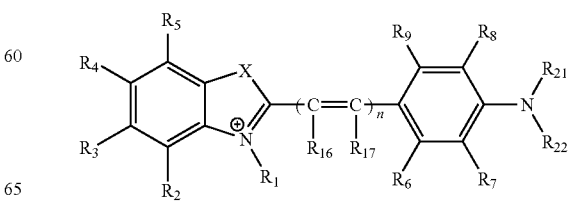

wherein X comprises $CR_{11}R_{12}$, $NR_{11}$, O, S or Se where $R_{11}$ and $R_{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R_{11}$ and $R_{12}$ form a 5 or 6 membered ring;

wherein n can be 1, 2 or 3;

wherein at least one of of $R_1$, $R_2$, $R_3$, $R_4$, $R_5$, $R_6$, $R_7$, $R_8$, $R_9$, $R_{11}$, $R_{12}$ comprises Q, wherein Q comprises a sulfoxide ($SOR_{13}$), a sulfone ($SO_2CR_{13}R_{14}R_{15}$), a sulfonamide ($SO_2NR_{13}R_{14}$), a phosphonate ($PO_3$), a phosphonate monoester ($PO_2^-ER_{13}$) a phosphonate diester ($POER_{13}ER_{14}$), a thiophosphate ($PSO_3^-$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) wherein any of E can independently comprise O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q(2) is a sulfonamide, it does not comprise a terminal reactive group or a linker joining the dye to a target molecule;

wherein $R_{13}$, $R_{14}$, $R_{15}$, $R_{19}$ and $R_{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R_{13}$ and $R_{14}$ form a five or six membered ring;

wherein $R_{16}$, $R_{17}$ and the remaining $R_1$, $R_2$, $R_3$, $R_4$, $R_5$, $R_6$, $R_7$, $R_8$, $R_9$, $R_{11}$, $R_{12}$, $R_{16}$, $R_{17}$, $R_{21}$ and $R_{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R_2$ and $R_3$, $R_3$ and $R_4$, $R_4$ and $R_5$, $R_6$ and $R_7$, $R_7$ and $R_8$, $R_1$ and $R_{16}$, $R_{11}$ and $R_{16}$, $R_{16}$ and $R_{17}$, $R_{17}$ and $R_{18}$, and $R_{18}$ and $R_9$ may form a 5 or 6 membered ring;

wherein Z comprises a carboxyl group ($CO_2^-$), an alkyl amino, a carbonate ester ($COER_{13}$), a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^-$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R_1$, $R_2$, $R_3$, $R_4$, $R_5$, $R_6$, $R_7$, $R_8$, $R_9$, $R_{11}$, $R_{12}$, $R_{21}$ or $R_{22}$ may further comprise a heteroatom containing side chain wherein said side chain is joined to the R group by a linkage which comprises an ether linkage (—$OR_{25}$), a thioether linkage (—$SR_{25}$), or an amine linkage (—$NR_{25}R_{26}$ or —$N^+R_{25}R_{26}R_{27}$), and wherein $R_{25}$, $R_{26}$ and $R_{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R_{25}$ and $R_{26}$, and $R_{26}$ and $R_{27}$ independently comprise a five or six membered ring, and wherein any of $R_{25}$, $R_{26}$ or $R_{27}$ may further comprise said heteroatom containing side chain.

In another embodiment of the present invention, the styryl dye comprises a picoline or quinoline moiety instead of a benzazolium group. As such, these dyes have the structure:

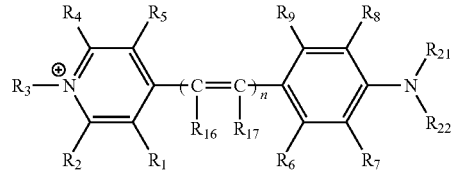

wherein n can be 1, 2 or 3;

wherein at least one of $R_1$, $R_2$, $R_3$, $R_4$, $R_5$, $R_6$, $R_7$, $R_8$, $R_9$, $R_{21}$ or $R_{22}$ comprises Q wherein Q comprises a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^-$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, it does not comprise a terminal reactive group or a linker joining the dye to a target molecule;

wherein $R_{13}$, $R_{14}$, $R_{15}$, $R_{19}$ and $R_{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R_{13}$ and $R_{14}$ form a five or six membered ring;

wherein $R_{16}$, $R_{17}$ and the remaining $R_1$, $R_2$, $R_3$, $R_4$, $R_5$, $R_6$, $R_7$, $R_8$, $R_9$, $R_{21}$ or $R_{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R_1$ and $R_2$, $R_2$ and $R_3$, $R_3$ and $R_4$, $R_4$ and $R_5$, $R_5$ and $R_{16}$, $R_{16}$ and $R_{17}$, $R_{17}$ and $R_9$, $R_9$ and $R_8$, $R_8$ and $R_{21}$, $R_{21}$ and $R_{22}$ and $R_7$, and $R_7$ and $R_6$ may form a 5 or 6 membered ring;

wherein Z comprises a carboxyl group ($CO_2^-$), a carbonate ester ($COER_{13}$), a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^=$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R_1$, $R_2$, $R_3$, $R_4$, $R_5$, $R_6$, $R_7$, $R_8$, $R_9$, $R_{21}$ or $R_{22}$ may further comprise a heteroatom containing side chain wherein said side chain is joined to the R group by a linkage which comprises an ether linkage ($-OR_{25}$), a thioether linkage ($-SR_{25}$), or an amine linkage ($-NR_{25}R_{26}$ or $-N^+R_{25}R_{26}R_{27}$), and wherein $R_{25}$, $R_{26}$ and $R_{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R_{25}$ and $R_{26}$, and $R_{26}$ and $R_{27}$ independently comprise a five or six membered ring, and wherein any of $R_{25}$, $R_{26}$ or $R_{27}$ may further comprise said heteroatom containing side chain.

When $R_4$ and $R_5$ comprise alkyl chains that are joined together, a quinoline moiety can be formed, the dye thereby having the general structure:

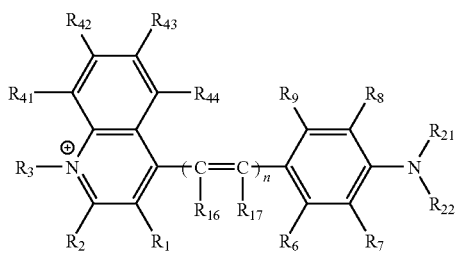

where $R_{41}$, $R_{42}$, $R_{43}$ and $R_{44}$ are as described previously for $R_1$, $R_2$, $R_3$, $R_4$, $R_5$, $R_6$, $R_7$, $R_8$, $R_9$, $R_{21}$ and $R_{22}$.

In yet another embodiment of the present invention, the styryl dye comprises a 2-picoline or quinaldine moiety instead of a benzazolium group. As such, these dyes have the structure:

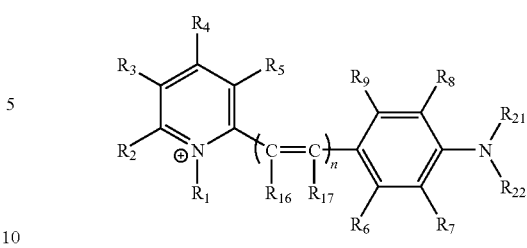

wherein n can be 1, 2 or 3;

wherein at least one of $R_1$, $R_2$, $R_3$, $R_4$, $R_5$, $R_6$, $R_7$, $R_8$, $R_9$, $R_{21}$ or $R_{22}$ comprises Q wherein Q comprises a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^=$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, it does not comprise a terminal reactive group or a linker joining the dye to a target molecule;

wherein $R_{13}$, $R_{14}$, $R_{15}$, $R_{19}$ and $R_{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R_{13}$ and $R_{14}$ form a five or six membered ring;

wherein $R_{16}$, $R_{17}$ and the remaining $R_1$, $R_2$, $R_3$, $R_4$, $R_5$, $R_6$, $R_7$, $R_8$, $R_9$, $R_{21}$ or $R_{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R_1$ and $R_2$, $R_2$ and $R_3$, $R_3$ and $R_4$, $R_4$ and $R_5$, $R_5$ and $R_{16}$, $R_{16}$ and $R_{17}$, $R_{17}$ and $R_9$, $R_9$ and $R_8$, $R_8$ and $R_{21}$, $R_{21}$ and $R_{22}$, $R_{22}$ and $R_7$, and $R_7$ and $R_6$ may form a 5 or 6 membered ring;

wherein Z comprises a carboxyl group ($CO_2^-$), a carbonate ester ($COER_{13}$), a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^=$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue (PSNR$_{13}$R$_{14}$NR$_{15}$NR$_{19}$R$_{20}$), a phosphoramidite (PO$_2$R$_{19}$NR$_{13}$R$_{14}$) or its thioanalogue (POSR$_{19}$NR$_{13}$R$_{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of R$_1$, R$_2$, R$_3$, R$_4$, R$_5$, R$_6$, R$_7$, R$_8$, R$_9$, R$_{21}$ or R$_{22}$ may further comprise a heteroatom containing side chain wherein said side chain is joined to the R group by a linkage which comprises an ether linkage (—OR$_{25}$), a thioether linkage (—SR$_{25}$), or an amine linkage (—NR$_{25}$R$_{26}$ or —N$^+$R$_{25}$R$_{26}$R$_{27}$), and wherein R$_{25}$, R$_{26}$ and R$_{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$_{25}$ and R$_{26}$, and R$_{26}$ and R$_{27}$ independently comprise a five or six membered ring, and wherein any of R$_{25}$, R$_{26}$ or R$_{27}$ may further comprise said heteroatom containing side chain.

When R$_2$ and R$_3$ comprise alkyl chains that are joined together, a quinaldine moiety can be formed, the dye thereby having the general structure:

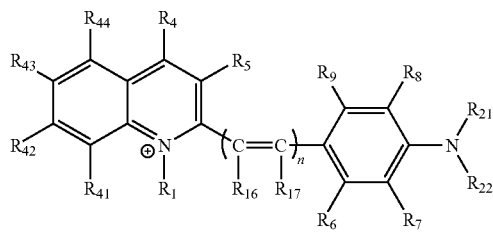

where R$_{41}$, R$_{42}$, R$_{43}$ and R$_{44}$ are as described previously for R$_1$, R$_2$, R$_3$, R$_4$, R$_5$, R$_6$, R$_7$, R$_8$, R$_9$, R$_{21}$ and R$_{22}$.

Complex Ring Structures

As described above some of the R groups may be joined together to form one or more fused 5 or 6 membered ring structures. It is understood that the complex rings that are formed by closure of R groups may be further substituted with any of the R groups described previously. Examples of complex rings that may be formed for the benzazolium portion of cyanine and asymmetric cyanine dyes can comprise but not be limited to:

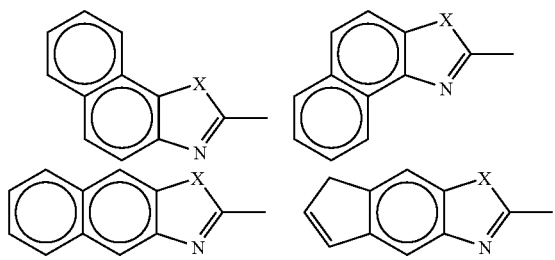

In addition, "rigid" cyanine dyes have been described wherein a fused ring is formed where the nitrogen of the benzazolium is linked to the nearest carbon of the methine bridge (U.S. Pat. No. 6,133,445 and U.S. Pat. No. 6,686,145 both of which are hereby incorporated by reference). Similarly in a cyanine dye with a monomethine bridge (i.e. when n=0), a rigid linkage can be formed by joining the nitrogens of the benzazolium group to each other (U.S. Pat. No. 5,852,191 and U.S. Pat. No. 5,981,747 both of which are incorporated by reference).

If desired, a variation of the preceding dyes can be the substitution of an azabenzazolium instead of a benzazolium moiety in the cyanine, asymmetric cyanine and styrene dyes; i.e. a Nitrogen replaces the carbon in the positions where R$^2$, R$^3$, R$^4$, R$^5$, R$^7$, R$^8$, R$^9$ or R$^{19}$ are connected to the benzazolium moiety of cyanine dyes or to the R$^2$, R$^3$, R$^4$ or R$^5$ positions of the asymmetric cyanine and styrene dyes disclosed previously. Methods for the synthesis and use of an azabenzazolium based dyes are disclosed in U.S. Pat. No. 6,664,047 B1, hereby incorporated by reference. As such these moieties would have the structures:

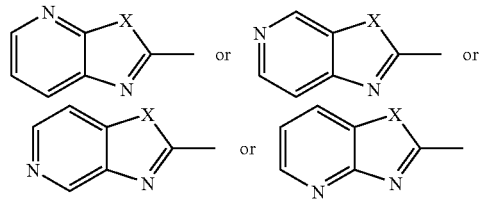

Examples of rings and complex rings that may comprise the non-benzazolium portion of an asymmetric cyanine dye can comprise but not be limited to:

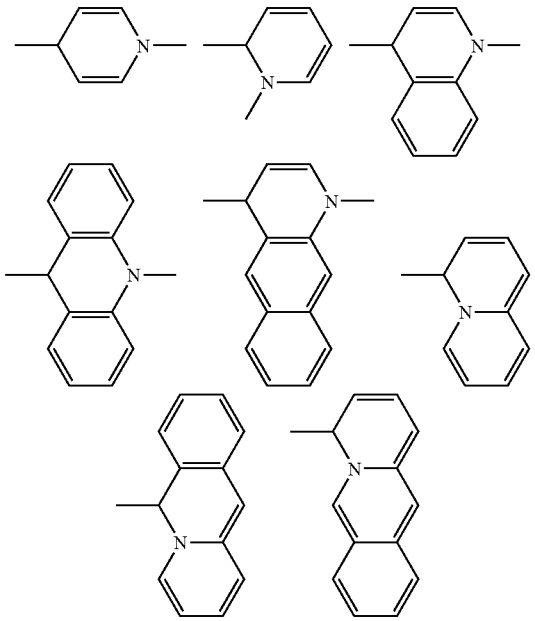

Examples of rings and complex rings that may be part of the non-benzazolium portion of a styryl dye can comprise but not be limited to:

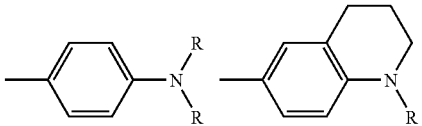

-continued

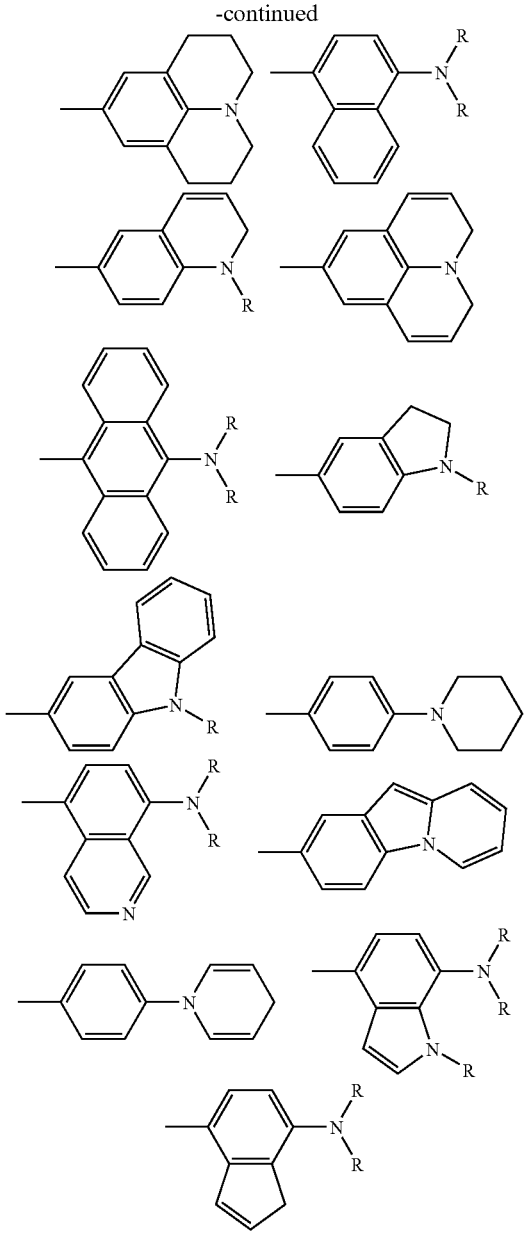

Reactive Groups and Targets

In another aspect of the present invention, one of the R groups is a reactive group thereby allowing the dyes of the present invention to be attached to a useful target molecule. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use with the present invention; examples can include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group. Use of a terminal alkene or alkyne groups for attachment of markers has been previously described in U.S. Patent Application Serial No. 2003/0225247, hereby incorporated by reference. The use of platinum coordinate groups for attachment of other dyes has been previously disclosed in U.S. Pat. No. 5,580,990 and the use of alkyl groups has been previously described in U.S. Pat. No. 6,593,465 B1, both of which patents are hereby incorporated by reference.

Examples of useful target molecules can include but not be limited to a cationic amphiphilic drugs, nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, liposomes, glycolipid, viral particle, viral component, bacterial cell, bacterial component, eucaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof.

Specific examples of cationic amphiphilic drugs includes but not limited to Propranolol, Chloroquine, Chlorpromazine, Gentamicin, Chlorphentermine, AY9944, Amiodarone, Fluoxetine, Imipramine, Chlorcyclizine and Tamoxifen. Structures of some of these drugs are shown below:

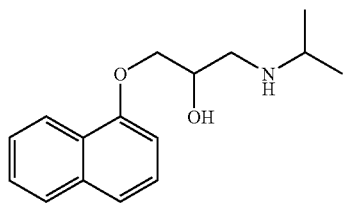
Propranolol

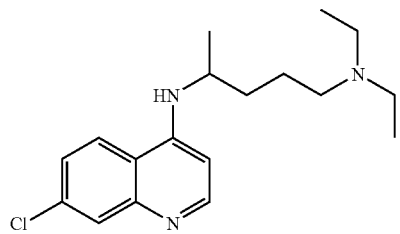
Chloroquine

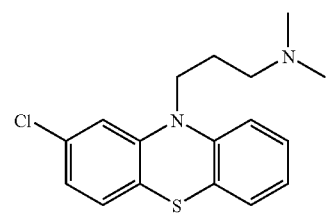
Chlorpromazine

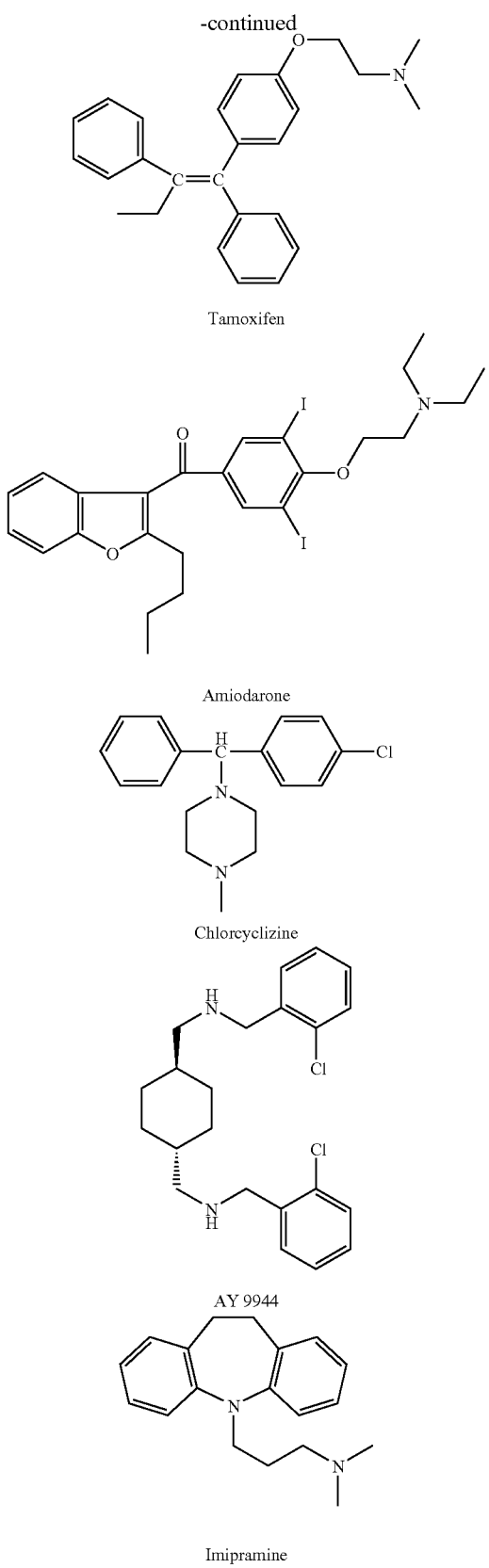

The nucleoside, nucleotide, oligonucleotide, or polynucleotide can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues and any combination thereof.

As described above, the dyes of the present invention may have dyes as targets thereby creating composite dyes. By joining the dyes of the present invention to another dye, unique properties may be enjoyed that are not present in either dye alone. For instance, if one of the dyes of the present invention is joined to another dye such that it creates an extended conjugation system, the spectral characteristics of the dye may be different than either dye component. Another example of this method is where the conjugation systems do not overlap but the proximity allows an internal energy transfer to take place thereby extending the Stokes shift. For an example of this, see U.S. Pat. No. 5,401,847, U.S. Pat. No. 6,008,373 B1 and U.S. Pat. No. 5,800,996, all three of which patents are hereby incorporated by reference. Other properties may also be enhance by this joining, for example, it has been previously described that the joining together of two ethidium bromide molecules generates a dye that has enhanced binding to nucleic acids (U.S. Patent Application Publication No. 2003/0225247, hereby incorporated by reference). Other composite dyes have been described that simultaneously enjoy both properties, i.e. enhanced binding and energy transfer (U.S. Pat. No. 5,646,264, hereby incorporated by reference). Furthermore, these composites dyes are not limited to binary constructs of only two dyes, but may comprise oligomeric or polymeric dyes. These composite dyes may be comprised of the same dye or different dyes may be joined together depending upon the properties desired.

Utility may also be achieved by attaching a dye of the present invention to a target specific moiety. Thus, binding between the target specific moiety and its corresponding target may be monitored by essentially determining the presence or amount of dye that is bound to the target. Well-known examples of such assays are hybridizations between complementary nucleic acids as well as binding that take place between antibodies and their corresponding antigens. Other binding pairs that may be of interest can include but not be limited to ligand/receptor, hormone/hormone receptor, carbohydrate/lectin and enzyme/substrate. Assays may be carried out where one component is fixed to a solid support and a corresponding partner is in solution. By binding to the component fixed to the support, the partner now becomes attached to the support as well. A well-known example of this method is the microarray assays where labeled analytes become bound to discrete sites on the microarray. Homogeneous probe dependent assays are also well known in the art and may take advantage of the present invention. Examples of such methods are energy transfer between adjacent probes (U.S. Pat. No. 4,868,103), the Taqman exonuclease assay (U.S. Pat. No. 5,538,848 and U.S. Pat. No. 5,210,015), Molecular Beacons (U.S. Pat. No. 5,118,801 and U.S. Pat. No. 5,925,517) and various real time assays (U.S. patent application Ser. No. 10/096,076), all of which are incorporated by reference.

Various applications may enjoy the benefits of binding the dyes of the present invention to appropriate targets. As described above, staining of macromolecules in a gel is a methodology that has a long history of use. More recent applications that also may find use are real time detection of amplification (U.S. Pat. No. 5,994,056, U.S. Pat. No. 6,174,670 and U.S. patent application Ser. No. 10/096,076, all of which are hereby incorporated by reference), and binding of nucleic acids to microarrays. In situ assays may also find use where the binding of dyes of the present invention is used to identify the location or quantity of appropriate targets.

Amphiphilic compounds containing a cationic (aka basic) moiety often accumulate in lysosomes or other acidic subcellular compartments. This lysosomotropism is thought to be due to the protonation of the dye within acidic organelles leading to the formation of a membrane-impermeable form. Highly lipophilic dyes show a greater propensity to accumulate in lysosomes than those with a lower lipophilicity.

Some generalilzed approaches for identifying dyes that statically accumulate in lysosomes have previously been reported (Rashid, et al, 1991). While these guidelines for creating lysome-targeting probes are known, the basis of the selectivity of specific fluorochromes for this group of subcellular organelles in live cells is sometimes elusive. To clarify this, interactions of living cells with series of different probe molecules, having systematically varied physicochemical properties, should be analyzed experimentally and numerically using approaches such as quantitative structure activity relationship analysis (QSAR) and Fick-Nernst-Planck analysis. Typically, a single cell line or a panel of cell lines is incubated with different concentrations (typically 1-100 µM) of the potential vacuole-targeting compounds and subcellular distribution is monitored by wide-field fluorescence microscopy. Combinatorial synthesis of panels of dye derivatives may be subjected to cell-based screening in order to identify lead compounds with desired localization properties. The lysosome probes described in the literature tend to dissipate upon treatment of cells with drugs and agents that impinge upon the lysosomal catabolic pathways, rendering them unsuitable for xenobiotic screening in any dynamic context. Identification of probes that encompass both unperturbed and perturbed states requires screening both control cells and cells treated with a perturbing agent, such as propranolol, triparanol, chlorpromazine, chloroquine, fluoxetine, clindamycin, ketoconazole or bafilomycin A.

Dyes Conjugated to Organelle Specific Moieties

In another embodiment of the present invention, we have found that the combination of nuclear dye with a moiety that has an affinity for the lysosome can result in a conjugate that retains the ability to target the lysosomal organelle and endowing it with the spectral properties of the dye. It has been found that a variety of subcellular organelle, region or domain targeting functional groups may be covalently affixed to a fluorophore core. Typically, either one or two such functional groups are affixed to the core structure, though in certain circumstances as many as four such groups can potentially be affixed to the fluorophore core. These are non-limiting examples of targeting groups that may find use with the present invention by being conjugated to an anthraquinone, anthrapyrazole or benzophenoxazine. Another important example is the conjugation of a fluorophore to a cationic amphillic drug, such as propranolol, triparanol, chlorpromazine, chloroquine, fluoxetine, clindamycin, ketoconazole. Halogenated analogs of these drugs are especially suitable when compared to nonhalogenated analogs for profiling the lysosomal catabolic pathway. Without wishing to be bound by theory, this appears to be due to a stronger affinity of halogenated analogs for the lysosome and lysosome-related compartments.

Detecting Lysosomal Storage Diseases

Because the cationic amphiphlic tracer compounds exhibit specificity in localizing to cellular vacuoles, the present invention is particularly well suited for detecting the presence of a lysosomal storage disease in a subject or patient. For a good review of lysosomal disorders and lysosomal storage diseases, see Ballabio and Gieselmann, *Biochimica et Biophysica Acta* 1793:684-696 (2009), incorporated herein by reference.

Briefly, the method for detecting lysosomal storage diseases is carried out by (a) obtaining a sample containing cells from the subject or patient followed by (b) contacting the sample with a cationic amphiphilic tracer compound that localizes to a vacuole in a cell. By next (c) detecting the cationic amphiphilic tracer compound, it can be determined whether there exists an excess above normal accumulation of vacuoles within the cells of the sample. Such an excess above normal accumulation of vacuoles is indicative of the lysosomal storage disease.

The lysosomal storage disease sought to be detected can arise from deficiencies of one or more soluble lysosomal proteins residing in the lumen of the lysosome. Such storage diseases can also arise from a defect in one or more lysosomal membrane proteins. Further, these lysosomal storage disease can arise from deficiencies of non-lysosomal proteins residing in a site comprising an endoplasmic reticulum, a Golgi apparatus or an endosomal pathway, as well as combinations of any of the foregoing. In other instances, the lysosomal storage disease may comprise a mucopolysaccharidoses, a lipidoses or a glycogenosis. Moreover, this method is applicable to a subject is known to have a lysosomal storage disease based upon previous genetic or metabolic testing. A list of lysosomal storage diseases have been provided in the above definition of lysosomal storage disease.

As discussed above, the cationic amphiphilic tracer compound provides for specific localization in vacuoles of cells. Such vacuoles include, for example, lysosomes, phagophores, autophagosomes or autophagolysosomes, and combinations of the foregoing. The cationic amphiphilic tracer compound can comprise a fluorescent drug that induces phospholipidosis or a fluorescently labeled analog of a drug that induces phospholipidosis. The cationic amphiphilic tracer compound can also comprise a halogenated and fluorescent drug that induces phospholipidosis or a halogenated and fluorescently labeled analog of a drug that induces phospholipidosis. Among useful cationic amphiphilic tracer compound of the present invention are those which comprise nitrobenzoxadiazole (NBD)-spiperone, nitrobenzoxadiazole (NBD)-propranolol, or 9-amino-acridin-propanolol, and combinations of any of the foregoing.

Of particular interest in the present invention are cationic amphiphilic tracer compound having any of the following structures:

23  24
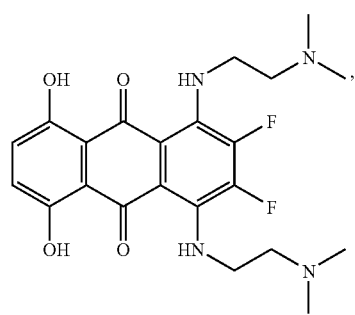 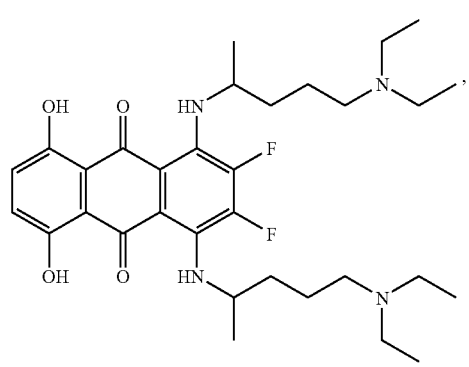
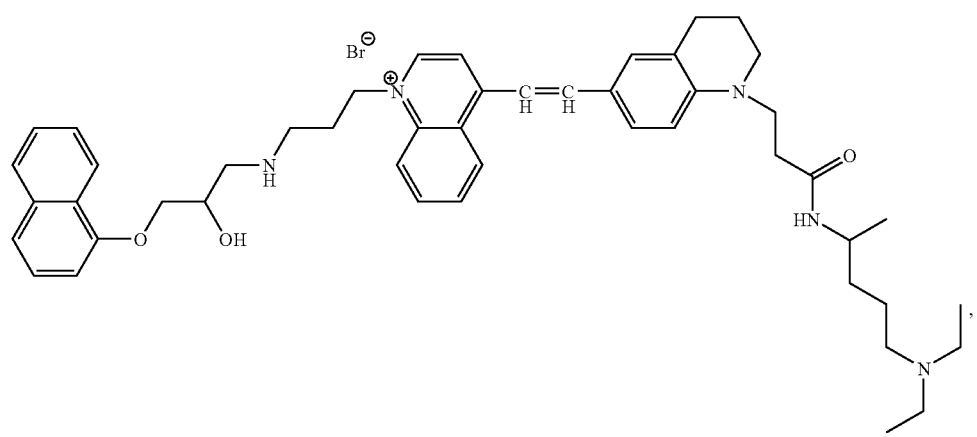
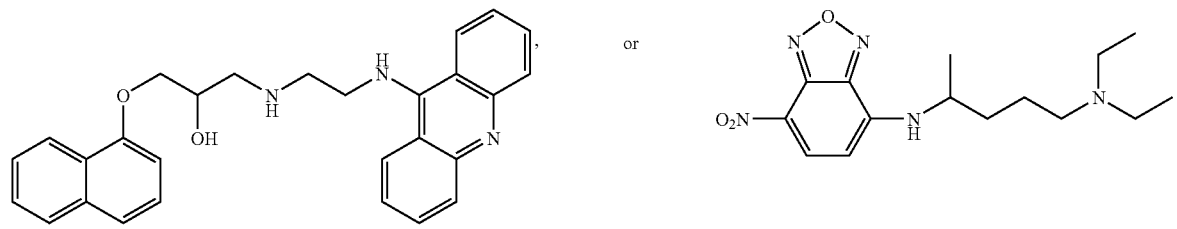
Particularly well suited for detecting lysosomal storage diseases are compound dyes having the structures:
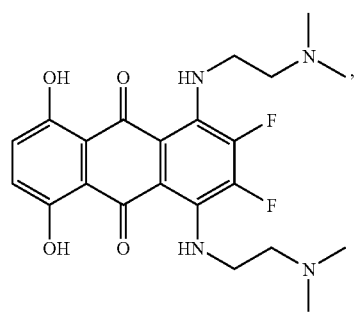

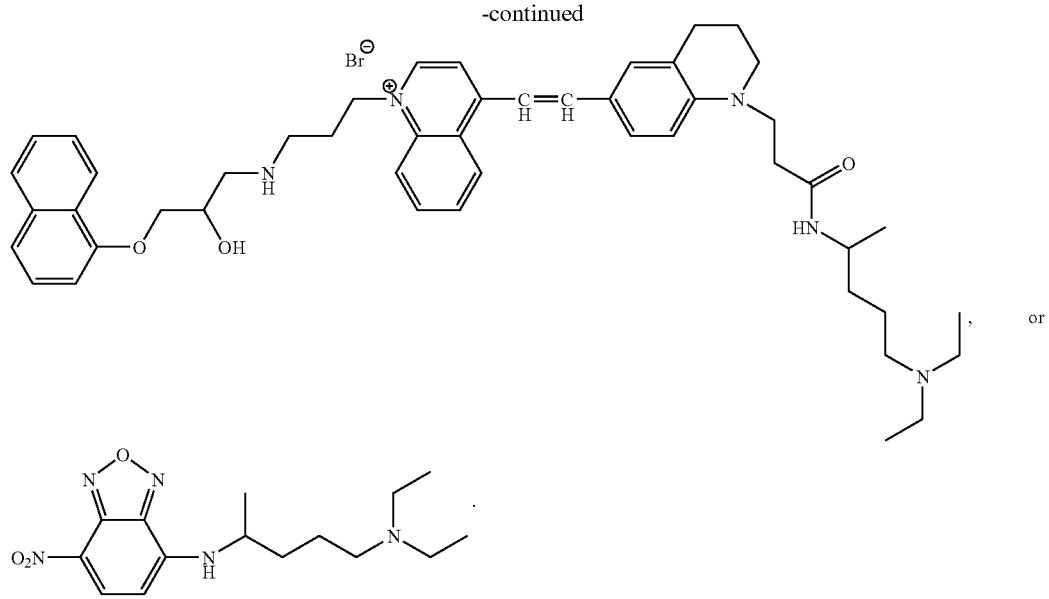

The above detection method can also be modified by providing a reference sample of normal cells from a subject or patient who is known not to have a lysosomal storage disease. Thus, the above-described method would further comprise the following steps (a') of providing a reference sample of normal cells from a subject known not to have lysosomal storage disease; (b') contacting the sample of normal cells with the same cationic amphiphilic tracer compound of step (b); and (c') comparing the accumulation of vacuoles in the sample obtained from the subject known or suspected of having a lysosomal storage disease with the accumulation in the reference sample of normal cells.

The cells which are contained in the sample obtained from a subject or patient can comprise lymphocytes, granulocytes, macrophages or monocytes and combinations of any or all of these. The subject may be a mammal which may be human.

Formulations and Compositions

Compositions according to the invention comprise a compound of the invention and are intended to include any and all solvents, dispersion media, coatings, isotonic and absorption delaying agents, and the like, compatible with the application. Except insofar as any conventional media or agent is compatible with the active compound, such media can be used in the compositions of the invention. Supplementary active compounds can also be incorporated into the compositions.

For example, when a composition of the invention is applied to cells or tissues, it is formulated to be compatible with the intended route of entry into the cells or tissues. For example, isotonic saline solutions, mildly hypertonic saline solutions, phosphate-buffered saline, cell culture media, isotonic sucrose solutions, or mildly hypertonic sucrose solutions may serve as the vehicle for delivery of the compound to the cells. Polyethylene glycols, glycerin, dimethylsulfoxide, dimethylformamide, propylene glycol, or other co-solvents may be included to facilitate solubilization of the compound. Antibaterial agents, such as benzyl alcohol or methyl parabens; antioxidants, such as ascorbic acid or sodium bisulfite; chelating agents, such as ethylenediaminetetraacetic acid (EDTA) or cyclodextrin; buffers, such as acetates, phosphates or citrates; agents for adjusting tonicity, such as sodium chloride or sucrose; and agents that adjust the pH value of the delivery vehicle, such as sodium hydroxide and hydrochloric acid may be incorporated in the formulation of the compound.

Compositions of the said invention may include certain anions and cations (e.g. alkyl metal chlorides) to facilitate penetration of the compound thru cell membranes. Non-limiting examples of anions include barbital, bicarbonate, borate, chloride, oxylate or EDTA. Not all anions have been found suitable for promoting penetration of cell membranes. Non-limiting examples of cations include sodium (as in sodium chloride), potassium (as in potassium chloride), trishydroxymethylamino methane (TRIS), tris [hydroxymethyl]-aminomethane-hydrochloric acid (TRIS-HCL), or triethanolamine (TEA).

Reagent Kits:

Commercial kits are valuable because they eliminate the need for individual laboratories to optimize procedures, saving both time and resources. They also allow better cross-comparison of results generated from different laboratories. The present invention additionally provides reagent kits, i.e., reagent combinations or means, comprising all of the essential elements required to conduct a desired assay method. The reagent system is presented in a commercially packaged form, as a composition or admixture where the compatibility of the reagents will allow, in a test kit, i.e., a packaged combination of one or more containers, devices or the like holding the necessary reagents, and usually written instructions for the performance of the assays. Reagent systems of the present invention include all configurations and compositions for performing the various labeling and staining formats described herein.

The reagent system will generally comprise (1.) one or more fluorochrome designed to target the lysosome and/or related organelles organelles. (2.) Instructions for usage of the included reagents. Generic instruction, as well as specific instructions for the use of the reagents on particular instruments, such as a wide-field microscope, confocal microscope, flow cytometer or microplate-based detection platform may be provided. Recommendations regarding filter sets and/or illumination sources for optimal performance of the reagents for a particular application may be provided.

A test kit form of the system for detecting xenobiotics that modify the lysosomal-dependent catabolic pathway, for example, can contain one or more substituted anthraquinone, phenoxazines, anthrapyrazole or benzophenoxazine fluorochromes that localize to the lysosome, and additional ancillary chemicals, such as dilution buffer, live-cell DNA stain, live-cell mitochondrial stain and/or an antibody, a lectin, a $Ca^{2+}$-dependent, phospholipid binding protein (such as Annexin V), or other reporter labeled with a fluorophore. In some instances one or more fluorochrome may be combined within a single container for easier use. In some instances, calibrants are included, such as microsphere or bead standards of known fluorescent output.

Phenotypic Monitoring of the Progression Lysosomal Storage Diseases

Often with inherited lysomal storage diseases, there is no strict correlation between disease-causing genetic mutations and the severity of clinical phenotype. For example, in Nieman-Pick disease, some patients develop severe neurological symptoms during the first two years of life. These patients demonstrate delayed motor development and hypotonia. They typically die within their first five years of life. More commonly, patients exhibit first symptoms between the ages of 3 and 15 years, often first noted as a loss of speech and increasing clumsiness. Neurological symptoms may progress to include cerebellar ataxia, dysarthia, dysphagia, cataplexy, seizures, dystonia, vertical gaze palsy and dementia. These patients usually die by 8 to 15 years of age. Adult onset cases of the disease have also been documented, usually occurring in the patient's twenties or thirties, though occasionally as late as in their mid-sixties. These patients develop similar symptoms to the classical; form of juvenile Nieman-Pick disease and often expire in their 30's and 40's. Though there are currently no effective treatments for Nieman-Pick and many of the other lysosomal storage diseases, it is recognized that the described assays hold promise in the routine phenotypic assessment of lysosomal dysfunction in patients, which could eventually lead to appropriate therapeutic intervention prior to neurological compromise.

Selected embodiments of the compounds of this invention include but are not limited to following:

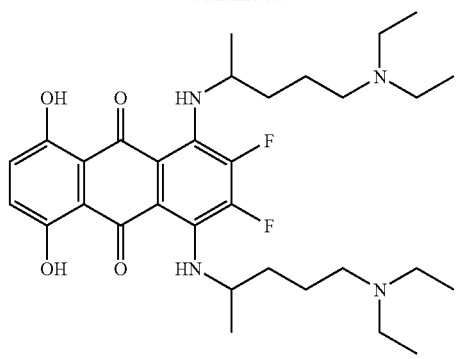

wherein X comprises an anion.
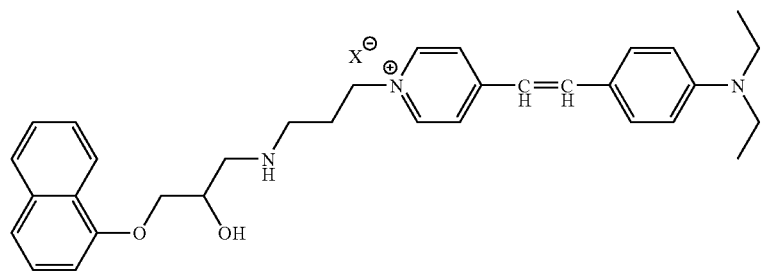 [SMILES: CCN(CC)c1ccc(C=Cc2cc[n+](CCCNCC(O)COc3cccc4ccccc34)cc2)cc1]
wherein X comprises an anion.
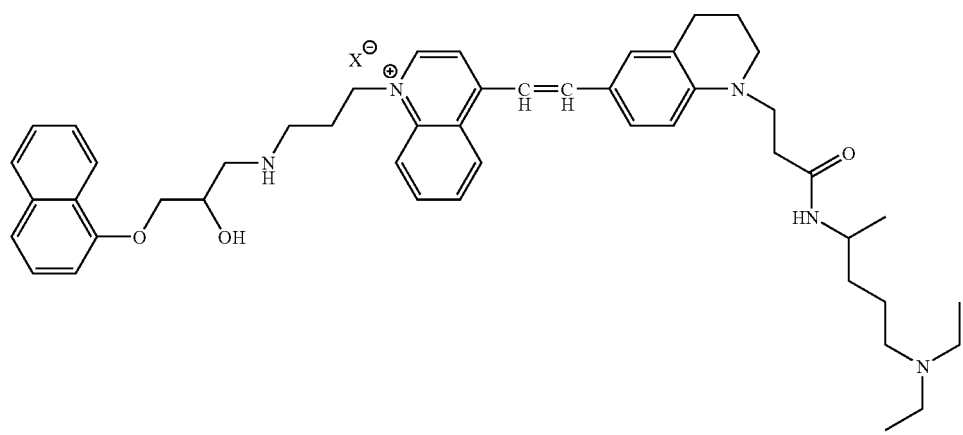 [SMILES: CCN(CC)CCCC(C)NC(=O)CCN1CCCc2cc(C=Cc3cc[n+](CCCNCC(O)COc4cccc5ccccc45)c4ccccc34)ccc21]
wherein X comprises an anion.
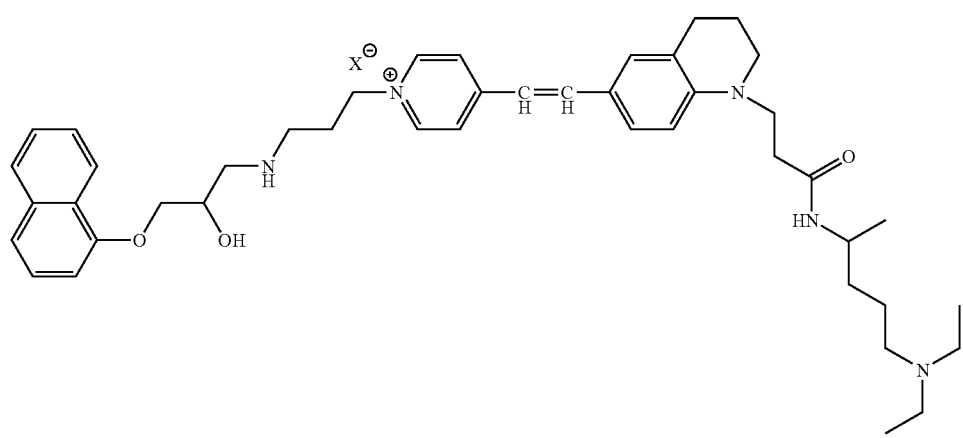 [SMILES: CCN(CC)CCCC(C)NC(=O)CCN1CCCc2cc(C=Cc3cc[n+](CCCNCC(O)COc4cccc5ccccc45)cc3)ccc21]

wherein X comprises an anion.
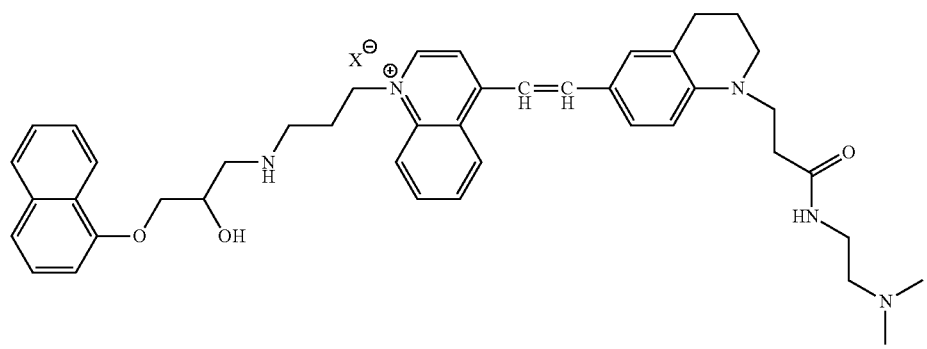
20
wherein X comprises an anion.
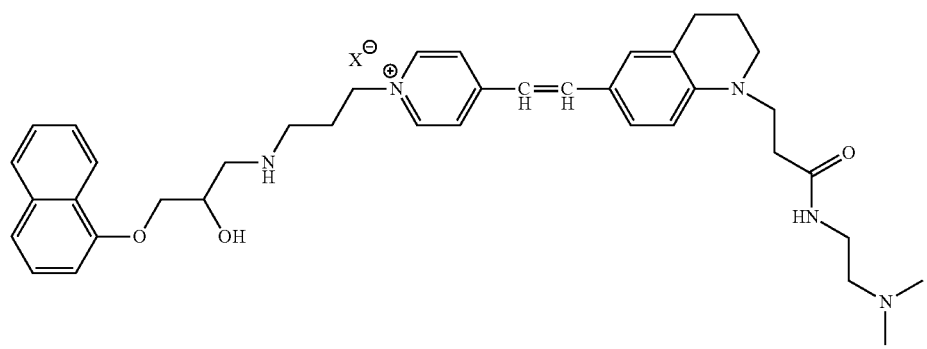
40
wherein X comprises an anion.
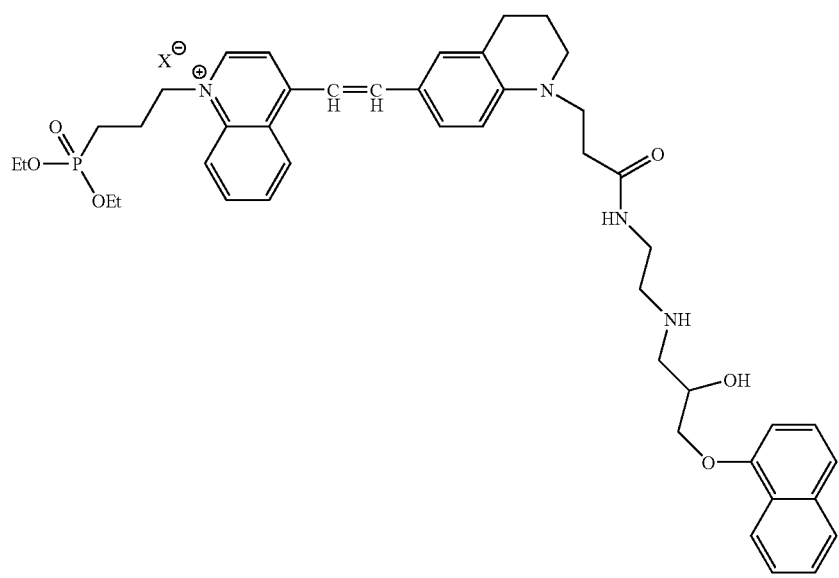 [SMILES: CCOP(=O)(CCC[n+]1ccc(C=Cc2ccc3c(c2)CCCN3CCC(=O)NCCNCC(O)COc2cccc3ccccc23)c2ccccc21)OCC]

wherein X comprises an anion.
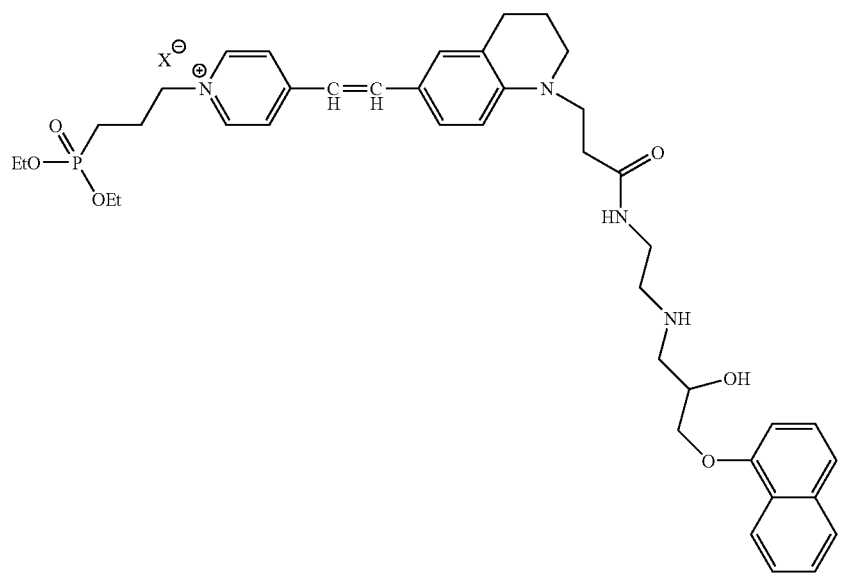 [SMILES: CCOP(=O)(CCC[n+]1ccc(C=Cc2ccc3c(c2)CCCN3CCC(=O)NCCNCC(O)COc2cccc3ccccc23)cc1)OCC]
wherein X comprises an anion.
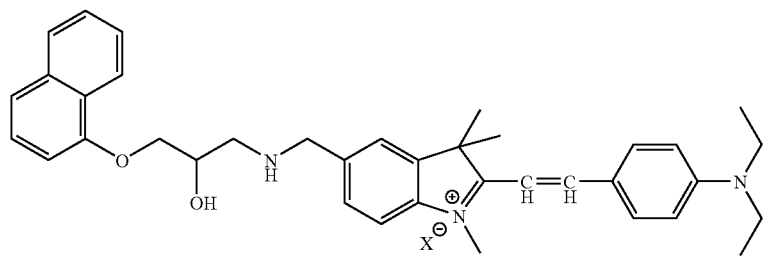 [SMILES: CCN(CC)c1ccc(C=CC2=[N+](C)c3ccc(CNCC(O)COc4cccc5ccccc45)cc3C2(C)C)cc1]
wherein X comprises an anion.
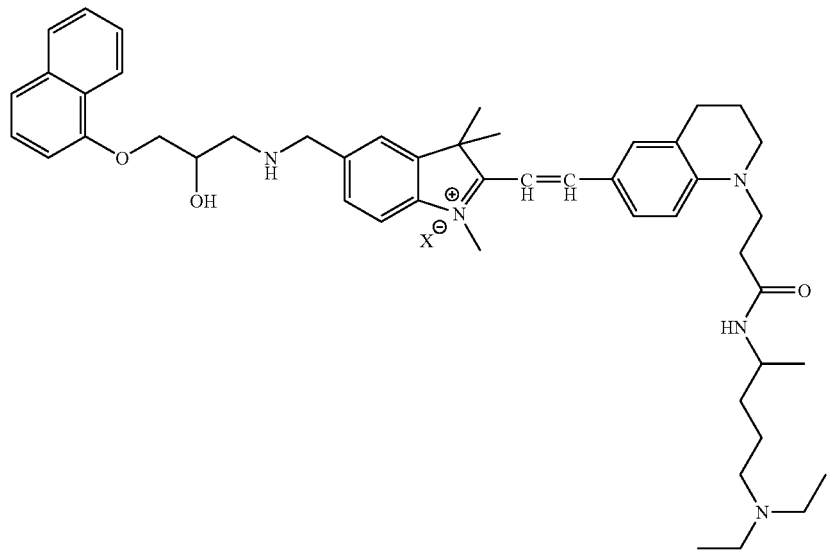 [SMILES: CCN(CC)CCCC(C)NC(=O)CCN1CCCc2cc(C=CC3=[N+](C)c4ccc(CNCC(O)COc5cccc6ccccc56)cc4C3(C)C)ccc21]

wherein X comprises an anion.
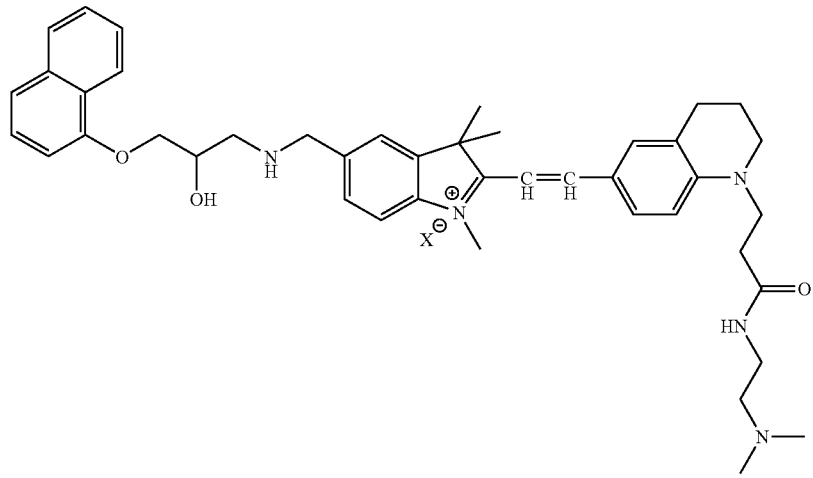 [SMILES: CN(C)CCNC(=O)CCN1CCCc2cc(C=CC3=[N+](C)c4ccc(CNCC(O)COc5cccc6ccccc56)cc4C3(C)C)ccc21]
wherein X comprises an anion.
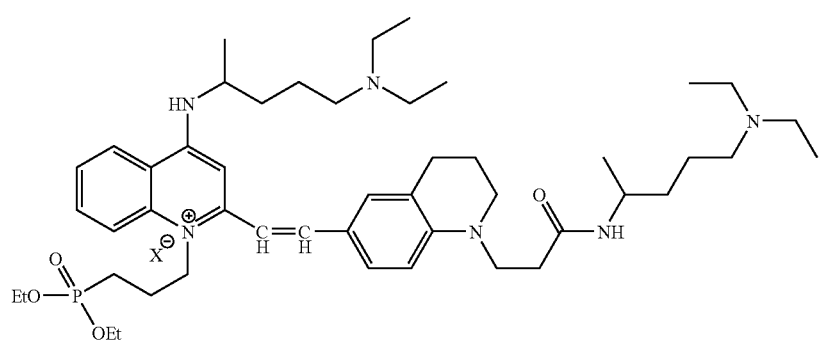 [SMILES: CCOP(=O)(CCC[n+]1c(C=Cc2ccc3c(c2)CCCN3CCC(=O)NC(C)CCCN(CC)CC)cc(NC(C)CCCN(CC)CC)c2ccccc21)OCC]
wherein X comprises an anion.

wherein X comprises an anion.

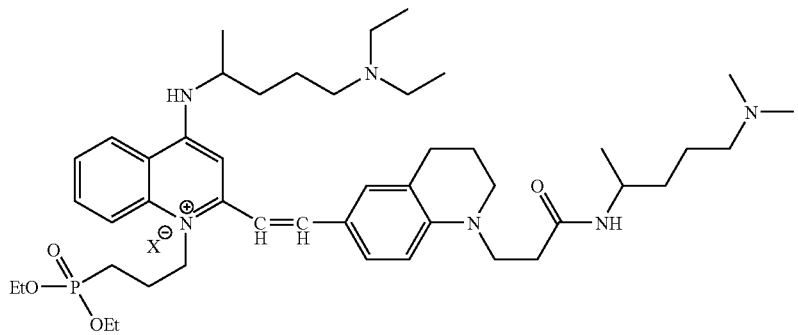 [SMILES: CCOP(=O)(CCC[n+]1c(C=Cc2ccc3c(c2)CCCN3CCC(=O)NC(C)CCCN(C)C)cc(NC(C)CCCN(CC)CC)c2ccccc21)OCC]

wherein X comprises an anion.

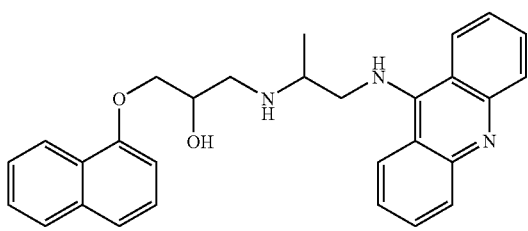

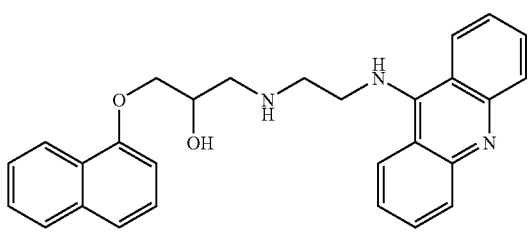

Monitoring Progression of Lysosomal Storage Disease

This invention provides a method of monitoring the progression of a lysosomal storage disease in a subject by comparing vacuole accumulation over a course of $(T_2-T_1)$ time interval(s). Briefly, this method comprises carrying out the steps of: (a) obtaining from the subject at time $T_1$ a first sample containing cells; (b) contacting the first sample with a first cationic amphiphilic tracer compound that localizes to a vacuole in a cell; (c) detecting the first cationic amphiphilic tracer compound, thereby determining the accumulation of vacuoles within the cells of the first sample at time $T_1$; (d) obtaining from the subject at a later time $T_2$ a second sample containing cells; (e) contacting the second sample with a second cationic amphiphilic tracer compound that localizes to a vacuole in a cell; (f) detecting the second cationic amphiphilic tracer compound, thereby determining the accumulation of vacuoles within cells of the second sample at time $T_2$; and (g) comparing the accumulation of vacuoles between the first sample at time $T_1$ and the second sample at time $T_2$, thereby monitoring the progression of lysosome storage disease in the subject.

As described earlier, the lysosomal storage disease sought to be detected can arise from deficiencies of one or more soluble lysosomal proteins residing in the lumen of the lysosome. Alternatively, the lysosomal storage disease can arise from a defect in one or more lysosomal membrane proteins. In other embodiments, the lysosomal storage disease can arise from deficiencies of non-lysosomal proteins residing in a site comprising an endoplasmic reticulum, a Golgi apparatus or an endosomal pathway, as well as combinations of any of the foregoing. In yet other embodiments, the lysosomal storage disease can comprise a mucopolysaccharidoses, a lipidoses or a glycogenosis. Moreover, in carrying out the present detection method, the subject can be one known to have a lysosomal storage disease based upon previous genetic or metabolic testing. The list of lysosomal storage diseases (some 40 in number) are provided above in the definition of lysosomal storage disease and need not be repeated here.

The vacuole in which the cationic amphiphilic tracer compound localizes can comprise a lysosome, a phagophore, an autophagosome or an autophagolysosome, and combinations thereof. The first cationic amphiphilic tracer compound and the second cationic amphiphilic tracer compound can comprise a fluorescent drug that induces phospholipidosis or a fluorescently labeled analog of a drug that induces phospholipidosis. As a further aspect, the first cationic amphiphilic tracer compound and the second cationic amphiphilic tracer compound can comprise a halogenated and fluorescent drug that induces phospholipidosis or a halogenated and fluorescently labeled analog of a drug that induces phospholipidosis. Indeed, the first cationic amphiphilic tracer compound and the second cationic amphiphilic tracer compound can be the same compound, or they can be different compounds.

Among useful cationic amphiphilic tracer compounds for the present invention and method are those comprising nitrobenzoxadiazole (NBD)-spiperone, nitrobenzoxadiazole (NBD)-propranolol, or 9-amino-acridin-propranolol, and combinations of any of the foregoing.

In other embodiments, the cationic amphiphilic tracer compounds have any of the the structures:
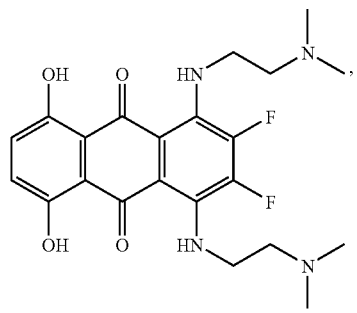 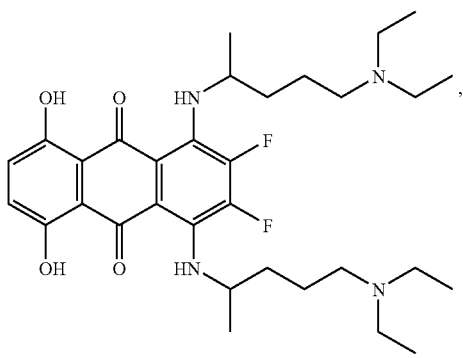
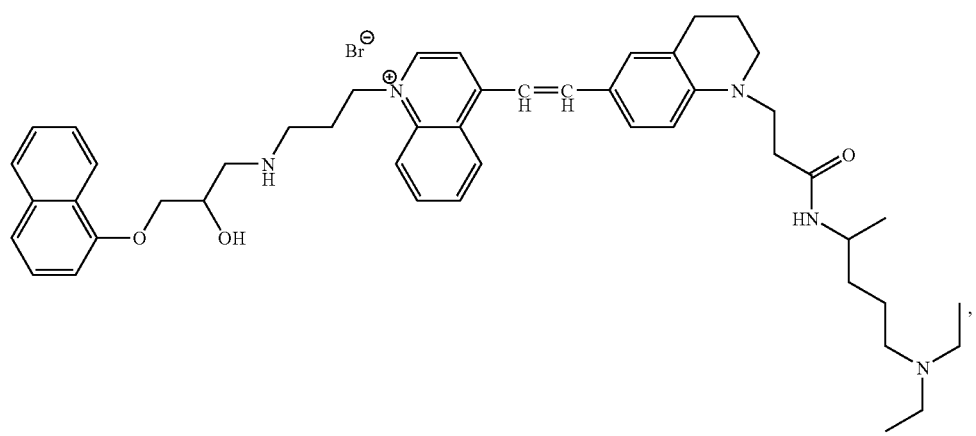
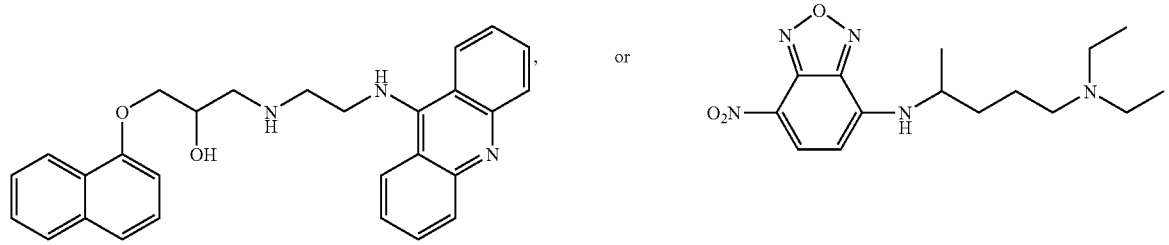
Preferred cationic amphiphilic tracer compounds for carrying out the method for monitoring lysosomal storage disease progression are those having the structures:
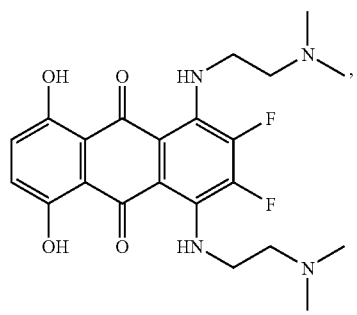

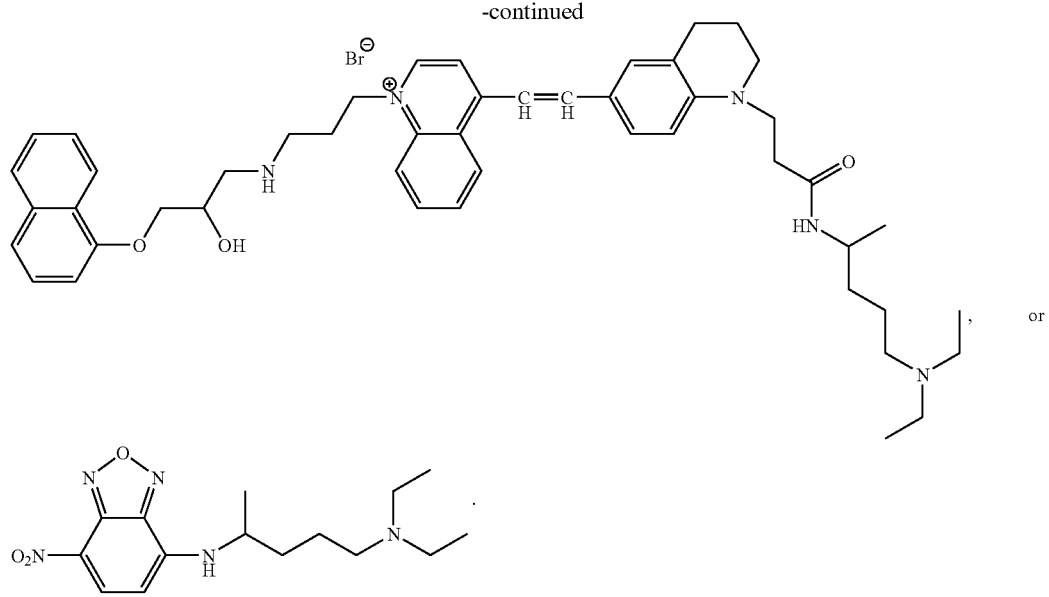

In carrying out this method to monitor the progression of lysosomal storage disease, the difference ($T_2-T_1$) comprises time units can be measured in hours, days, weeks, months or years.

The cells contained in the sample obtained from the subject being monitored can comprise lymphocytes, granulocytes, macrophages or monocytes, and a combination of any of the foregoing. Further, the subject or patient can be a mammal which can be human.

The cations described above serve as counterions for the compounds and dyes of the present invention. Examples of cations that may serve as counterions include but are not limited to hydrogen, sodium, potassium, lithium, calcium, cesium, ammonium, alkyl ammonium, alkoxy ammonium and pyridinium. When a dye comprises a cationic group, an anionic counterion will also be present. Any anion may serve this purpose as long as it doesn't interfere with the use of the dye. Examples of anions that may serve as counterions include but are not limited to halides such as a bromide, chloride, fluoride and iodide. Other examples of anions that can serve as counterions include but are not limited to perchlorate ($ClO_4^-$), sulfate ($SO_4^=$), sulfonate, alkane sulfonate, aryl sulfonate, phosphate, tosylate, mesylate and tetrafluoroborate moieties.

As also described above, in some cases the counterion or counterions are provided by the dye being presented as a salt where it exists as separate ionic species. In other cases, the counterion or counterions may be present as part of the compound (sometimes called inner salts). It is understood that a combination of ions may be provided by the compound and salts. With regard to acid moieties that are shown in forms such as COOH, it should be understood and appreciated that these compounds may be found in ionized forms such as COO$^-$. It should also be appreciated by those skilled in the art that the stoichiometric number of counterion or counterions which balance the charge or charges on the compounds of the present invention can be the same or they can be different, provided that the counterions balance the charge(s) on the compound. The combination of counterions can be selected from any of the anions described above. Similarly, the combination of counterions can also be selected from any of the cations described above.

Monitoring Drug/Remedy Effectiveness for Lysosomal Storage Disease

The present invention further provides a method of monitoring the effectiveness of a drug or remedy used to manage, treat or cure a lysosomal storage disease in a subject, comprising the steps of: (a) obtaining from the subject at time $T_1$ a first sample containing cells; (b) contacting the first sample with a first cationic amphiphilic tracer compound that localizes to a vacuole in a cell; (c) detecting the first cationic amphiphilic tracer compound, thereby determining the accumulation of vacuoles within the cells of the first sample at time $T_1$; (d) obtaining from the subject at a later time $T_2$ a second sample containing cells; (e) contacting the second sample with a second cationic amphiphilic tracer compound that localizes to a vacuole in a cell; (f) detecting the second cationic amphiphilic tracer compound, thereby determining the accumulation of vacuoles within cells of the second sample at time $T_2$; and (g) comparing the accumulation of vacuoles between the first sample at time $T_1$ and the second sample at time $T_2$, thereby monitoring the effectiveness of the drug used to manage, treat or cure lysosome storage.

As explained above, lysosomal storage disease can arise from deficiencies of one or more soluble lysosomal proteins residing in the lumen of the lysosome. Alternatively, the lysosomal storage disease can arise from a defect in one or more lysosomal membrane proteins. In other aspects, the lysosomal storage disease can arise from deficiencies of non-lysosomal proteins residing in a site comprising an endoplasmic reticulum, a Golgi apparatus or an endosomal pathway, and combinations of any of the foregoing. In further aspects, the lysosomal storage disease comprises a: mucopolysaccharidoses, a lipidoses or a glycogenosis. Moreover, the method can be usefully carried out in a subject is known to have a lysosomal storage disease based upon previous genetic or metabolic testing. As explained above, a list of lysosomal storage diseases has been provided in the above definition of lysosomal storage disease, and will not be repeated.

The first and second cationic amphiphilic tracer compounds can localize in vacuoles, the latter comprising lysosomes, phagophores, aautophagosomes or an autophagolysosomes, and combination of the foregoing. Useful in the present invention are first cationic amphiphilic tracer compounds and the second cationic amphiphilic tracer compounds comprising fluorescent drugs that induces phospholipidosis or a fluorescently labeled analogs of a drug that induces phospholipidosis. In other aspects, the first cationic amphiphilic tracer compounds and the second cationic amphiphilic tracer compound comprise halogenated and fluorescent drugs that induce phospholipidosis or a halogenated and fluorescently labeled analog of a drug that induces phospholipidosis.

It should be appreciated by those skilled in the art that the first cationic amphiphilic tracer compound and the second cationic amphiphilic tracer compound can be the same compounds, or they can be different compounds.

Among useful cationic amphiphilic tracer compounds in the present invention and method are those comprising nitrobenzoxadiazole (NBD)-spiperone, nitrobenzoxadiazole (NBD)-propranolol, or 9-amino-acridin-propanolol, and combinations of any of the foregoing.

In other embodiments, the cationic amphiphilic tracer compounds have any of the following the structures:

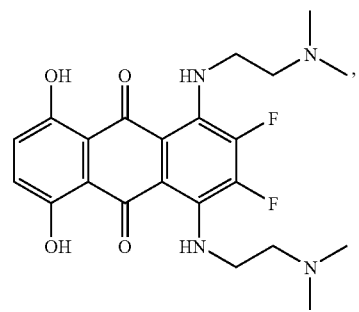

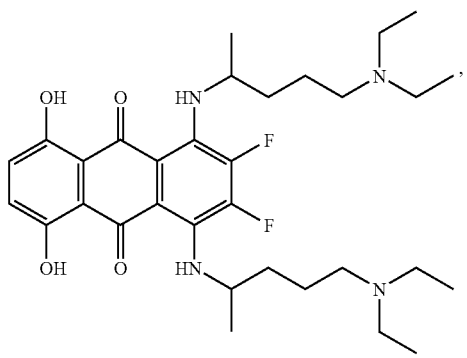

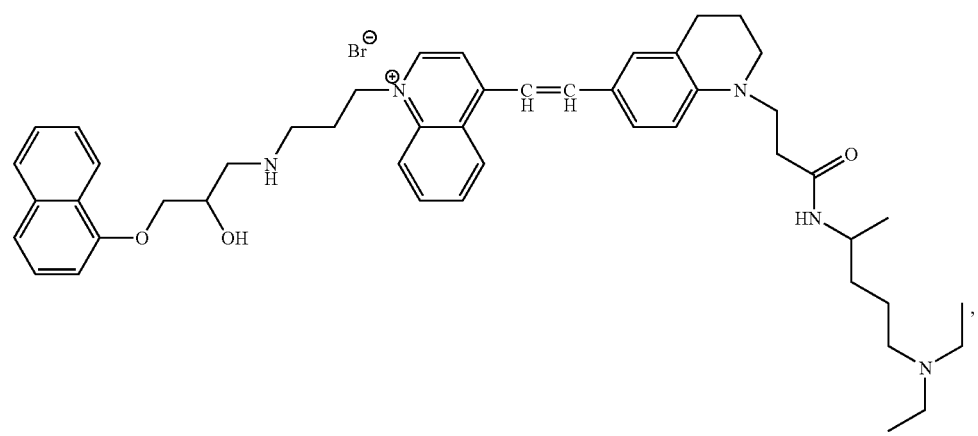

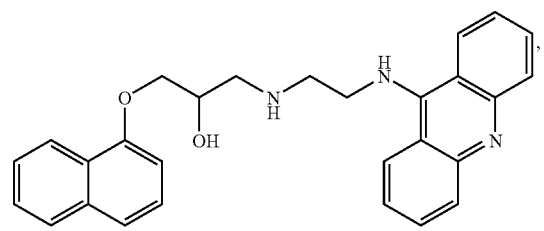 or 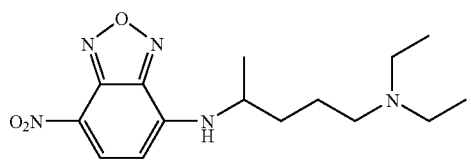

Particularly preferred in carrying out the present invention and method of monitoring the effectiveness of a drug or remedy used to manage, treat or cure a lysosomal storage disease in a subject are those cationic amphiphilic tracer compounds having the structures:

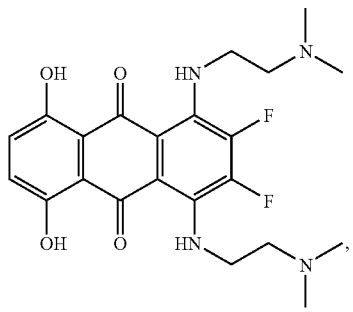

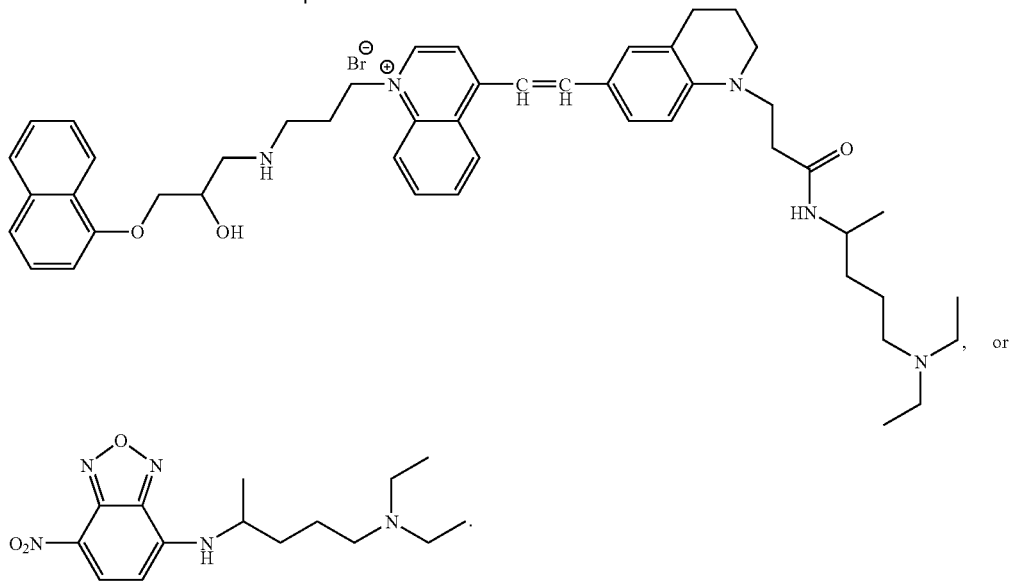

In monitoring the effectiveness of any drug or remedy used to manage, treat or cure lysosomal storage disease, the difference $(T_1-T_2)$ can comprise time units measured in various units, such as hours, days, weeks, months or years.

The cells which are contained in the samples obtained from the subject or patient can comprise lymphocytes, granulocytes, macrophages or monocytes, and a combination of any of the foregoing. The subject can be a mammal which can be human.

Screening Drug Candidates for Toxicity

This invention also provides for screening drug candidates to determine their toxicity to cells, tissues or organs. This method comprises the steps of: (a) providing: (i) at least one first sample and one second sample of mammalian cells; (ii) a drug candidate for screening; (iii) a drug diluting vehicle or carrier; and (iv) a cationic amphiphilic tracer compound that localizes to a vacuole in a cell; (b) administering: (i) the drug candidate (ii) to the first sample for a time sufficient to allow the drug candidate to partition into subcellular compartments within the cells to form treated cells; and (ii) the vehicle or carrier (iii) to the second sample to form untreated reference cells; (c) contacting the treated cells and the untreated reference cells with the cationic amphiphilic tracer (iv) for a period of time sufficient to accumulate in vacuoles in the cells, and (d) detecting any increase in vacuole accumulation of the cationic amphiphilic tracer compound in the treated cells relative to the untreated reference cells, thereby determining whether the drug candidate has accumulated in the vacuoles and is toxic to cells, tissues or organs.

In other aspects of this method, the vehicle or carrier comprises cell culture medium, buffer, organic solvent or water, and combinations of the foregoing. The organic solvent can comprise dimethylsulfoxide (DMSO).

The vacuoles in the mammalian cells can comprise lysosomes, phagophores, autophagosomes or autophagolysosomes, and combinations of the foregoing.

In other embodiments, the first cationic amphiphilic tracer compound and the second cationic amphiphilic tracer compound can comprise fluorescent drugs that induce phospholipidosis or fluorescently labeled analogs of a drug that induce phospholipidosis. In yet further embodiments, the first cationic amphiphilic tracer compounds and the second cationic amphiphilic tracer compounds can comprise halogenated and fluorescent drugs that induce phospholipidosis or halogenated and fluorescently labeled analogs of a drug that induce phospholipidosis.

In certain aspects of this invention and method, the cationic amphiphilic tracer compounds comprise nitrobenzoxadiazole (NBD)-spiperone, nitrobenzoxadiazole (NBD)-propranolol, or 9-amino-acridin-propanolol and combinations of any of the foregoing. In other aspects, the cationic amphiphilic tracer compounds have any of the following structures:

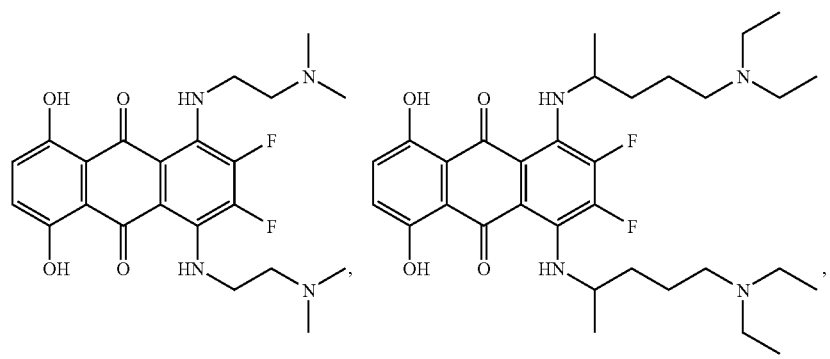
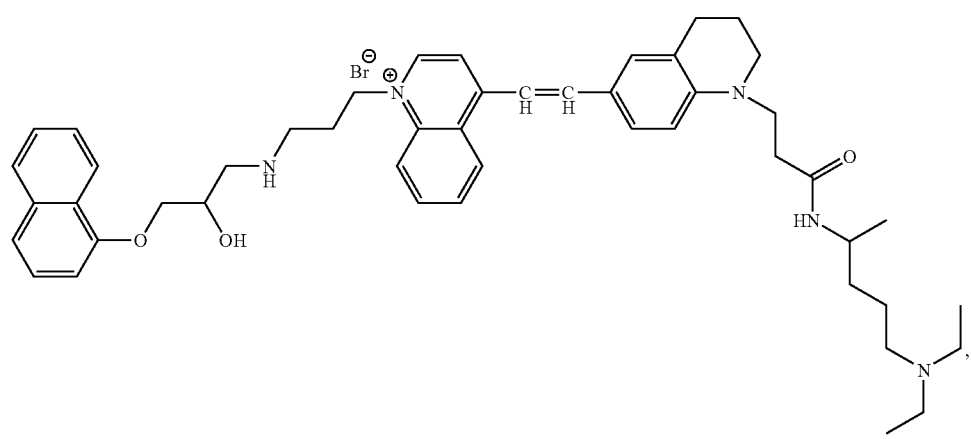
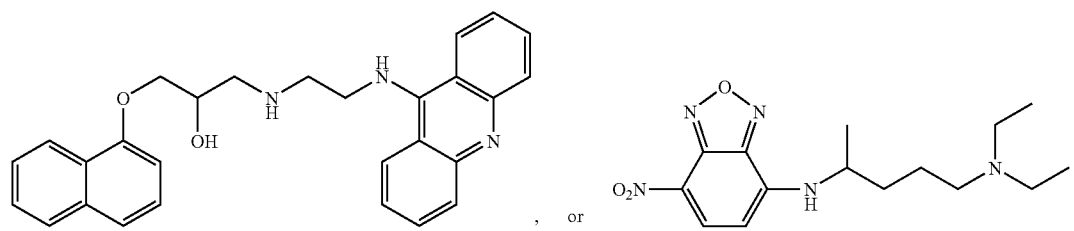
Preferred in the methods of the present invention for screening drug candidates to determine their toxicity to cells, tissues or organs are the cationic amphiphilic tracer compounds having the structures:
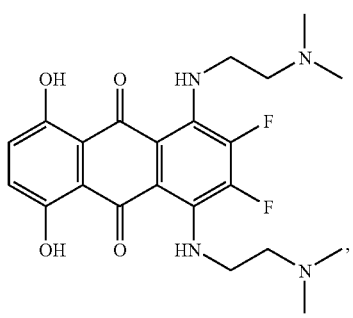

-continued

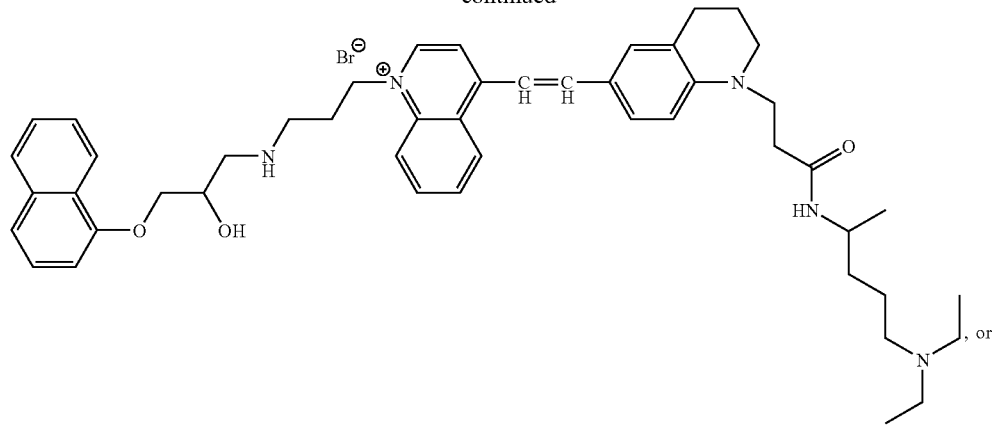

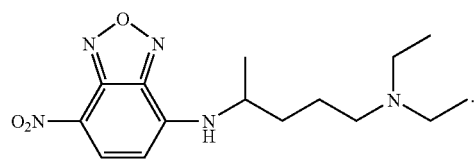

The mammalian cells used in the method of the present invention can be from a cell line which can be a human cell line. Furthermore, the mammalian cells can be from a subject who can be a human. The cells used in this method can comprise lymphocytes, granulocytes, macrophages or monocytes, and a combination of any of the foregoing.

Screening Suspected Toxic Agents for Toxicity

This invention also provides a method of screening suspected toxic agents to determine their toxicity to cells, tissues or organs. In carrying this method, the following steps are carried out: (a) providing: (i) at least one first sample and one second sample of mammalian cells; (ii) a suspected toxic agent for screening; (iii) a diluting vehicle or carrier; and (iv) a cationic amphiphilic tracer compound that localizes to a vacuole in a cell; (b) administering: (i) the suspected toxic agent (ii) to the first sample for a time sufficient to allow the suspected toxic agent to partition into subcellular compartments within the cells to form treated cells; and (ii) the diluting vehicle or carrier (iii) to the second sample to form untreated reference cells; (c) contacting the treated cells and the untreated reference cells with the cationic amphiphilic tracer (iv) for a period of time sufficient to accumulate in vacuoles in the cells, and (d) detecting any increase in vacuole accumulation of the cationic amphiphilic tracer compound in the treated cells relative to the untreated reference cells, thereby determining whether the suspected toxic agent has accumulated in the vacuoles and is toxic to cells, tissues or organs.

In other embodiments of this invention, the vehicle or carrier comprises cell culture medium, buffer, organic solvent or water, and combinations of the foregoing. In one embodiment, the organic solvent can comprises dimethylsulfoxide (DMSO).

The vacuoles contained in the mammalian cells can comprise lysosomes, phagophores, autophagosomes or autophagolysosomes, and a combination of the foregoing.

In certain aspect of this invention and method, the first cationic amphiphilic tracer compounds and the second cationic amphiphilic tracer compounds can comprise fluorescent drugs that induce phospholipidosis or fluorescently labeled analogs of a drug that induce phospholipidosis. In other aspects of this invention, the first cationic amphiphilic tracer compounds and the second cationic amphiphilic tracer compounds comprise halogenated and fluorescent drugs that induce phospholipidosis or halogenated and fluorescently labeled analogs of drug that induce phospholipidosis.

Among the preferred cationic amphiphilic tracer compounds are those comprising nitrobenzoxadiazole (NBD)-spiperone, nitrobenzoxadiazole (NBD)-propranolol, or 9-amino-acridin-propanolol and combinations of any of the foregoing.

Also useful in the present method are cationic amphiphilic tracer compounds having any of the following structures:

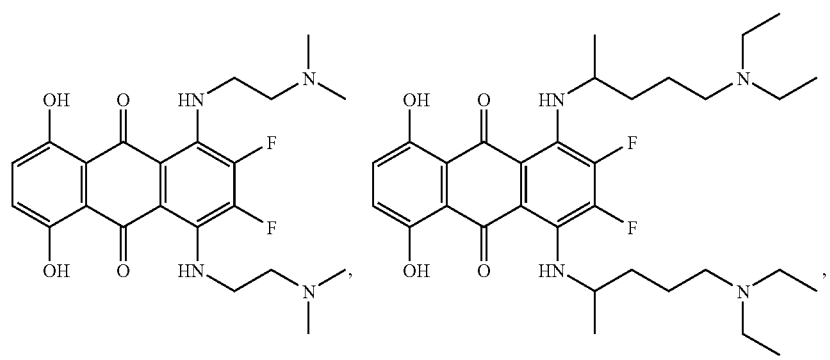
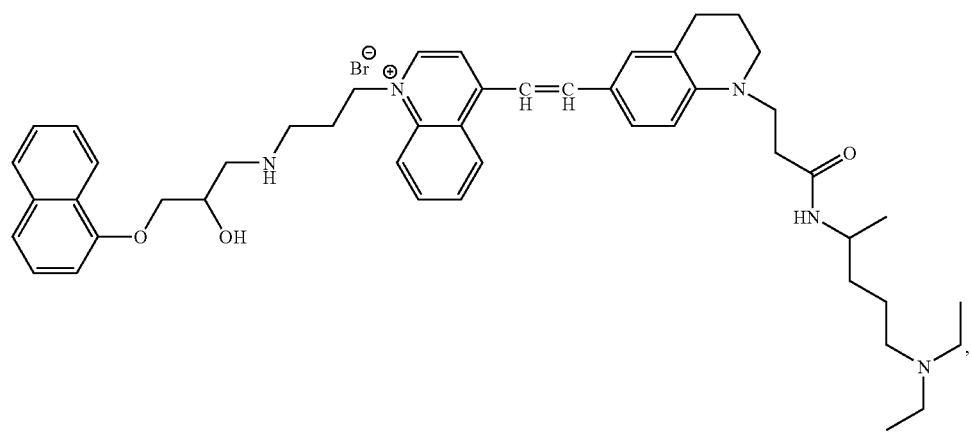
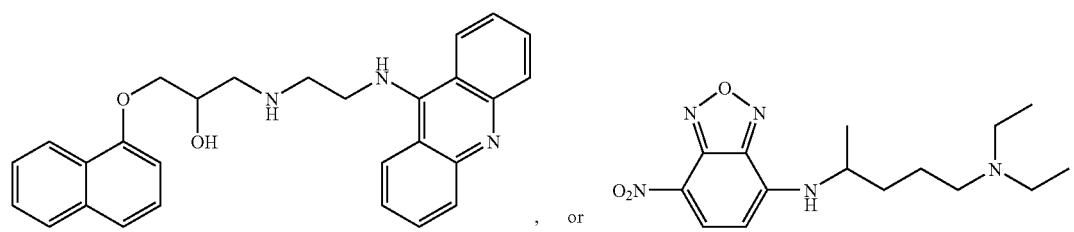
Preferred for carrying out the method of screening suspected toxic agents to determine their toxicity to cells, tissues or organs are the cationic amphiphilic tracer dye compounds having the structures:
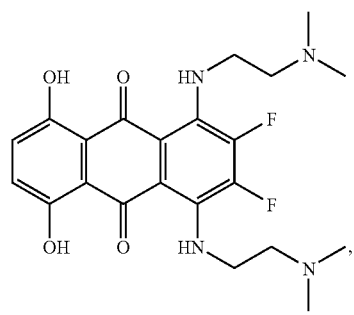

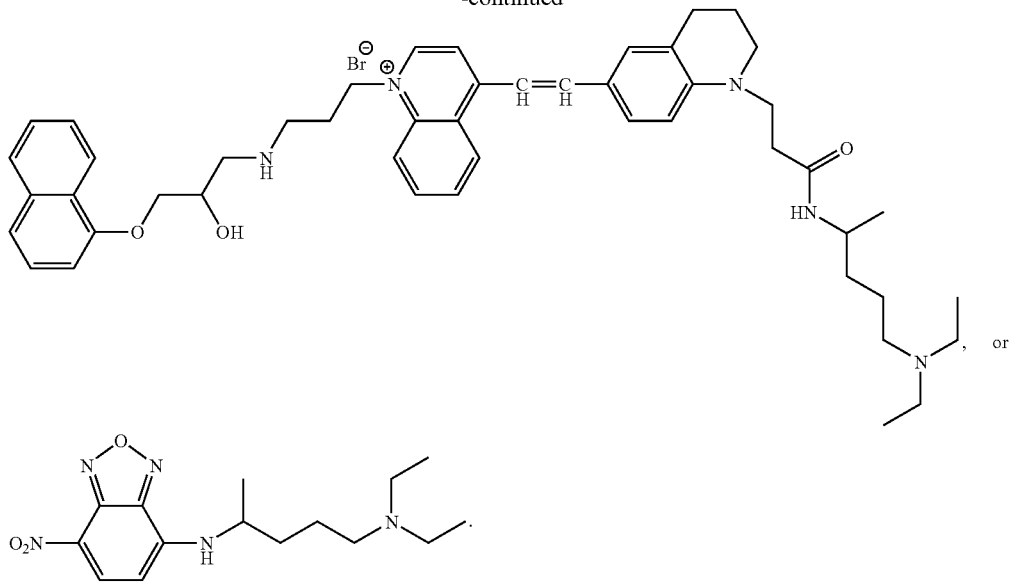

In carrying out the present method, the mammalian cells can be from a cell line which can be a human cell line. Further, the mammalian cells can be from a subject who can be human.

In another embodiment, the mammalian cells can comprise lymphocytes, granulocytes, macrophages or monocytes, and a combination of any of the foregoing.

Distinguishing Phospholipidosis Activators from Autophagy Pathway Perturbation Agents This invention additionally provides a method of distinguishing between phospholipidosis activators and autophagy pathway perturbation agents. To distinguish these activators from such agents, the following steps are carried out: (a) providing: (i) a fluorescent phospholipid analog compound that forms multilamellar vesicles; (ii) a cationic amphiphilic fluorophore tracer compound that localizes in a vacuole in a cell; (iii) a test agent; and (iv) a sample of mammalian cells; (b) administering to the cells in the sample (iv) the fluorescent phospholipid analog compound (i) and the test agent (iii) to form a testing mixture; (c) contacting the testing mixture with the cationic amphiphilic fluorophore tracer (ii); and (d) detecting any signals generated from the fluorescent phospholipid analog compound (i) and the cationic amphiphilic fluorophore tracer compound (ii), thereby differentiating between phospholipidosis activators and autophagy pathway perturbation agents based upon differential accumulation patterns of the fluorescent phospholipid analog and the cationic amphiphilic fluorophore tracer.

In certain aspects of this invention and method, the fluorescent phospholipid analog compound comprises NBD-PE (N-(-7-nitrobenz-2-oxa-1,3-diazol-4-yl)-1,2-dihexadecanoyl-sn-glycero-3-phosphoethanolamine), NBD-PC (1-acyl-2-(12[(7-nitro-2-1-3-benzoxadiazol-4yl)amino] dodecanoyl)phosphatidylcholine), CF-PE (1,2-dioleoyl-sn-glycero-3-phosphoethanolamine-N-(carboxyfluorescein)) or Lipid-Tox reagent, and a combination of any of the foregoing.

The vacuoles can comprise lysosomes, phagophores, autophagosomes or autophagolysosomes, and a combination of the foregoing.

The cationic amphiphilic tracer compounds can comprise fluorescent drugs that that induce phospholipidosis or fluorescently labeled analogs of drugs that induce phospholipidosis. In some aspects, the cationic amphiphilic tracer compound can comprise halogenated and fluorescent drugs that induce phospholipidosis or halogenated and fluorescently labeled analogs of drugs that induce phospholipidosis.

In certain other aspects, the cationic amphiphilic tracer compounds have any of the following structures:

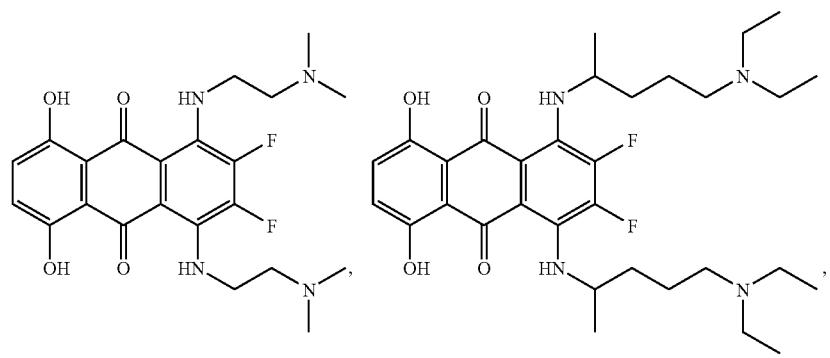

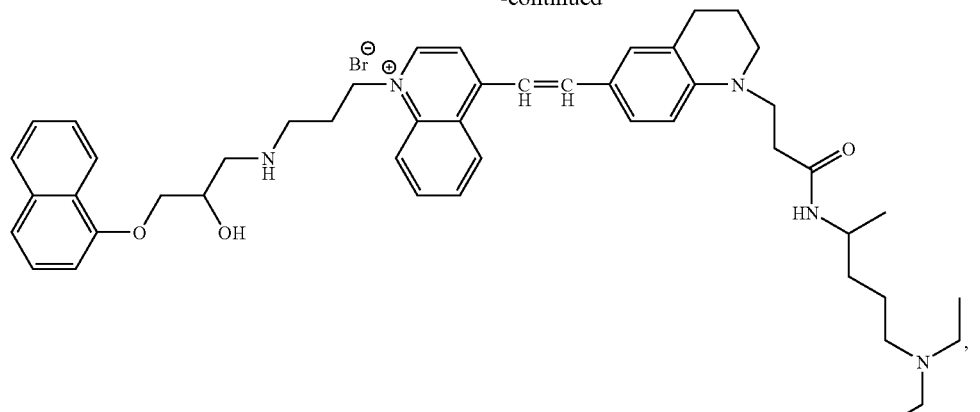
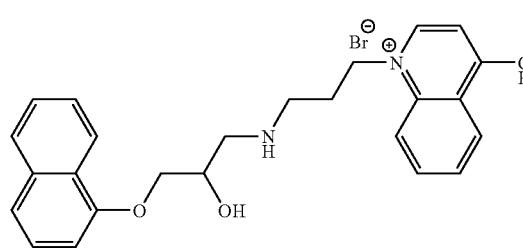
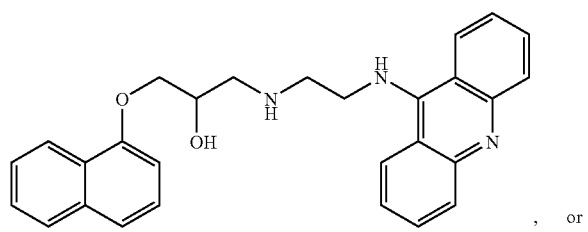
Preferred in the present invention and method for distinguishing phospholipidosis activators from autophagy pathway perturbation agents are the cationic amphiphilic tracer dye compounds having the structures:
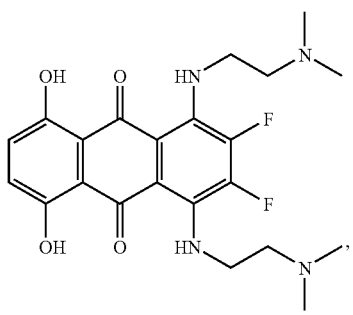
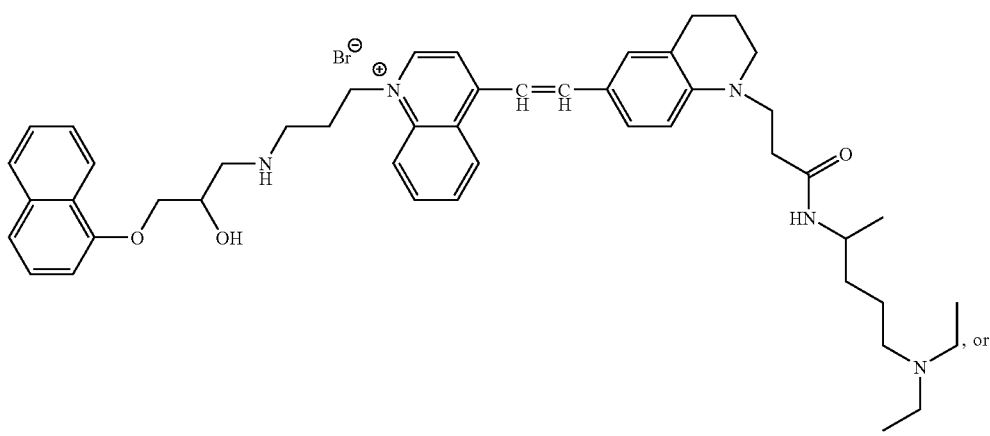

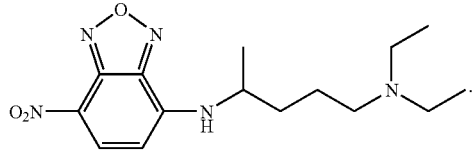

In carrying out this method, the test agent can a drug candidate or an environmental contaminant. The mammalian cells contained in the sample can comprise lymphocytes, granulocytes, macrophages or monocytes, and a combination of any of the foregoing. The mammalian cells can be from a cell line, including a human cell line. The mammalian cells can be from a subject who can be a human.

In distinguishing between activators and agents using the method of the present invention, phospholipidosis is identified as increased accumulation of both the fluorescent phospholipid analog compound and the cationic amphiphilic fluorophore tracer compound. Additionally, the autophagy pathway perturbation agent is identified by no increased accumulation of the fluorescent phospholipid analog compound, but increased accumulation of the cationic amphiphilic fluorophore tracer compound.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Synthesis of 1,4-bis(2-(dimethylamino)ethylamino)-2,3-difluoro-5,8-dihydroxyanthracene-9,10-dione (Dye 1)

A mixture of 1,2,3,4-tetrafluoro-5,8-dihydroxyanthraquinone (1.0 g, 3.2 mmol) and N,N-dimethylethylenediamine (3 mL) in $CH_2Cl_2$ (30 mL) was stirred at room temperature for 12 hours. After evaporation of the solvents, the residue was purified by silica gel chromatography using isocratic solvent system of $EtOAc/MeOH/Et_3N$ (10:10:1) yielding 830 mgs of Dye 1 as dark blue product. Abs (max, PBS pH 7.4)=568 nm; Em=675 nm. The structure of Dye 1 is given below:

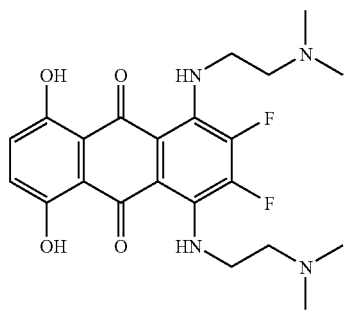

Dye 1

Example 2

Synthesis of 1,4-bis(5-(diethylamino)pentan-2-ylamino)-2,3-difluoro-5,8-dihydroxyanthracene-9,10-dione (Dye 2)

A mixture of 1,2,3,4-tetrafluoro-5,8-dihydroxyanthraquinone (0.47 g, 1.5 mmol) and 2-Amino-5-diethylaminopentane (2.3 mL) in $CH_2Cl_2$ (20 mL) was stirred at room temperature for 12 hours. After evaporation of the solvents, the residue was purified by silica gel chromatography using isocratic solvent system of $CH_2Cl_2/MeOH/Et_3N$ (100:10:1) yielding 364 mgs of Dye 2 as dark blue product. Abs (max, PBS pH 7.4)=667 nm; Em=700 nm. The structure of Dye 2 is given below:

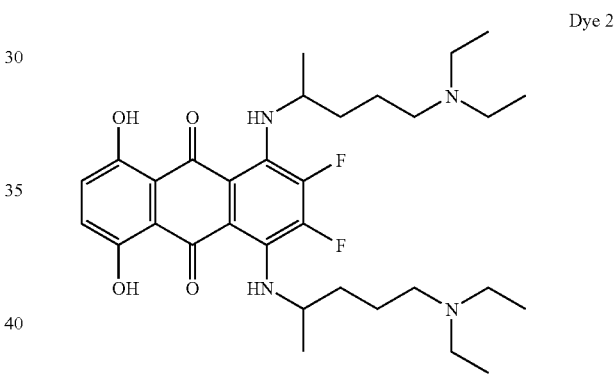

Dye 2

Example 3

Synthesis of Dye 3

(a) Preparation of 2-((naphthalene-1-yloxy)methyl)oxirane (Compound 1)

To a solution of 1-naphthol (3.0 g, 0.02 mol) in DMSO (10 mL), potassium hydroxy (flakes, 2.0 g, 0.06 mol) was added. The combined mixture was stirred at room temperature for 30 min and then epichlorohydrin (5.6 g, 4.7 mL, 0.06 mol) was added slowly over a period of 45 min and stirring was continued for 16 hours. The reaction was quenched with water (30 mL) and extracted with chloroform (2×50 mL). The combined organic layers were washed with 1N aqueous NaOH (2×50 mL), water (2×100 mL) and brine (2×100 mL) and dried over $MgSO_4$. The solvent was removed under reduced pressure to provide Compound 1 as a yellow liquid (3.26 g, 78%). This product was used without further purification. The structure of Compound 1 is given below:

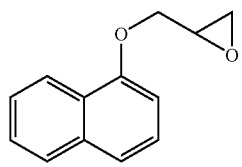

Compound 1

(b) Preparation of 1-(3-ammoniopropyl)-4-methylquinolinium bromide (Compound 2)

A mixture of lepidine (3.0 g, 21 mmol) and 3-bromopropylamine hydrobromide (4.6 g, 21 mmol) in 1,2-dichlorobenzene (50 mL) was heated at 135° C. for 16 hours. The mixture was cooled and 1,2-dichlorobenzene was decanted. The residue thus obtained was suspended in methanol (25 mL) and refluxed for 10 min. It was cooled and separated solid was collected by centrifugation, washed with methanol (2×30 mL) and dried under high vacuum to yield Compound 2 as an light gray solid (1.4 g, 19%). This product was used without further purification. The structure of Compound 1 is given below:

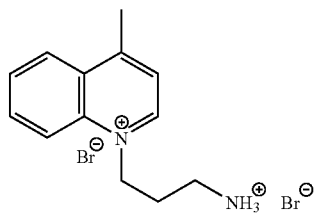

Compound 2

(c) Preparation of 1-(3-(2-hydroxy-3-(naphthalen-1-yloxy)propylamino)propyl)-4-methylquinolinium bromide (Compound 3)

To a suspension of Compound 1 (0.17 g, 0.83 mmol) and Compound 2 (0.30 g, 0.83 mmol) in water (1 mL), triethylamine (0.10 g, 0.99 mmol) was added. The combined mixture was stirred at room temperature for 24 hours and then evaporated in the rotary evaporator to provide Compound 3 as a solid. This product was used without any workup and further purification. The structure of Compound 3 is given below:

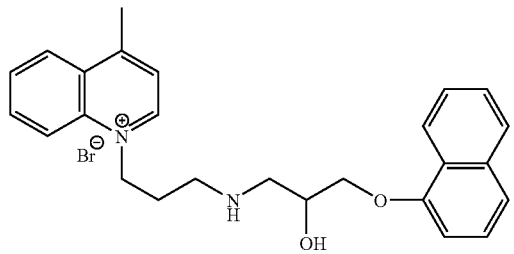

Compound 3

(d) Preparation of Dye 3

To a mixture of Compound 3 (0.20 g, 0.5 mmol) and 4-dimethylamino benzaldehyde (0.09 g, 0.5 mmol) in glacial acetic acid (5 mL), piperidine (0.043 g, 0.5 mmol) was added. The combined mixture was heated in an oil bath at 110° C. for 5 hours. Upon cooling the reaction mixture was added to 40% aqueous sodium iodide solution (15 mL) and kept at room temperature for 18 hours. Precipitated dye was collected by centrifugation, washed with water, dried under vacuum and purified by Biotage (SNAP 25 g column) using a gradient of methanol in methylene chloride (1% to 10% over 10 column volume). Appropriate fractions pooled together and dried in a rotary evaporator to provide Dye 3 as a purple solid (128 mg). Abs (max, methanol)=565 and 295 nm. The structure of Dye 3 is given below:

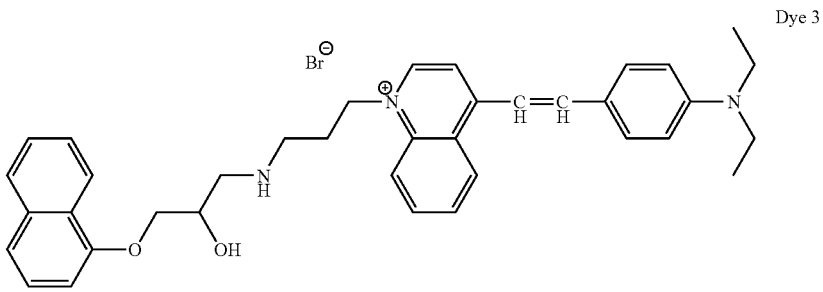 [SMILES: CCN(CC)c1ccc(C=Cc2cc[n+](CCCNCC(O)COc3cccc4ccccc34)c3ccccc23)cc1 ; [Br-]]

Dye 3

Example 4

Synthesis of Dye 4

(a) Preparation of 3-(3,4-dihydroquinolin-1(2H)-yl) propanoic acid (Compound 4)

A mixture of 1,2,3,4-tetrahydroquinoline (3.0 g, 22.5 mmol) and methylacrylate (3.88 g, 45.1 mmol) in glacial acetic acid (15 mL) was refluxed for 16 hours. Volatiles were then removed in the rotary evaporator and the residue thus obtained was co-evaporated with methanol (3×20 mL) and then dissolved in 15 mL methanol. To this mixture, an aqueous solution of LiOH (1.9 g, 45 mmol, 15 mL) was added and combined mixture was stirred at room temperature for 2 hours. Reaction mixture was made acidic with conc. HCl (pH~2) and extracted with ethyl acetate (2×50 mL). The combined organic layers were washed with water (2×100 mL) and brine (2×100 mL) and dried over MgSO$_4$. The solvent was removed under reduced pressure to provide Compound 4 as a dark brown viscous liquid (2.91 g). This product was used without further purification. The structure of Compound 4 is given below:

Compound 4

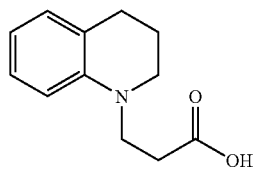

(b) Preparation of N-(5-(diethylamino)pentan-2-yl)-3-(3,4-dihydroquinolin-1(2H)-yl)propanamide (Compound 5)

To a solution of Compound 4 (1.9 g, 9.3 mmol) in DMF (35 mL), 2-succinimido-1,1,3,3-tetramethyluronium tetrafluoroborate (3.4 g, 11.2 mmol) and N,N-diisopropyl ethylamine (3.4 mL, 19.5 mmol) were added. Combined mixture was stirred at room temperature for 30 mins and then a solution of 2-amino-5-diethylaminopentane (2.2 g, 13.9 mmol) in DMF (5 mL) was added. After stirring the mixture for additional 1 hour, it was poured in brine (100 mL) and extracted with ethyl acetate (2×75 mL). The combined organic layers were washed with brine (3×100 mL) and dried over MgSO$_4$. The solvent was removed under reduced pressure to provide Compound 5 as a dark yellow viscous liquid (2.64 g, 82.5%). This product was used without further purification. The structure of Compound 5 is given below:

Compound 5

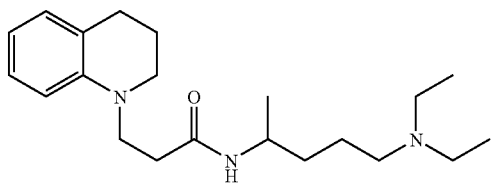

(c) Preparation of N-(5-(diethylamino)pentan-2-yl)-3-(6-formyl-3,4-dihydroquinolin-1(2H)-yl)propanamide (Compound 6)

POCl$_3$ (2.37 g, 15.3 mmol) was added dropwise to DMF (1.8 mL) which was cooled in an ice bath. The combined mixture was stirred for 30 minutes and to this a solution of Compound 5 (2.64 g, 7.6 mmol) in DMF (25 mL) was added dropwise over a period of 20 min. After the addition was complete, the ice bath was removed and the reaction mixture was stirred at room temperature for 17 hour. An aqueous solution of sodium acetate (25% w/w, 25 mL) was then added to the reaction mixture and it was heated in an oil bath (T=110° C.) for 15 min. The reaction mixture was cooled and pH was adjusted with 10 N NaOH to ~11. It was diluted with water (100 mL) and extracted with ethyl acetate. The organic layer was washed twice with water (75 mL) followed by brine (3×50 mL), dried over magnesium sulfate and then evaporated to dryness to yield 1.44 g of an orange viscous liquid which was used without any further purification. The structure of Compound 6 is given below:

Compound 6

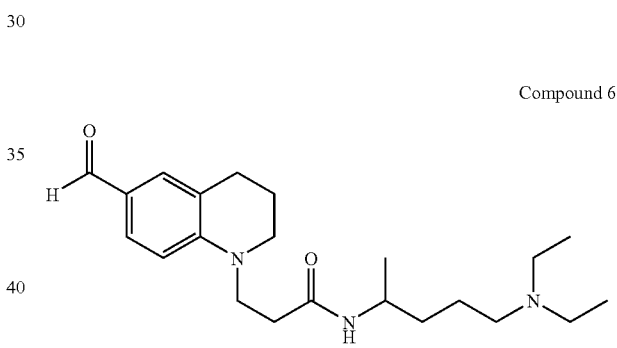

(d) Preparation of Dye 4

To a mixture of Compound 3 (0.15 g, 0.3 mmol) and Compound 6 (0.13 g, 0.34 mmol) in glacial acetic acid (4 mL), piperidine (0.029 g, 0.34 mmol) was added. The combined mixture was heated in an oil bath at 110° C. for 5 hours. Upon cooling the reaction mixture was added to 40% aqueous sodium iodide solution (12 mL) and kept at room temperature for 18 hours. Precipitated dye was collected by centrifugation, washed with water, dried under vacuum and purified by Biotage (SNAP 25 g column) using a gradient of methanol in methylene chloride (1% to 10% over 10 column volume). Appropriate fractions pooled together and dried in a rotary evaporator to provide Dye 4 as a purple solid (75 mg). Abs (max, methanol)=577 and 297 nm. The structure of Dye 4 is given below:

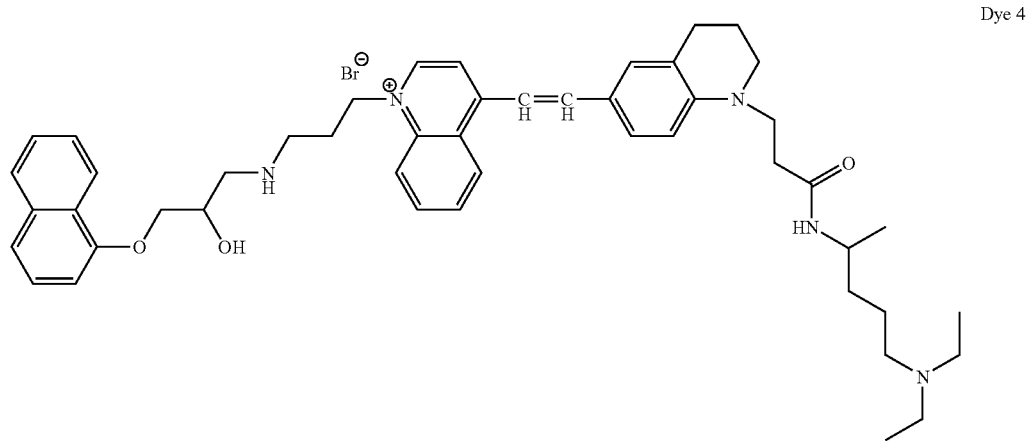 [SMILES: CCN(CC)CCCC(C)NC(=O)CCN1CCCc2cc(C=Cc3cc[n+](CCCNCC(O)COc4cccc5ccccc45)c4ccccc34)ccc21 ; [Br-]]

Dye 4

Example 5

Synthesis of Dye 5

(a) Preparation of $N^1$-(acridin-9-yl)ethane-1,2-diamine hydrochloride (Compound 7)

A mixture of 9-chloroacridine (1.21 g, 5.7 mmol) and phenol (10.8 g, 57 mmol) was mixed and heated at 110° C. for 45 min under argon. Distilled ethylene diamine (3.4 g, 57 mmol) was added via syringe. After the reaction mixture was heated at 110° C. for additional 2 hrs, it was poured into 2N NaOH solution (60 mL). The product was extracted with ethyl ether (3×100 mL). The combined organic layer was washed with 2N NaOH solution (40 mL) and water (2×100 mL) and dried with anhydrous potassium carbonate. The solution was concentrated to 15 mL. Ethanol (15 mL) was added, followed by the addition of concentrated hydrochloric acid (10 mL). The mixture was cooled in freezer (−20° C.) for 4 hrs. The yellow solid formed was collected by centrifugation, washed with ethyl ether (10 mL) and dried under vacuum to provide Compound 7 as yellow powder 0.82 g (53%) which was used without any further purification. The structure of Compound 7 is given below:

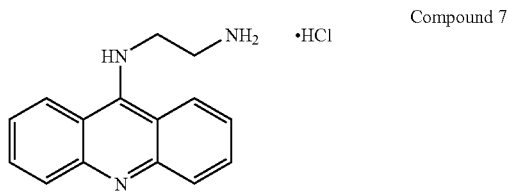 [SMILES: NCCNc1c2ccccc2nc2ccccc12 ; Cl]

Compound 7

(b) Preparation of Dye 5

To a solution of Compound 1 (200 mg, 1 mmol) in diisopropylethylamine (0.6 mL) and dioxane (4 mL), was added Compound 7 (274 mg, 1 mmol). The reaction mixture was heated at 50° C. for 20 hrs. The yellow precipitate was collected by centrifugation and then further purified by flash chromatography (gradient of mobile phase: dichloromethane/methanol=50/1 to 5/1). The solvent was removed under vacuum to provide Dye 5 as a yellow solid (34.5 mg, 8%). Abs (max, methanol)=412 and 440 nm; Em (max, methanol)=426, 452 and 480 nm. The structure of Dye 5 is given below:

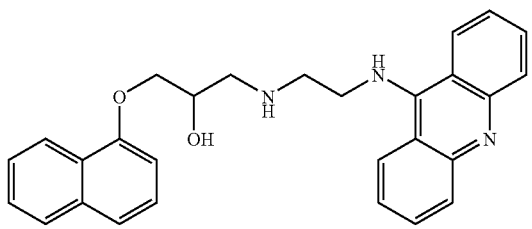

Dye 5

Example 6

Preparation of Dye 6

A mixture of 4-chloro-7-nitro-2,1,3-benzoxadiazole (0.5 g, 2.5 mmol), 2-amino-5-diethylaminopentane (0.58 mL, 3 mmol) and cesium carbonate (0.98 g, 3 mmol) in acetonitrile (5 mL) was refluxed for 1 hour. Reaction mixture cooled and volatiles were removed in the rotary evaporator. The residue thus obtained was dissolved in a mixture of ethyl acetate (40 mL) and water (40 mL). The organic layer was separated, washed with water (2×), brine (2×), dried (MgSO$_4$) and evaporated. The crude dye thus obtained was purified on Biotage (Si, SNAP 25 g) using a gradient of methanol (2% to 40% over 18 column volume) in methylene chloride to provide Dye 6 as a yellow residue (61 mg). Abs (max, methanol)= 467 nm; $\epsilon$=30,200 $M^{-1}cm^{-1}$. The structure of Dye 6 is given below:

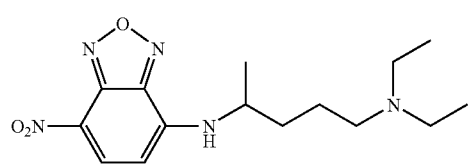

Dye 6

Example 6

Fluorescence Microscopy-Based Assay of Lysosomal Perturbation

The Lysosomal Storage Disorder known as Fabry disease arises from a deficiency of the enzyme alpha-galactosidase A, which leads to an accumulation of the glycolipid known as globotriaosylceramide (aka ceramide trihexoside) within endothelium, striated muscle (skeletal, cardiac), smooth muscle, and renal epithelium. This accumulation leads to an impairment of their proper function. The condition affects hemizygous males, as well as both heterozygous and homozygous females; males tend to experience the most severe clinical symptoms, while females vary from virtually no symptoms to those as serious as males. This variability is thought to be due to X-inactivation patterns during embryonic development. Diagnosis of Fabry disease can be difficult even in a homozygous male. Some patients, renal variants, may lack classic manifestation of Fabry disease such as acroparesthesia, angiokeratoma and corneal lesion. This difficulty is compounded in a heterozygous female who may be variably affected from lionization (from Dr. Mary Lyon's theory of random X-inactivation). It should also be recognized that serum-galactosidase A is frequently normal in female patients. It has recently been noted that chloroquine, hydroxychloroquine and amiodarone therapy can result in abnormal storage of biochemically and ultrastructurally similar vacuolar inclusions in many of the same cells as Fabry disease and consequently results in similar clinical manifestations (see Müller-Höcker et al, *Human* Pathology 34:285-289 (2003); Albay et al, *Modern* Pathology 18:733-738 (2005); and Bracamonte et al, *Am J Kidney Disease* 48:844-850 (2006), incorporated herein by reference).

Stable cell lines derived from patients with Fabry disease can not be found in cell line repositories, such as American Type Tissue Collection (Manassas, Va.), and are not readily available to the research community. Consequently, an in vitro cell culture model mimicking Fabry disease was generated by incubation of cells with chloroquine.

U2OS human osteosarcoma cells were maintained in McCoy's 5a modified medium supplemented with 10% FBS and 100 units/ml penicillin/streptomycin (Invitrogen, Carlsbad, Calif.) in a humidified 37° C., 5% $CO_2$ environment. Cells were allowed to proliferate on glass slides or were seeded into 96-well plates at a density of $2 \times 10^4$ cells/well and allowed to attach overnight. The cells were plated such that at the end of the experiment, they reached about 90% confluency.

The fluorescence-based lysosomal perturbation assay was established by first incubating cells cultivated on glass slides for 4-24 hours with chloroquine (8-64 µM final concentration), a well known phospholipidosis-inducing agent. Control cells were incubated with 0.1% (v/v) dimethyl sulfoxide (DMSO), which served as the vehicle control. Cells were then briefly (15 min) incubated with a combination of Dye 1 and Hoechst 33342 dye. Following incubation, cells grown on glass microscope slides were covered with glass coverslips, sealed with nail polish and observed using an inverted Axiovert 200M microscope (Carl Zeiss, Inc., Oberkochen, Germany). Images were acquired with a 63× objective lens (Zeiss). Fluorescence emission intensity and wavelength maximum of Dye 1 is not significantly altered in the pH range of 4.0 to 9.0, allowing interpretation of any increase in fluorescence intensity as an indication of the accumulation of the probe within the cells, rather than as a variation in dye response to lysosomal pH values.

Examination of the distribution of the Dye 1 in cells treated with chloroquine, revealed a punctate pattern of cytoplasmic staining that increased in a dose-dependent manner (FIG. 1). Cells were subsequently stained with Dye 1 for 15 minutes. Nuclei were counter-stained with Hoechst 33342 dye. In FIG. 1, control U2OS cells are shown in (A), cells pre-treated for 18 hours with 8 µM chloroquine in (B), cells pre-treated for 18 hours with 16 µM chloroquine in (C) and cells pre-treated for 18 hours with 64 µM chloroquine in (D). This staining pattern was also consistently observed for other drugs that are known to induce phospholipidosis, such as chlorpromazine, fluoxetine, pimozide and verapamil (further described in Example 4). For all the cited drugs the levels of Dye 1 in the cells increased in a dose-dependent manner until cytotoxic doses of the test agent were attained, which led to a loss of cells. Typically at high doses of test agent the cells remaining on the slide displayed diffuse cytoplasmic staining with Dye 1. Negative control compounds, the vehicle control and untreated medium showed minimal accumulation of Dye 1, which was strictly confined to the lysosomes. The ability of Dye 1 to detect vacuole accumulation in the described in vitro cell culture model mimicking Fabry disease strongly supports the present invention and its suitability for the detection of genetically derived lysosomal storage diseases.

Example 7

Fluorescence Microscopy with Dye 6

HeLa cells were maintained in Dulbecco's modified Eagles medium supplemented with 10% FBS, 100 units/ml penicillin/streptomycin (Invitrogen, Carlsbad, Calif.) and MEM non essential amino acids in a humidified 37° C., 5% $CO_2$ environment. Cells were allowed to proliferate on glass slides at a density of $2 \times 10^4$ cells/well and allowed to attach overnight. The cells were plated such that at the end of the experiment, they reached about 90% confluency.

The fluorescence-based lysosomal perturbation assay was established by first incubating cells cultivated on glass slides for 6 hours with chloroquine (120 µM final concentration), a well known phospholipidosis-inducing agent. Control cells were incubated with 0.1% (v/v) dimethyl sulfoxide (DMSO), which served as the vehicle control. Cells were then briefly (15 min) incubated with Dye 6 at room temperature. Following incubation, cells grown on glass microscope slides were covered with glass coverslips, sealed with nail polish and observed using an Olympus BX51 microscope. Images were acquired with a 40× objective lens. Examination of the distribution of the Dye 6 in cells treated with chloroquine, revealed an increase in fluorescence intensity of lysosomal staining. The untreated cells gave a low level of fluorescent staining.

Example 8

Fluorescence Microplate Based Assay of Lysosomal Perturbation

In order to increase throughput and reduce handling time, the fluorescence microscopy-based lysosomal perturbation assay was scaled up to a 96-well microplate plate assay format and analyzed using a fluorescence microplate reader.

Figure 2:
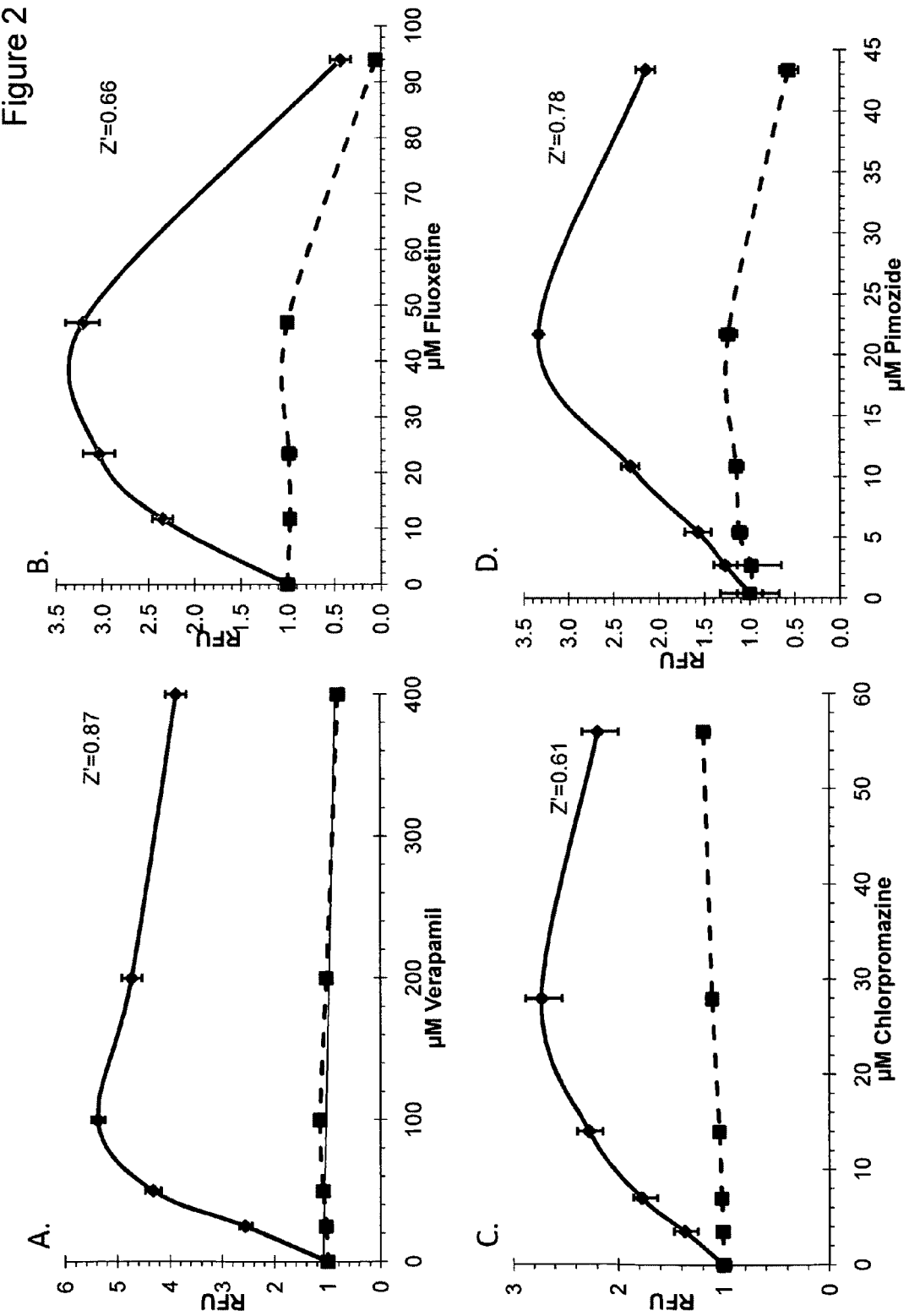
FIG. 2: Relative fluorescent intensity of U2OS cells treated with known cationic amphiphilic drugs.

(FIG. 2). Monitoring cell number per well by determining overall blue fluorescence emission intensity, as indicated by the nuclear Hoechst 33342 dye, was performed to identify generalized compound toxicity. Fluorescence intensity of the cells cultured on the 96-well plates was measured using a FLUOstar OPTIMA Multifunction Microplate Reader (BMG LabTech, Offenburg, Germany). Dye 1 and Hoechst 33342 nuclear counter-stain can be read with Texas Red filter set and DAPI filter set, respectively (Hoechst excitation ~300 nm and emission ~480 nm, Dye 1 excitation ~570 nm and emission ~670 nm). Fluorescence intensity was expressed as percentage of the vehicle control value. Values for Dye 1 fluorescence can be normalized to those of Hoechst 33342 dye fluorescence to control for any loss in cell number. Cells were treated with verapamil in (A), fluoxetine in (B), chlorpromazine in (C) and pimozide in (D) for 18 hours, and then stained with Dye 1 (solid lines with solid diamonds) and Hoechst 33342 (dashed line with squares). Concentrations of compounds that resulted in a greater than 30% decrease in overall cell number using the described assay were flagged as being toxic doses, as especially evident in FIGS. 2B and 2D. This benchmark has previously been established in a phospholipidosis assay using a fluorescent lipid analog as well as in a high content screening assay of autophagy (Nioi et al 2008; Zhang et al, 2007). Microscopic examination of wells highlighted as containing generally toxic doses of a test compound demonstrated diffuse cytoplasmic staining of Dye 1 instead of the anticipated localized punctuate staining associated with lysosomes and lamellar bodies. Scaling-up to the higher throughput microplate format did not affect the sensitivity of detection nor the reproducibility of the assay, as demonstrated by re-testing the reference compounds and comparing the results with those obtained in the fluorescence microscopy assay. However, it was found to be critical to check for any generalized toxicity-related artifacts thru monitoring Hoechst 33342 dye signal.

In high-throughput screening activities, experimenters often compare a large number (hundreds of thousands to tens of millions) of single measurements of unknown samples to positive and negative control samples. The particular choice of experimental conditions and measurements is called an assay. Large screens are expensive in time and resources. Therefore, prior to starting a large screen, smaller test (or pilot) screens are used to assess the quality of an assay, in an attempt to predict if it would be useful in a high-throughput setting. The Z-factor is an attempt to quantify the suitability of a particular assay for use in a full-scale, high-throughput screen. Extreme conservatism is used in high throughput screening, due to the large number of tests being performed.

The Z-factor is defined in terms of four parameters: the means and standard deviations of both the positive (p) and negative (n) controls ($\mu_p$, $\sigma_p$, and $\mu_n$, $\sigma_n$). Given these values, the Z-factor is defined as:

$$Z\text{-factor} = 1 - \frac{3 \times (\sigma_p + \sigma_n)}{|\mu_p - \mu_n|}.$$

In practice, the Z-factor is estimated from the sample means and sample standard deviations:

$$\text{Estimated Z-factor} = 1 - \frac{3 \times (\hat{\sigma}_p + \hat{\sigma}_n)}{|\hat{\mu}_p - \hat{\mu}_n|}.$$

When tested in the 96-well assay format using the cited cationic amphiphilic drugs, the Dye 1-based assay demonstrated a Z-factor value of at least 0.60. This falls within the range of 0.5 and 1, which is defined as a high quality assay by the applied statistical parameter (Zhang et al, 1999). $EC_{50}$ values for the test drugs ranged from 6 µM for chlorpromazine to 30 µM for verapamil, with chloroquine itself having an $EC_{50}$ value of 15 µM.

Example 9

Comparison with a Prototypical Fluorescent Phospholipid Analog-Based Assay

Figure 3:
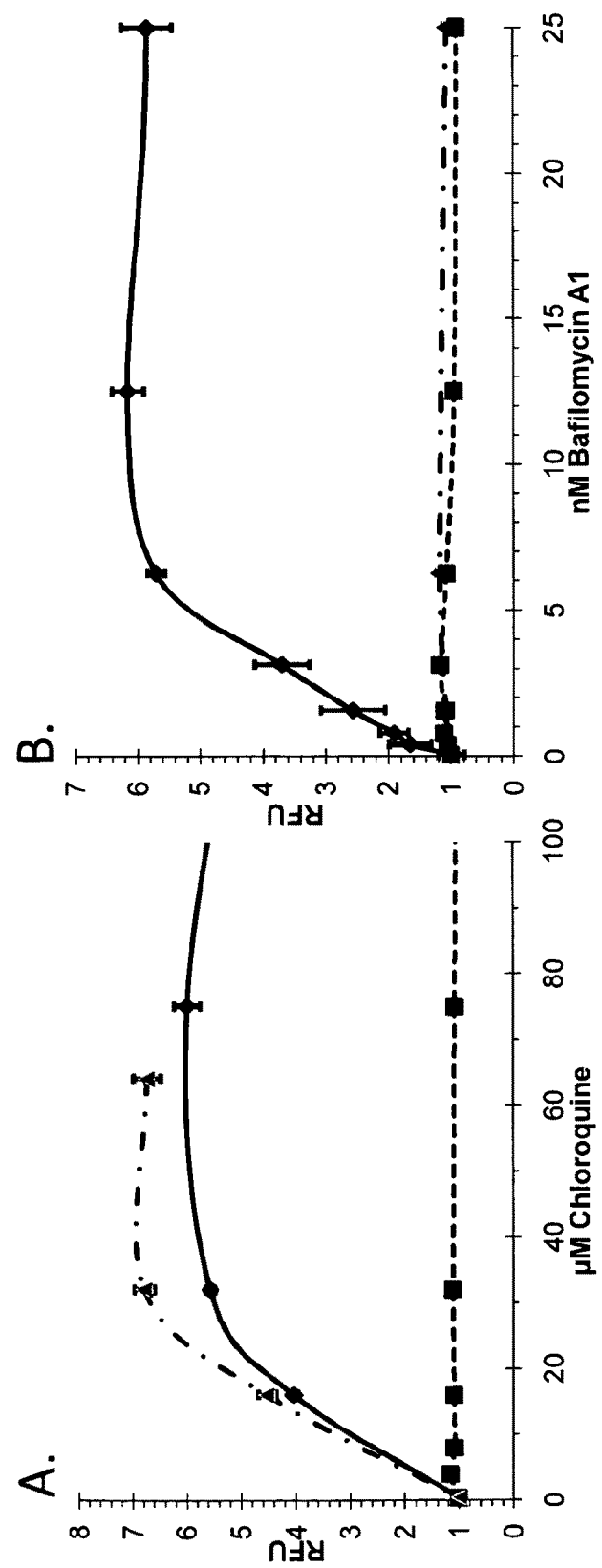
FIG. 3: Relative fluorescent intensity of U2OS cells treated with chloroquine or bafilomycin A1, using a fluorescent phospholipid analog versus a fluorescent cationic amphiphilic tracer for detection of vacuolation.

Many assays of phospholipidosis, including the Lipid-Tox assay (Invitrogen, Carlsbad, Calif.), are based upon co-incubating cells with a fluorescent phospholipid analog for an extended period of time, along with the drug or test agent being evaluated, and then monitoring signal generation in fixed and permeabilized cells. Dye 1 is not a fluorescent phospholipid analog, but instead is a cationic amphiphilic fluorophore tracer. Cells are incubated with the drug or test agent in isolation and then briefly treated with the tracer dye before evaluation in live cells. This prompted us to speculate that since the two assays are based upon fundamentally different mechanisms, they might also differ in terms of the types of test agents that elicited a positive response. Choloroquine, a prototypical phospholipidosis-inducing agent, and bafilomycin A, an agent well known to induce the accumulation of autophagosomes, were evaluated using both Dye 1 and Lipid-Tox dye-based assays (FIG. 3). FIG. 3 shows relative fluorescent intensity of U2OS cells treated with chloroquine (A) or bafilomycin A1 (B) at different concentrations for 24 hours. Cells stained with Lipid-Tox dye (solid triangles dash-dot line) were incubated in the presence of the fluorescent lipid for 24 hours during treatment with the drugs. Cells stained with Dye 1 (solid diamond solid line) or Hoechst 33342 (solid square dashed line) were stained for 15 minutes post drug incubation. Both assays reliably predicted that chloroquine induced an expansion in the lysosomal compartment (FIG. 3A). However, only Dye 1 identified the increased vacuolation arising from bafilomycin A treatment (FIG. 3B). The calculated $EC_{50}$ value for this particular compound was determined to be 3 nM in Dye 1 based assay, easily making it the most potent agent screened in our study. This suggests that the Lipid-Tox assay is strictly speaking a phospholipidosis assay while Dye 1 assay is capable of detecting vacuolation arising from both phospholipidosis and disruption of trafficking in the autophagy pathway.

Thus, in addition to authentic compounds that cause phospholipidosis, agents that cause the accumulation of autophagosomes by blocking the downstream lysosomal pathway and/or intracellular trafficking of autophagosomes may also lead to increases in the accumulation of intracellular Dye 1 signal in the described assay. For example, Bafilomycin A1, a macrolide antibiotic isolated from Streptomyces griseus, is a particularly potent agent in our assay. Initial screening of this compound using the ICCB library revealed it to be cytotoxic, but rescreening at much lower doses demonstrated its ability to increase vacuole number and volume. Bafilomycin A1 is a rather specific vacuolar type $H^+$-ATPase inhibitor which is known to increase the numbers of intracellular autophagosomes, purportedly by blocking the ability of the lysosome to degrade them [Yamamoto et al, 1998; Zhang et al, 2008]. The bafilomycin A1 results suggest that the described assay should be considered a measure of generalized dysfunction of the lysosomal-dependent catabolic pathway, which leads to the accumulation of autophagosomes, and thus relevant to autophagy in general, as well as phospholipidosis in particular.

Example 10

Compound Library Screening

Small molecule activators and inhibitors are commonly used to provide insight into both the mode of regulation and physiological roles of various subcellular targets. However, more extensive screening of these compounds generally reveals that most have overlapping specificities, complicating interpretation of their overall effects on biological systems. As proof-of-principle, U2OS cells were incubated with the 480 compounds in the ICCB known bioactives compound library (Enzo Life Sciences) overnight at concentrations of 0.1-53 µM (1000-fold dilution of the stock), and then evaluated using the described lysosomal perturbation assay. In the preliminary screen, test agents were employed at a single dose in an effort to identify any potential lysosome-modifying agents. Our objective was to benchmark the assay workflow, not to exhaustively classify all of the compounds in the library. It would be advisable to use a range of concentrations for each test agent in order to reduce the number of false negative results obtained with the described assay. The compounds listed in Table 1 increased staining by greater than three standard deviations compared with untreated control cells.

The cursory screening activity led to the identification of five compounds that induced increases in vacuolation without causing obvious cellular toxicity (boldface entries, Table One). These agents all elicited a dose-dependent response, with estimated $EC_{50}$ values ranging from 1 to 7 µM.

Two of the five agents, propranolol and GF-109203X, have previously been reported to induce phospholipidosis in cells. Propranolol is a well-known and extensively investigated cationic amphiphilic drug that induces phospholipidosis (Cramb, 1986; Lemieux et al, 2004). High micromolar concentrations of the drug are rapidly taken up and accumulated by a wide range of cultured cells, with a steady state being reached after 40-60 min administration and half maximum uptake within 4-10 min. The rate of propranolol dissociation is much slower than the rate of uptake, with 10% of the propranolol remaining associated with the cells after a 90 minute incubation period in the absence of the drug (Cramb, 1986).

In a recent cell-based HTS screen for anthrax toxin inhibitors, GF-109203X was identified as an agent displaying both protein kinase C-inhibitory and lysosomotropic activities (Sanchez et al, 2007). Screening of bisindolylmaleimide compounds related to GF-109203X which lack protein kinase C inhibitory activity but retain tertiary amines and thus the

TABLE 1

Positive compound hits from a screen of the ICCB Known Bioactive Compounds Library. U2OS cells were treated with the highlighted compounds at the indicated concentrations for 18 hours. Compounds that displayed increased fluorescence from incubation with Dye 1 by greater than 3 standard deviations relative to the untreated cells are summarized in the table. Relative Lyso stain represents the intensity of Dye 1 fluorescence of treated cells compared to the untreated control. Relative Hoechst stain represents the intensity of the Hoechst 33342 fluorescence of treated cells compared to the untreated control, which indicates the number of cells remaining after the assay. Compounds listed in boldface do not decrease the signal from Hoechst by more than 30%.

| NAME | Classification | Action | µM used | Relative Lyso Stain | Relative Hoechst Stain |
|---|---|---|---|---|---|
| Ro 20-1724 | Inhibitors | phosphodiesterase (PDE4) inhibitor | 18 µM | 190% | 53% |
| Bafilomycin A1 | Inhibitors | vaculolar ATPase inhibitor | 1 µM | 176% | 58% |
| E6 Berbamine | Inhibitors | calmodulin inhibitor | 7 µM | 230% | 100% |
| Ro 31-8220 | Kinase inhibitors | PKC inhibitor | 9 µM | 146% | 89% |
| Propranolol (S-) | CNS receptor ligands | adrenoceptor antagonist (beta) | 17 µM | 142% | 88% |
| SB-431542 | Kinase inhibitors | ALK4, ALK5, ALK7 inhibitor | 13 µM | 154% | 101% |
| Rottlerin | Kinase inhibitors | PKC delta inhibitor | 10 µM | 187% | 34% |
| GF-109203X | Kinase inhibitors | PKC inhibitor | 12 µM | 197% | 87% |
| Tyrphostin 9 | Kinase inhibitors | PDGF-R tyrosine kinase inhibitor | 18 µM | 200% | 31% |

Figure 4:
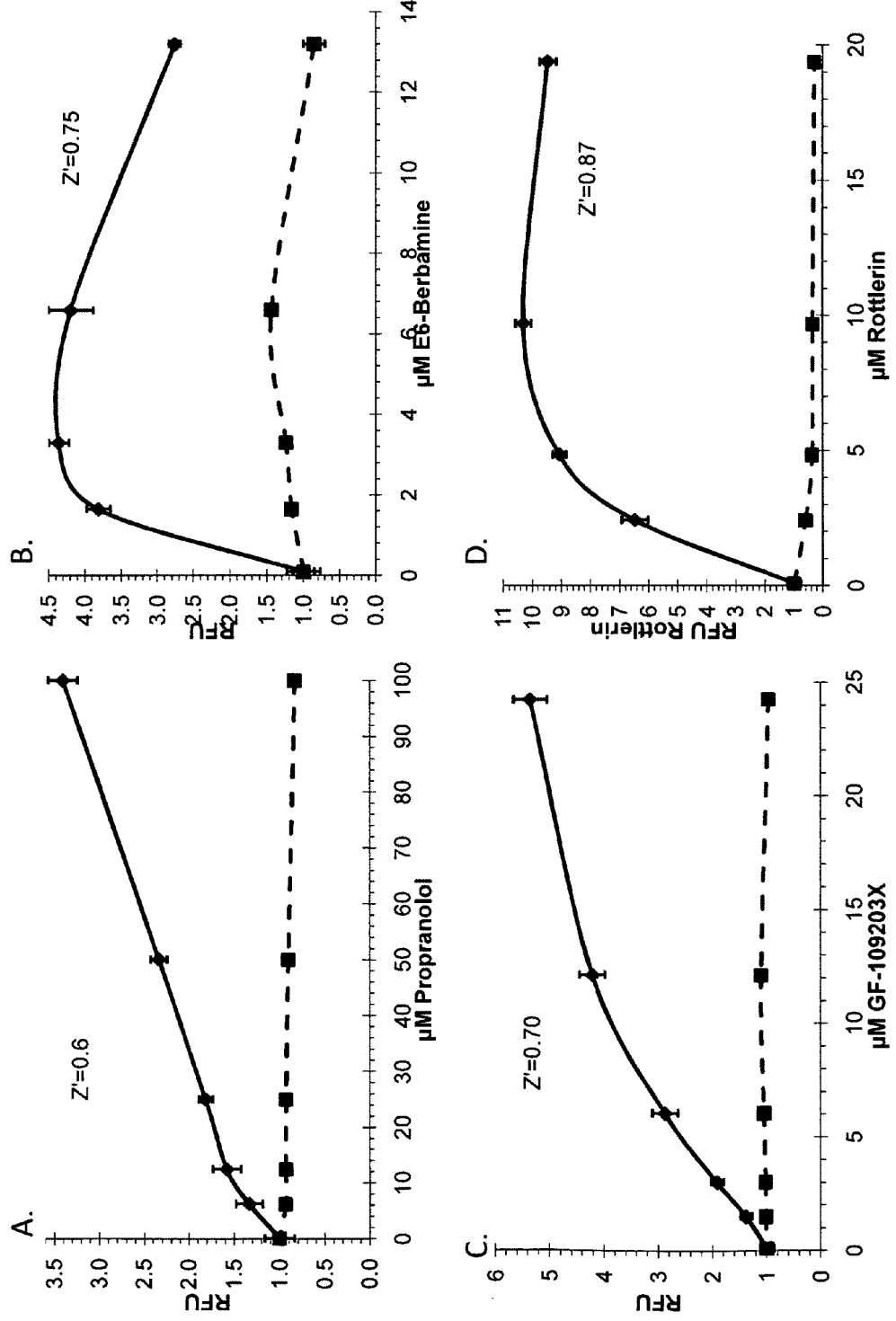
FIG. 4: Positive leads from a compound library screen obtained using the fluorescent cationic amphiphilic tracer method.

FIG. 4 highlights representative results obtained from four of the test compounds determined to generate a positive response in the assay. FIG. 4 shows relative fluorescent intensity of U2OS cells treated with propranolol in FIG. 4(A), E6-berbamine in FIG. 4(B), GF-109203X in FIG. 4(C) or rottlerin in 4(D) for 18 hours, after staining with Dye 1 (solid lines with solid diamonds) and Hoechst 33342 dye (dashed line with squares) Many of the agents used in the screen caused a loss of cells, an indication of generalized cellular toxicity at the compound concentration evaluated. Rottlerin (FIG. 4D) is an example of a generally cytotoxic compound, which was apparent from a substantial decrease in the Hoechst 33342 dye signal. Observation of rottlerin-treated cells by fluorescence microscopy confirmed the microplate-based results, with those cells remaining attached to the tissue culture surface displaying diffuse cytoplasmic red staining.

potential to neutralize endosomal pH, was subsequently undertaken by the investigators. This established that the observed toxin inhibitory activity correlated strongly with the presence of the tertiary amines, but not with protein kinase C inhibition (Sanchez et al, 2007). In our own screen, Ro 31-8220, a bisindolylmaleimide compound closely related to GF-109203X, but not to our knowledge previously described as a lysosome-perturbation agent, was also found to be a positive hit. A structurally unrelated protein kinase Cδ-inhibitor, rottlerin, increased subcellular accumulation of Dye 1 but displayed significant toxicity, as demonstrated by loss of Hoechst 33342 dye signal in the assay. Re-examination of this compound over a broad range of concentrations revealed it to be generally cytotoxic (data not shown). Intracellular accumulation of Dye 1 in treated cells was always diffuse and cytoplasmic, demonstrating it to be a false positive hit. Our results, taken together with that of Sanchez et al, 2007, suggests that the observed accumulation of Dye 1 in vacuoles correlates strongly with the cationic amphiphilic nature of the bisindolylmaleimide compounds, rather than any protein kinase C inhibitory activity.

Two other positive hits in our screen were SB-431542 and berbamine. SB-431542 is reported to be a transforming growth factor-β-receptor antagonist that serves as a potent competitive ATP binding site kinase inhibitor for the downstream activin receptor-like kinases, ALK4, ALK5 and ALK7 (Hjelmeland et al, 2004). Physiologically, SB-431542 has previously been shown to inhibit cell proliferation and block cell motility. Berbamine is reported to selectively induce caspase-3-dependent apoptosis of leukemia NB4 cells via a survivin-mediated pathway (Xu et al, 2006). We are not aware of any previous reports that these two agents have a propensity to induce vacuolation in cells, and indeed their chemical structures are not consistent with them belonging to the cationic amphiphilic class of compounds.

Example 11

Figure 5:
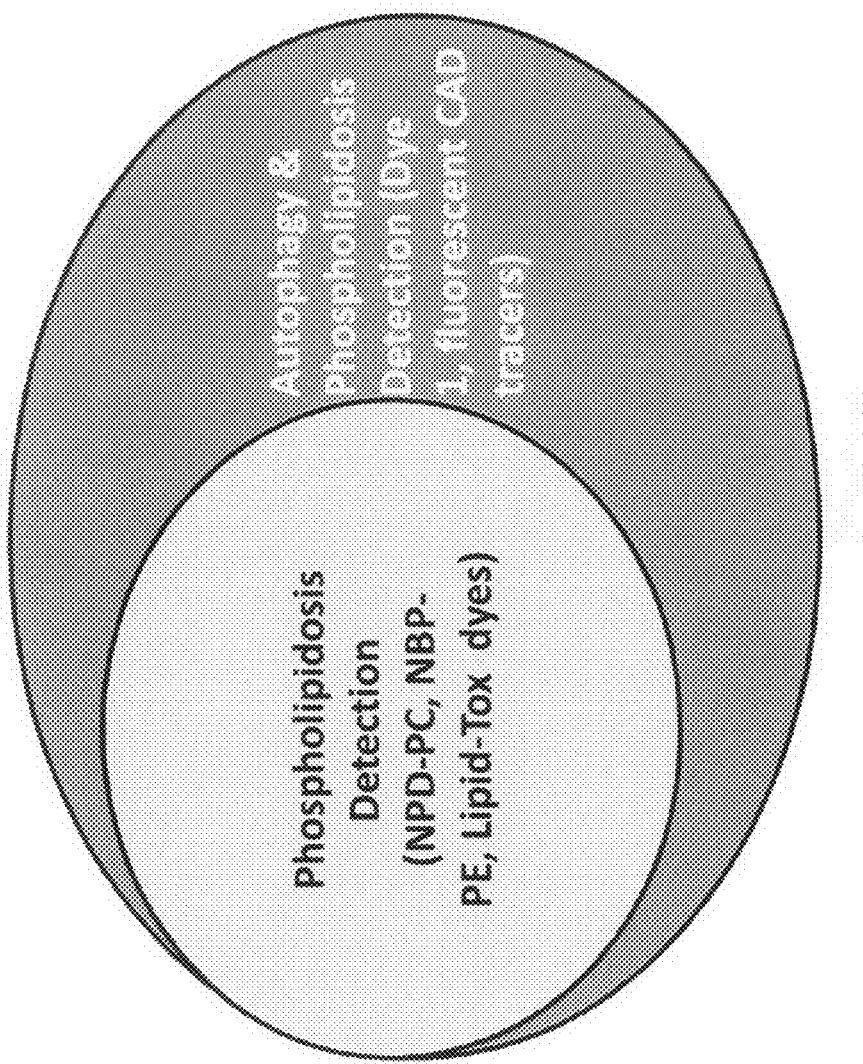
FIG. 5: Schematic illustration for multiplexed detection of phospholipidosis inducers and autophagy pathway inhibitors.

Distinguishing Between Induction of Phospholipidosis and Inhibition of the Autophagy Pathway Example 8 demonstrates that the fluorescent cationic amphillic tracer dyes while sharing with the fluorescent phospholipid analogs an ability to identify phospholipidosis activators also distinctly reveal agents that inhibit the autophagy pathway, leading to accumulation of vacuoles such as autophagosomes and autophagolysosomes. This relationship is highlighted schematically in FIG. 5. Agents such as NBD-PE (N-(-7-nitrobenz-2-oxa-1,3-diazol-4-yl)-1,2-dihexadecanoyl-sn-glycero-3-phosphoethanolamine), NBD-PC (1-acyl-2-(12[(7-nitro-2-1-3-benzoxadiazol-4yl)amino] dodecanoyl)phosphatidylcholine), CF-PE (1,2-dioleoyl-sn-glycero-3-phosphoethanolamine-N-(carboxyfluorescein)) and Lipid-Tox reagent (Invitrogen) can be used in a consolidated workflow along with cationic amphiphilic fluorophore tracers, like Dye 1 in order to differentiate between phospholipidosis activators and autophagy pathway inhibitors, providing unprecedented insight into the overall dysfunction of the lysosomal-dependent catabolic pathway.

For example, CF-PE was suspended in ethanol and diluted in the cell culture medium (McCoy's 5a modified medium, as described in Example 3) to give a solution (CF-PE medium) with final concentration of 50 µM (0.46% ethanol). NBD-PE medium was then sonicated and filtered through a 0.22 mm filter. The prepared was then applied to U2OS cells growing in a 96-well microplate. After an equilibration period of 24 h, the cell culture medium was replaced with CF-PE medium with or without each test compound, and the cells were incubated at 37° C. for an additional 24 h. After incubation, the cells were rinsed with medium and further incubated with the same medium containing Dye 1 and Hoechst 33342 dye for an additional 15 min at 37° C. in 5% $CO_2$ atmosphere.

Fluorescence signal was determined using a standard microplate reader, as described in example 4, except that CF-PE was additionally read at an excitation wavelength of 492 nm and an emission wavelength of 517 nm. Autophagy pathway inhibitors such as bafilomycin A generate an increased red signal but low green signal relative to vehicle-treated controls in the assay. Phospholipidosis inducers like chloroquine lead to both an increased green and red signal. Generalized cytotoxicity is evident as a substantial decrease in blue signal (≥30%) relative to vehicle-treated control cells.

Autophagy is known to be substantially up-regulated in colon cancer tissues when compared with the surrounding non-cancerous counterparts. The multiplexed assay of lysosomal catabolic dysfunction should find application in identifying drug candidates that form the basis of new therapeutic strategies based upon the regulation of autophagy.

Example 12

Fluorescence Microscopy-Based and Microplate Assay-Based Staining Using Dye 2

HeLa cervical cancer cells were maintained in Delbeccos modified Eagle medium supplemented with 10% FBS, 1% MEM non-essential amino acids and 100 units/ml penicillin/streptomycin (Invitrogen, Carlsbad, Calif.) in a humidified 37° C., 5% $CO_2$ environment. Cells were allowed to proliferate on glass slides or were seeded into 96-well plates at a density of $2\times10^4$ cells/well and allowed to attach overnight.

Cells grown on glass microscope slides were stained with 5 µM Dye 2, washed with PBS containing 2% FBS, covered with glass coverslips, sealed with nail polish and observed using an inverted Axiovert 200M microscope (Carl Zeiss, Inc., Oberkochen, Germany). Images were acquired with a 63× objective lens (Zeiss). Fluorescent and brightfield images are shown in FIG. 6.

Figure 7:
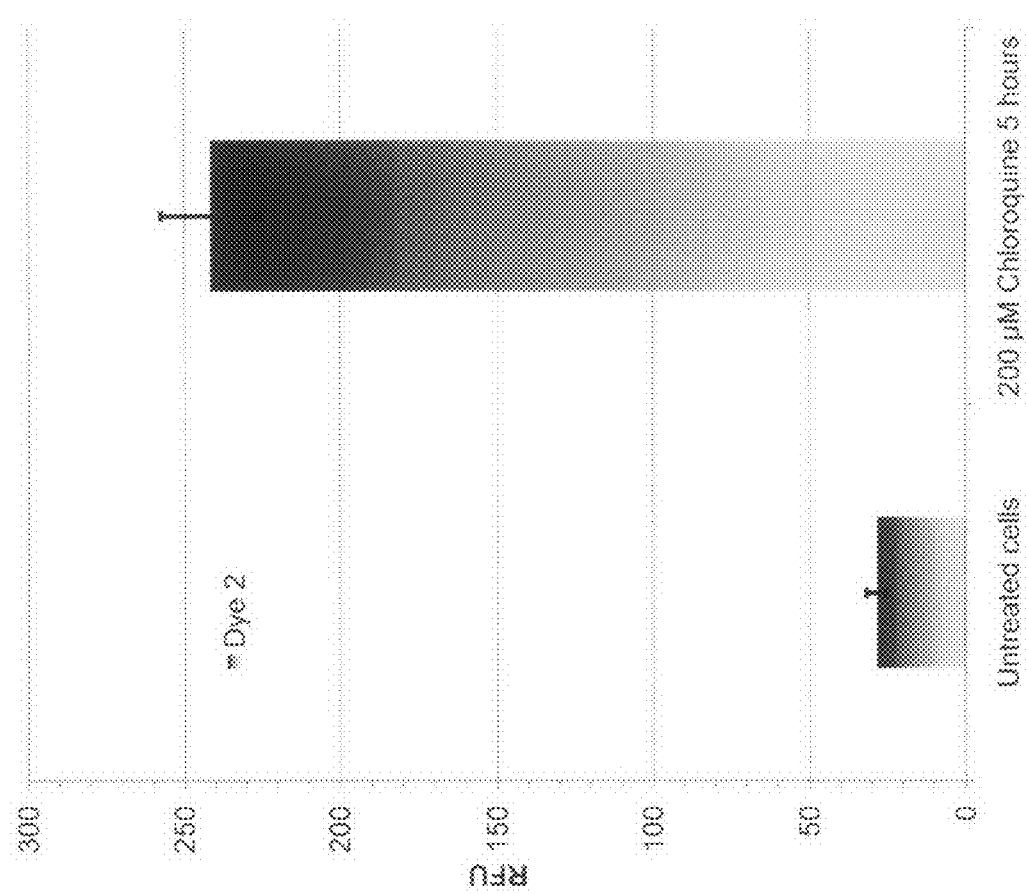
FIG. 7: Relative fluorescent intensities of HeLa cells treated with 200 µM chloroquine for 5 hours and untreated cells.

The fluorescence-based lysosomal perturbation assay was established by first incubating cells cultivated on a microtiter plate for 5 hours with chloroquine (200 µM final concentration), a well known phospholipidosis-inducing agent. Control cells were incubated with 0.1% (v/v) dimethyl sulfoxide (DMSO), which served as the vehicle control. Cells were then briefly (30 min) incubated with 40 µM Dye 2 in PBS containing 2% FBS. Following incubation, cells were washed with PBS containing 2% FBS. Finally 60 µl of PBS containing 2% FBS was added to each well, and the fluorescence of each well was determined using a Synergy Mx plate scanner (BioTek, Winooski, Vt.) set to excite at 660 nM and emit at 705 nM. The results are shown in FIG. 7.

Example 13

Fluorescence Microscopy-Based Staining Using Dye 5

HeLa cervical cancer cells were maintained in Delbeccos modified Eagle medium supplemented with 10% FBS, 1% MEM non-essential amino acids and 100 units/ml penicillin/streptomycin (Invitrogen, Carlsbad, Calif.) in a humidified 37° C., 5% $CO_2$ environment. Cells were allowed to proliferate on glass slides and allowed to attach overnight.

Cells grown on glass microscope slides were stained with 10 µM Dye 5, washed with PBS containing 2% FBS, covered with glass coverslips, sealed with nail polish and observed using an inverted Axiovert 200M microscope (Carl Zeiss, Inc., Oberkochen, Germany). Images were acquired with a 63× objective lens (Zeiss). Fluorescent ant brightfield images are shown in FIG. 8.

Example 14

Model System That Mimics a Lysosomal Storage Disease (Niemann-Pick Disease)

Sphingomyelin is the primary sphingophospholipid in mammalian cells. A simplified reaction pathway scheme for its biosynthesis is presented below. Sphingomyelinases catalyze the lysosomal degradation of sphingomyelin. Inherited deficiencies of acid sphingomyelinase activity result in various clinical forms of the Niemann-Pick disease, which are characterized by massive lysosomal accumulation of sphingomyelin.

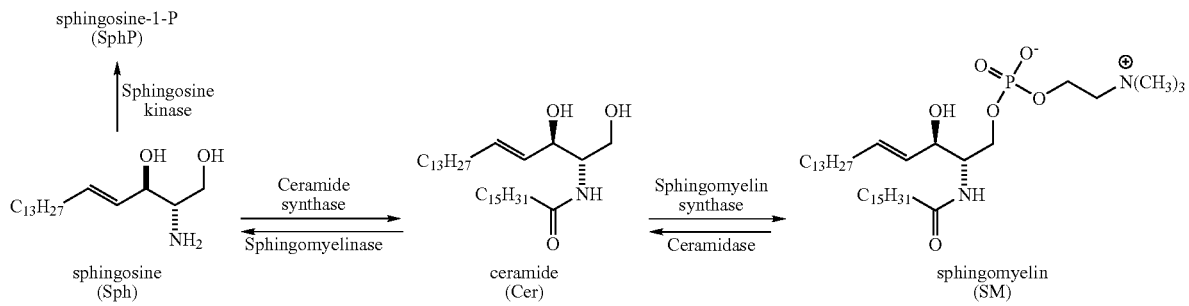

Stable cell lines derived from patients with Niemann-Pick disease can not be found in cell line repositories, such as American Type Tissue Collection (Manassas, Va.), and are not readily available to the research community. Consequently, an in vitro tissue culture model of sphingolipidosis was devised using 2R,3S,4E)-N-methyl-5-(4'pentylphenyl)-2-aminopent-4-ene-1,3-diol, designated SK1-I (BML-258), a potent, water soluble, isozyme-specific inhibitor of sphingosine kinase-1. In contrast to pan-sphingosine kinase inhibitors, SK1-I does not inhibit sphingosine kinase-2, protein kinase C, or numerous other protein kinases. U-2-OS human osteosarcoma cells were seeded at 22,500 cells/well, grown overnight, and then treated with a final concentration of 0, 2.5, 5, 10 or 20 µM of SK1-I for 18.5 hours. Next, the cells were briefly treated with compound 1 and the nuclear Hoechst 33342 dye, as described in Example 7. Fluorescence signal was read on a BioTek Synergy Mx microplate reader at excitation values of 340 and 540 nm and emission values of 480 and 680 nm. Dose-dependent increases in emission values at 680 nm were observed upon treatment with SK1-I (Z'=0.55), signifying excessive accumulation of sphingolipids within the vacuolar compartment. Cell viability was maintained under all treatment conditions, as signified by relatively constant 480 nm emission intensity values from the Hoechst dye. Fluorescence microscope-based examination of the wells confirmed that compound 1 staining of the cells was confined to the vacuolar structures. This in vitro model confirms the feasibility of using the assay for detecting aberrant accumulation of sphingolipids in cells, and by extension the feasibility of using the assay in monitoring inherited lysosomal storage diseases, such as Niemann-Pick disease.

Many obvious variations will no doubt be suggested to those of ordinary skill in the art, in light of the above detailed description and examples of the present invention. It will be appreciated by those skilled in the art that any arrangement which is calculated to achieve the same purpose may be substituted for the specific embodiments shown. This application and invention are intended to cover any adaptations or variations of the present invention. All such variations are fully embraced by the scope and spirit of the invention as more particularly defined in the claims that now follow.

What is claimed is:

1. A method of detecting the presence of a lysosomal storage disease in a subject comprising the steps of:
   (a) obtaining a sample containing cells from said subject;
   (b) contacting said sample with a cationic amphiphilic tracer compound that localizes to a vacuole in a cell selected from

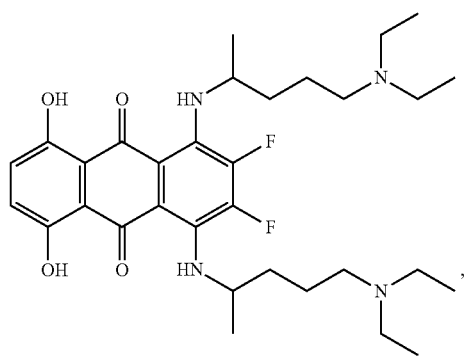 [SMILES: CCN(CC)CCCC(C)Nc1c(F)c(F)c(NC(C)CCCN(CC)CC)c2c1C(=O)c1c(O)ccc(O)c1C2=O]

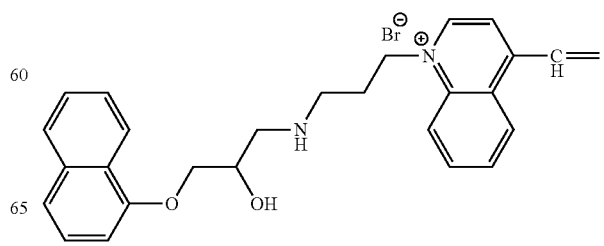

-continued

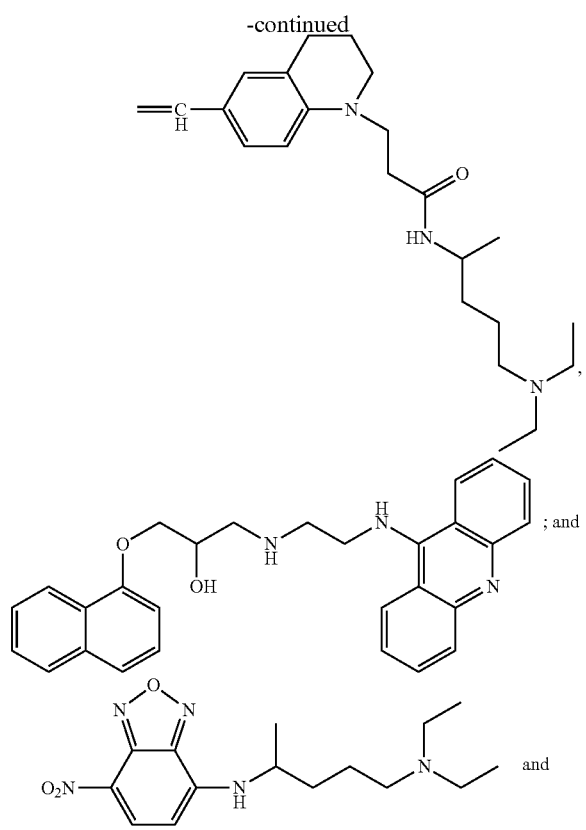

(c) detecting said cationic amphiphilic tracer compound, thereby determining whether there exists an excess above normal accumulation of vacuoles within said cells of the sample, said excess above normal accumulation of vacuoles being indicative of the lysosomal storage disease, wherein the lysosomal storage disease is selected from Fabry disease and Niemann-Pick disease, and wherein said cells in step (a) are selected from lymphocytes, granulocytes, macrophages, monocytes, or a combination thereof.

2. The method of claim 1, wherein the subject is known to have a lysosomal storage disease based upon previous genetic or metabolic testing.

3. The method of claim 2, further comprising comparing the excess above normal accumulation of vacuoles in the cells in the sample with the accumulation of vacuoles in cells of a prior sample obtained from the subject.

4. The method of claim 3, wherein the subject has been treated with a drug or remedy used to manage, treat or cure the lysosomal storage disease between the prior sample and the sample obtained in step (a).

5. The method of claim 3, wherein the subject has been treated with a drug candidate between the prior sample and the sample obtained in step (a).

6. The method of claim 3, wherein the subject has been exposed to a suspected toxic agent between the prior sample and the sample obtained in step (a).

7. The method of claim 1, further comprising the steps of (a') providing a reference sample of normal cells from a subject known not to have lysosomal storage disease; (b') contacting said sample of normal cells with the same cationic amphiphilic tracer compound of step (b); and (c') comparing the accumulation of vacuoles in the sample obtained from the subject known or suspected of having a lysosomal storage disease with the accumulation in said reference sample of normal cells.

8. The method of claim 1, wherein said subject is a mammal.

9. The method of claim 1, wherein said mammal is human.

10. The method of claim 1, wherein the cationic amphiphilic tracer compound is

11. The method of claim 1, wherein the cationic amphiphilic tracer compound is

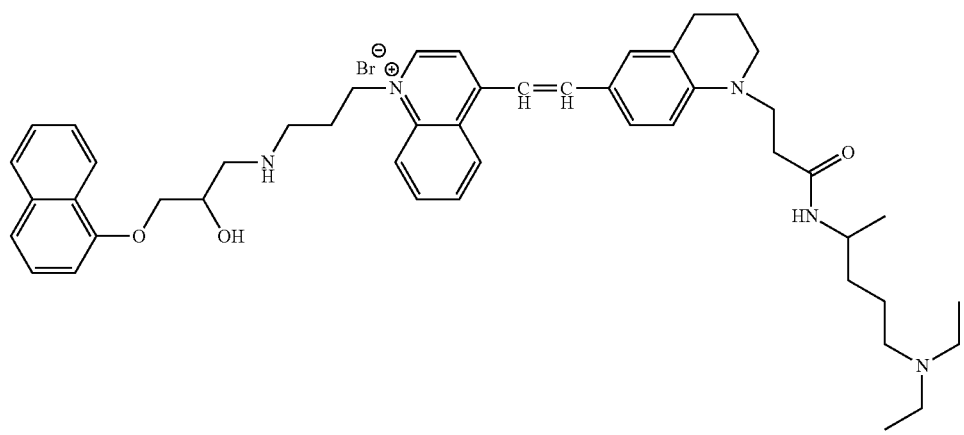

12. The method of claim 1, wherein the cationic amphiphilic tracer compound is

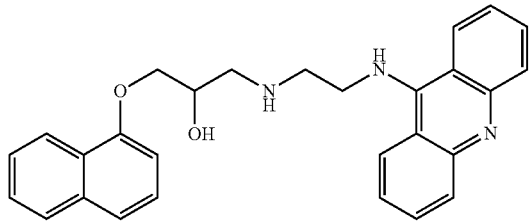

13. The method of claim 1, wherein the cationic amphiphilic tracer compound is

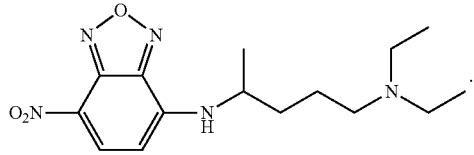 [SMILES: CCN(CC)CCCC(C)Nc1ccc([N+](=O)[O-])c2nonc12]

14. A method of detecting Fabry disease, phospholipodosis, or lysosomal perturbation in U2OS human cells comprising the steps of:
(a) obtaining a sample containing said cells;
(b) contacting said sample with the cationic amphiphilic tracer compound having the structure

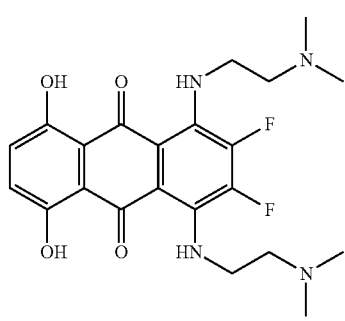

Dye 1 and
(c) detecting said cationic amphiphilic tracer compound, thereby determining whether there exists an excess above normal accumulation of vacuoles within said cells of the sample, said excess above normal accumulation of vacuoles being indicative of lysosomal perturbation or Fabry disease.

15. A method of detecting lysosomal perturbation in HeLa cells comprising the steps of:
(a) obtaining a sample containing said cells;
(b) contacting said sample with a cationic amphiphilic tracer compound selected from

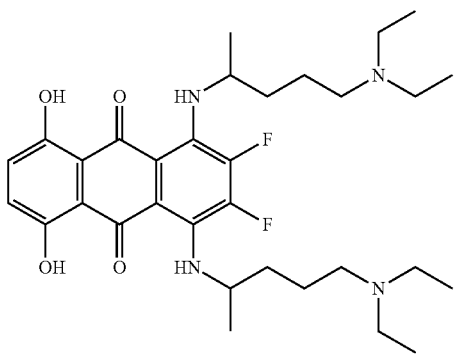

Dye 2

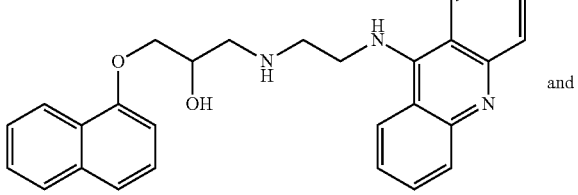

Dye 5 and

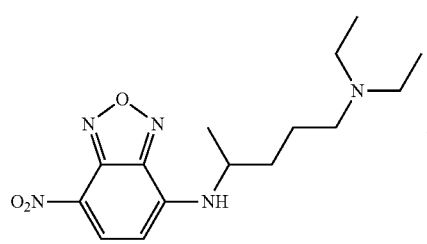

Dye 6

16. The method of claim 14 or claim 15, wherein the lysosomal perturbation is selected from phospholipidosis, expansion in the lysosomal compartment, vacuolar inclusions, vacuolation and disruption of trafficking in the autophagy pathway.

17. A method of detecting Niemann-Pick disease in human cells comprising the steps of:
(a) obtaining a sample containing said cells;
(b) contacting said sample with the cationic amphiphilic tracer compound having the structure

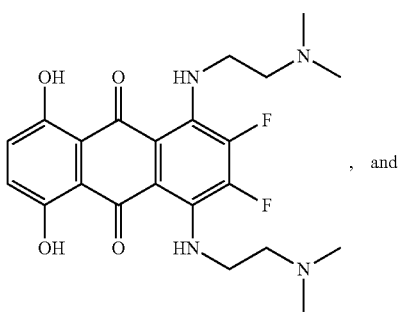

Dye 1

, and (c) detecting said cationic amphiphilic tracer compound, thereby determining whether there exists an excess above normal accumulation of sphingomyelin in vacuolar structures.

* * * * *